US008853494B2

(12) United States Patent
Bonin et al.

(10) Patent No.: US 8,853,494 B2
(45) Date of Patent: Oct. 7, 2014

(54) STRESS TOLERANT TRANSGENIC CROP PLANTS

(75) Inventors: Christopher P. Bonin, St. Louis, MO (US); Paolo Castiglioni, St. Louis, MO (US); Robert L. D'Ordine, St. Louis, MO (US); Jacqueline E. Heard, St. Louis, MO (US); Robert M. McCarroll, St. Louis, MO (US); Sara Salvador, St. Louis, MO (US); Michael J. Storek, Cambridge, MA (US)

(73) Assignee: Monsanto Technology LLC, St. Louis, MO (US)

( * ) Notice: Subject to any disclaimer, the term of this patent is extended or adjusted under 35 U.S.C. 154(b) by 638 days.

(21) Appl. No.: 13/059,116

(22) PCT Filed: Aug. 14, 2009

(86) PCT No.: PCT/US2009/053807
§ 371 (c)(1),
(2), (4) Date: Jul. 1, 2011

(87) PCT Pub. No.: WO2010/019838
PCT Pub. Date: Feb. 18, 2010

(65) Prior Publication Data
US 2011/0258742 A1    Oct. 20, 2011

Related U.S. Application Data

(60) Provisional application No. 61/089,058, filed on Aug. 15, 2008.

(51) Int. Cl.
 *C12N 15/31*     (2006.01)
 *C12N 15/63*     (2006.01)
 *C12N 15/82*     (2006.01)
 *C07K 14/32*     (2006.01)
 *C07K 14/195*    (2006.01)

(52) U.S. Cl.
 CPC .......... *C07K 14/195* (2013.01); *C12N 15/8273* (2013.01)
 USPC .......... 800/298; 435/468; 435/410; 536/23.7; 530/300; 530/324

(58) Field of Classification Search
 None
 See application file for complete search history.

(56) References Cited

U.S. PATENT DOCUMENTS 7,786,353 B2    8/2010  Fernandes
8,450,561 B2 *  5/2013  Beazley et al. ............... 800/289
(Continued)

FOREIGN PATENT DOCUMENTS

WO    9705165 A1       2/1997
WO    2005033318 A2    4/2005
WO    2010019838 A2    2/2010

OTHER PUBLICATIONS

Max et al. Optimized variants of the cold shock protein from in vitro selection: structural basis of their high thermostability. Journal of Molecular Biology. 2007. 369(4): 1087-1097.*

(Continued)

*Primary Examiner* — Brent T Page
*Assistant Examiner* — Ashley K Buran
(74) *Attorney, Agent, or Firm* — Thompson Coburn LLP; Charles P. Romano

(57) ABSTRACT

Disclosed herein are novel variant bacterial cold shock proteins and recombinant DNA for expressing such proteins to produce transgenic plants with enhanced stress tolerance and/or enhanced yield.

16 Claims, 7 Drawing Sheets

Bs_CspB (SEQ ID NO:1)

(56) References Cited

U.S. PATENT DOCUMENTS

| | | | |
|---|---|---|---|
| 2005/0097640 A1* | 5/2005 | Fernandes | 800/289 |
| 2011/0035835 A1* | 2/2011 | Fernandes | 800/275 |

OTHER PUBLICATIONS

GenBank Accession No. 215L$_{13}$ X. published Jun. 12, 2007. p. 1.*

Kim et al. Cold-inducible zinc finger-containing glycine-rich RNA-binding protein contributes to the enhancement of freezing tolerance in *Arabidopsis thaliana*. The Plant Journal. 2005. 42: 890-900.*

GenBank Accession No. P32081. Cold shock protein cspB (Major cold shock protein). Published Jul. 10, 2007. pp. 1-6.*

Gioia et al. Paradoxical DNA repair and peroxide resistance gene conservation in Bacillus pumilis SAFR-032. PLOS One. 2007. 9 (e928): 1-10.*

GenBank Accession No. ABV61546. Major cold shock protein. Published Sep. 26, 2007. pp. 1-2.*

GenBank Accession No. CP000813. Bacillus pumilis SAFR-032, complete genome. Published Sep. 26, 2007. pp. 1.*

Chaikam et al, "Comparison of Structure, Function and Regulation of Plant Cold Shock Domain Proteins to Bacterial and Animal Cold Shock Domain Proteins", BMB Rep., Jan. 2010, pp. 1-8, vol. 43(1).

Chaikam et al, "Functional Characterization of Two Cold Shock Domain Proteins from *Oryza sativa*.", Plant, Cell and Environment, Apr. 4, 2008 (online publication), pp. 995-1006, vol. 31(7).

Horn et al, "Structure and Function of Bacterial Cold Shock Proteins", Cellular and Molecular Life Sciences, Apr. 16, 2007 (online publication), pp. 1457-1470, vol. 64.

Castiglioni et al., "Bacterial RNA Chaperones Confer Abiotic Stress Tolerance in Plants and Improved Grain Yield in Maize Under Water-Limited Conditions", Plant Physiology, Jun. 2008, pp. 446-455, vol. 147, No. 2, American Society of Plant Biologists, Rockville, MD, US.

Yamanaka, "Cold Shock Response in *Escherichia coli*", Journal of Molecular Microbiology and Biotechnology, Nov. 1999, pp. 193-202, vol. 1, No. 2, Horizon Scientific Press.

Graumann et al., "A Superfamily of Proteins that Contain the Cold-shock Domain", Reviews, Aug. 1998, pp. 286-290, TIBS 23.

Yamanaka et al., "The CspA Family in *Escherichia coli*: Multiple Gene Duplication for Stress Adaptation", Molecular Microbiology, 1998, pp. 247-255, vol. 27 No. 2.

Xia et al., "Acquirement of Cold Sensitivity by Quadruple Deletion of the cspA Family and its Suppression by PNPase S1 Domain in *Escherichia coli*", Molecular Microbiology, 2001, pp. 179-188, vol. 40 No. 1.

* cited by examiner

| | Reg1 | Reg2 | | Reg3 | | Reg4 | Reg5 | |
|---|---|---|---|---|---|---|---|---|
| Tt_Csp1(SEQ3) | ---MVRGKVK WFNAE | KGYGFI EREDGT- | DVFVHYSAI | EGEGFK | TLEEGQAVEF | EVVQAAK | -G-P QASKVRKL | ------- |
| Bs_CspB(SEQ1) | --MVEGKVK WFNSE | KGFGFI EVEGQD- | DVFVHFSAI | QGEGFK | TLEEGQAVSF | EIVEGNR | -G-P QAANVTKE | A------ |
| Tm_Csp1(SEQ2) | ---MRGKVK WFDSK | KGYGFI TKDEGG- | DVFVHWSAI | EMEGFK | TLKEGQVVEF | EIQEGKK | -G-P QAAHVKVV | E------ |
| Ec_CspC(SEQ4) | MA-KIKGQVK WFNES | KGFGFI TPADGSK | DVFVHFSAI | QGNGFK | TLAEGQNVEF | EIQDGQK | -G-P AAVNVTAI | ------- |
| Ec_CspG(SEQ7) | MSNKMTGLVK WFNAD | KGFGFI TPDDGSK | DVFVHFTAI | QSNEFR | TLNENQKVEF | SIEQGQR | -G-P AAANVVTL | ------- |
| Ec_CspD(SEQ5) | ---MEKGTVK WFNNA | KGFGFI CPEGGGE | DIFAHYSTI | QMDGYR | TLKAGQSVQF | DVHQGPK | -G-N HASVIVPV | EVEAAVA |
| Ab_Csp2(SEQ6) | ---MATGTVK FFAQD | KGFGFI TPDNGGP | DVFVHISAV | GFGG-- | SLQDGQKVSY | ELGQDRK | TGKS KAENVTLL | ------- |

FIGURE 1

Bs_CspB (SEQ ID NO:1)

| | DOT1 | | DOT2 | | DOT3 | | DOT4 | | DOT5a | DOT5b | | DOT6 | |
|---|---|---|---|---|---|---|---|---|---|---|---|---|---|
| MVEGKVKWF | NSEKGF | GFI | EVEGQD | DVFVHFSAI | QGEGFK | | TLEEG | Q AVSF | EIVE | G NR | G PQA | ANVTKE | A |
| | AAD | Y | AAA | AA | EAD | YR | S A D | | ALEA | AK | | GH | AAA |
| | DDG | | KED | EE | DG | | D N | | DVLP | D | | IK | EEI |
| | TGK | | PG | GG | EK | | G S | | G QQ | E | | SQ | IIK |
| | NN | | QK | KK | IN | | K | | K S | G | | T | KTL |
| | TR | | TL | PN | KR | | N | | N * | H | | V | VVP |
| | S | | M | RR | MS | | R | | R | K | | | Q |
| | | | P | TS | N | | S | | S | P | | | T |
| | | | Q | T | R | | T | | T | Q | | | V |
| | | | R | | S | | | | | R | | | |
| | | | T | | T | | | | | S | | | |
| | | | | | V | | | | | T | | | |

SEQUENCE LISTING

```
<160> NUMBER OF SEQ ID NOS: 708

<210> SEQ ID NO 1
<211> LENGTH: 67
<212> TYPE: PRT
<213> ORGANISM: Artificial Sequence
<220> FEATURE:
<223> OTHER INFORMATION: synthetic sequence, Bs-CspBL2V

<400> SEQUENCE: 1

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

```
<210> SEQ ID NO 2
<211> LENGTH: 66
<212> TYPE: PRT
<213> ORGANISM: Thermotoga maritima
<220> FEATURE:
<223> OTHER INFORMATION: Tm_Csp1

<400> SEQUENCE: 2

Met Arg Gly Lys Val Lys Trp Phe Asp Ser Lys Lys Gly Tyr Gly Phe
1               5                   10                  15

Ile Thr Lys Asp Glu Gly Gly Asp Val Phe Val His Trp Ser Ala Ile
            20                  25                  30

Glu Met Glu Gly Phe Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 3
<211> LENGTH: 66
<212> TYPE: PRT
<213> ORGANISM: Thermoanaerobacter tengcongensis
<220> FEATURE:
<223> OTHER INFORMATION: Tt_Csp1

<400> SEQUENCE: 3

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Val Val Gln Ala Ala Lys Gly Pro Gln Ala Ser Lys Val Arg
    50                  55                  60

Lys Leu
65

<210> SEQ ID NO 4
<211> LENGTH: 69
<212> TYPE: PRT
<213> ORGANISM: Escherichia coli
<220> FEATURE:
<223> OTHER INFORMATION: Ec_CspC

<400> SEQUENCE: 4

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Ile Gln Asp Gly Gln Lys Gly Pro Ala Ala Val
    50                  55                  60

Asn Val Thr Ala Ile
65

<210> SEQ ID NO 5
<211> LENGTH: 74
<212> TYPE: PRT
<213> ORGANISM: Escherichia coli
```

<220> FEATURE:
<223> OTHER INFORMATION: Ec_CspD

<400> SEQUENCE: 5

Met Glu Lys Gly Thr Val Lys Trp Phe Asn Asn Ala Lys Gly Phe Gly
1               5                   10                  15

Phe Ile Cys Pro Glu Gly Gly Gly Glu Asp Ile Phe Ala His Tyr Ser
                20                  25                  30

Thr Ile Gln Met Asp Gly Tyr Arg Thr Leu Lys Ala Gly Gln Ser Val
            35                  40                  45

Gln Phe Asp Val His Gln Gly Pro Lys Gly Asn His Ala Ser Val Ile
    50                  55                  60

Val Pro Val Glu Val Glu Ala Ala Val Ala
65                  70

<210> SEQ ID NO 6
<211> LENGTH: 67
<212> TYPE: PRT
<213> ORGANISM: Agrobacterium tumefaciens
<220> FEATURE:
<223> OTHER INFORMATION: Ab_Csp2

<400> SEQUENCE: 6

Met Ala Thr Gly Thr Val Lys Phe Phe Ala Gln Asp Lys Gly Phe Gly
1               5                   10                  15

Phe Ile Thr Pro Asp Asn Gly Gly Pro Asp Val Phe Val His Ile Ser
                20                  25                  30

Ala Val Gly Phe Gly Gly Ser Leu Gln Asp Gly Gln Lys Val Ser Tyr
            35                  40                  45

Glu Leu Gly Gln Asp Arg Lys Thr Gly Lys Ser Lys Ala Glu Asn Val
    50                  55                  60

Thr Leu Leu
65

<210> SEQ ID NO 7
<211> LENGTH: 70
<212> TYPE: PRT
<213> ORGANISM: Escherichia coli
<220> FEATURE:
<223> OTHER INFORMATION: Ec_CspG

<400> SEQUENCE: 7

Met Ser Asn Lys Met Thr Gly Leu Val Lys Trp Phe Asn Ala Asp Lys
1               5                   10                  15

Gly Phe Gly Phe Ile Thr Pro Asp Asp Gly Ser Lys Asp Val Phe Val
                20                  25                  30

His Phe Thr Ala Ile Gln Ser Asn Glu Phe Arg Thr Leu Asn Glu Asn
            35                  40                  45

Gln Lys Val Glu Phe Ser Ile Glu Gln Gly Gln Arg Gly Pro Ala Ala
    50                  55                  60

Ala Asn Val Val Thr Leu
65                  70

<210> SEQ ID NO 8
<211> LENGTH: 204
<212> TYPE: DNA
<213> ORGANISM: Artificial Sequence
<220> FEATURE:
<223> OTHER INFORMATION: synthetic sequence, Bs-CspBL2V DNA

<400> SEQUENCE: 8

```
atggtagaag gtaaagtaaa atggttcaac tctgaaaaag gtttcggatt catcgaagta    60
gaaggtcaag acgatgtatt cgttcatttc tctgctattc aaggcgaagg cttcaaaact   120
ttagaagaag gccaagctgt ttcttttgaa atcgttgaag gaaaccgcgg accacaagct   180
gctaacgtta ctaaagaagc gtag                                           204

<210> SEQ ID NO 9
<211> LENGTH: 201
<212> TYPE: DNA
<213> ORGANISM: Thermotoga maritima
<220> FEATURE:
<223> OTHER INFORMATION: Tm_Csp1 DNA

<400> SEQUENCE: 9
atgcgcggca aggtgaagtg gttcgactcc aagaagggct acggcttcat cacgaaggac    60
gagggcggcg atgtcttcgt gcactggagc gccatcgaga tggagggctt caagacgctc   120
aaggagggtc aagtggtcga gttcgagatt caagagggaa agaaaggtcc gcaggccgcg   180
cacgtcaagg tcgtcgaatg a                                              201

<210> SEQ ID NO 10
<211> LENGTH: 201
<212> TYPE: DNA
<213> ORGANISM: Thermoanaerobacter tengcongensis
<220> FEATURE:
<223> OTHER INFORMATION: Tt_Csp1 DNA

<400> SEQUENCE: 10
atggtgcgcg gcaaggtgaa gtggttcaac gctgagaagg gctacggctt catcgagcgc    60
gaggacggca ccgacgtctt cgtgcactac tccgccatcg agggcgaggg tttcaagacg   120
ctggaggagg acaggccgt cgagttcgaa gtcgtccaag ccgcgaaggg tccacaggcg   180
agcaaggtcc ggaaactgtg a                                              201

<210> SEQ ID NO 11
<211> LENGTH: 210
<212> TYPE: DNA
<213> ORGANISM: Escherichia coli
<220> FEATURE:
<223> OTHER INFORMATION: Ec_CspC DNA

<400> SEQUENCE: 11
atggcaaaga ttaaaggtca ggttaagtgg ttcaacgagt ctaaaggttt tggcttcatt    60
actccggctg atggcagcaa agatgtgttc gtacacttct ccgctatcca gggtaatggc   120
ttcaaaactc tggctgaagg tcagaacgtt gagttcgaaa ttcaggacgg ccagaaaggt   180
ccggcagctg ttaacgtaac agctatctag                                     210

<210> SEQ ID NO 12
<211> LENGTH: 225
<212> TYPE: DNA
<213> ORGANISM: Escherichia coli
<220> FEATURE:
<223> OTHER INFORMATION: Ec_CspD DNA

<400> SEQUENCE: 12
atggaaaagg gtactgttaa gtggttcaac aatgccaaag ggtttggttt catctgccct    60
gaaggcggcg gcgaagatat tttcgctcat tattccacca ttcagatgga tggttacaga   120
acgctaaaag ctggacaatc cgttcagttt gatgtccacc aggggccaaa aggcaatcac   180
```

```
gccagtgtta ttgtgcccgt cgaagtagaa gcggcagtcg catag            225
```

<210> SEQ ID NO 13
<211> LENGTH: 204
<212> TYPE: DNA
<213> ORGANISM: Agrobacterium tumefaciens
<220> FEATURE:
<223> OTHER INFORMATION: Ab_Csp2 DNA

<400> SEQUENCE: 13

```
atggcaactg gcactgtaaa attcttcgct caggacaagg gctttggctt cattacccct     60
gacaatggcg gtcctgacgt attcgttcac atctcggcag tcggtttcgg cggctctctt    120
caggatggtc agaaggtgag ctacgagttg ggacaagacc gcaagaccgg taaatcgaaa    180
gccgagaacg tcactctcct ttag                                           204
```

<210> SEQ ID NO 14
<211> LENGTH: 213
<212> TYPE: DNA
<213> ORGANISM: Escherichia coli
<220> FEATURE:
<223> OTHER INFORMATION: E. coli cspG DNA

<400> SEQUENCE: 14

```
atgtctaata aaatgactgg tttagtaaaa tggtttaacg cagataaagg ttttggcttt     60
atcactcctg atgatggcag caaagacgtt ttcgtccatt tcaccgccat ccagagcaat    120
gaattccgca cgctgaacga aaatcagaaa gttgaatttt ctattgagca ggggcaacgt    180
ggccccgcgg cagcgaacgt tgttacgctc tag                                 213
```

<210> SEQ ID NO 15
<211> LENGTH: 67
<212> TYPE: PRT
<213> ORGANISM: Artificial Sequence
<220> FEATURE:
<223> OTHER INFORMATION: synthetic sequence, Bs-CspB variant 2

<400> SEQUENCE: 15

Met Val Glu Gly Lys Val Lys Trp Phe Asn Asp Arg Lys Gly Tyr Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 16
<211> LENGTH: 74
<212> TYPE: PRT
<213> ORGANISM: Artificial Sequence
<220> FEATURE:
<223> OTHER INFORMATION: synthetic sequence, Ec_CspD variant 2
      Chimeric Tm_Csp1_R1_Ec_CspD_bb

<400> SEQUENCE: 16

Met Glu Lys Gly Thr Val Lys Trp Phe Asp Ser Lys Lys Gly Phe Gly
1               5                   10                  15

Phe Ile Cys Pro Glu Gly Gly Gly Glu Asp Ile Phe Ala His Tyr Ser
            20                  25                  30

```
Thr Ile Gln Met Asp Gly Tyr Arg Thr Leu Lys Ala Gly Gln Ser Val
        35                  40                  45

Gln Phe Asp Val His Gln Gly Pro Lys Gly Asn His Ala Ser Val Ile
 50                  55                  60

Val Pro Val Glu Val Glu Ala Ala Val Ala
 65                  70

<210> SEQ ID NO 17
<211> LENGTH: 67
<212> TYPE: PRT
<213> ORGANISM: Artificial Sequence
<220> FEATURE:
<223> OTHER INFORMATION: synthetic sequence, Bs-CspB variant 5
      Chimeric Tm_Csp1_R2_Bs_CspB_bb

<400> SEQUENCE: 17

Met Val Glu Gly Lys Val Lys Trp Phe Asn Ser Glu Lys Gly Phe Gly
 1               5                  10                  15

Phe Ile Thr Lys Asp Glu Gly Gly Asp Val Phe Val His Phe Ser Ala
                20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
 50                  55                  60

Lys Glu Ala
 65

<210> SEQ ID NO 18
<211> LENGTH: 74
<212> TYPE: PRT
<213> ORGANISM: Artificial Sequence
<220> FEATURE:
<223> OTHER INFORMATION: synthetic sequence, Ec_CspD variant 5
      Chimeric Bs_CspB_R3_Ec_CspD_bb

<400> SEQUENCE: 18

Met Glu Lys Gly Thr Val Lys Trp Phe Asn Asn Ala Lys Gly Phe Gly
 1               5                  10                  15

Phe Ile Cys Pro Glu Gly Gly Gly Glu Asp Ile Phe Ala His Tyr Ser
                20                  25                  30

Thr Ile Gln Gly Glu Gly Phe Lys Thr Leu Lys Ala Gly Gln Ser Val
        35                  40                  45

Gln Phe Asp Val His Gln Gly Pro Lys Gly Asn His Ala Ser Val Ile
 50                  55                  60

Val Pro Val Glu Val Glu Ala Ala Val Ala
 65                  70

<210> SEQ ID NO 19
<211> LENGTH: 67
<212> TYPE: PRT
<213> ORGANISM: Artificial Sequence
<220> FEATURE:
<223> OTHER INFORMATION: synthetic sequence, Ab_Csp2 variant 1
      Chimeric  Ec_CspC_R4_Ab_Csp2_bb

<400> SEQUENCE: 19

Met Ala Thr Gly Thr Val Lys Phe Phe Ala Gln Asp Lys Gly Phe Gly
 1               5                  10                  15

Phe Ile Thr Pro Asp Asn Gly Gly Pro Asp Val Phe His Ile Ser
                20                  25                  30
```

Ala Val Gly Phe Gly Gly Ser Leu Gln Asp Gly Gln Lys Val Ser Tyr
            35                  40                  45

Glu Ile Gln Asp Gly Gln Lys Thr Gly Lys Ser Lys Ala Glu Asn Val
        50                  55                  60

Thr Leu Leu
65

<210> SEQ ID NO 20
<211> LENGTH: 66
<212> TYPE: PRT
<213> ORGANISM: Artificial Sequence
<220> FEATURE:
<223> OTHER INFORMATION: synthetic sequence, Tm_Csp1 variant 3
      Chimeric Ec_CspC_R4_Tm_Csp1_bb

<400> SEQUENCE: 20

Met Arg Gly Lys Val Lys Trp Phe Asp Ser Lys Gly Tyr Gly Phe
1               5                   10                  15

Ile Thr Lys Asp Glu Gly Gly Asp Val Phe Val His Trp Ser Ala Ile
            20                  25                  30

Glu Met Glu Gly Phe Lys Thr Leu Lys Glu Gly Gln Val Val Glu Phe
        35                  40                  45

Glu Ile Gln Asp Gly Gln Lys Gly Pro Gln Ala Ala His Val Lys Val
    50                  55                  60

Val Glu
65

<210> SEQ ID NO 21
<211> LENGTH: 67
<212> TYPE: PRT
<213> ORGANISM: Artificial Sequence
<220> FEATURE:
<223> OTHER INFORMATION: synthetic sequence, Bs-CspB variant 7
      Chimeric Ec_CspC_R5_Bs_CspB_bb

<400> SEQUENCE: 21

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Ala Ala Val Asn Val Thr
    50                  55                  60

Ala Ile Ala
65

<210> SEQ ID NO 22
<211> LENGTH: 66
<212> TYPE: PRT
<213> ORGANISM: Artificial Sequence
<220> FEATURE:
<223> OTHER INFORMATION: synthetic sequence, Tt_Csp1 variant 1
      Chimeric Tm_Csp1_R3_Tt_Csp1_bb

<400> SEQUENCE: 22

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Met Glu Gly Phe Lys Thr Leu Glu Glu Gly Gln Ala Val Glu

```
                        35                  40                  45

Phe Glu Val Val Gln Ala Ala Lys Gly Pro Gln Ala Ser Lys Val Arg
    50                  55                  60

Lys Leu
65

<210> SEQ ID NO 23
<211> LENGTH: 69
<212> TYPE: PRT
<213> ORGANISM: Artificial Sequence
<220> FEATURE:
<223> OTHER INFORMATION: synthetic sequence, Ab_Csp2 variant 2
      Chimeric Tm_Csp1_R3_Ab_Csp2_bb

<400> SEQUENCE: 23

Met Ala Thr Gly Thr Val Lys Phe Phe Ala Gln Asp Lys Gly Phe Gly
1               5                   10                  15

Phe Ile Thr Pro Asp Asn Gly Gly Pro Asp Val Phe Val His Ile Ser
                20                  25                  30

Ala Val Glu Met Glu Gly Phe Lys Thr Leu Gln Asp Gly Gln Lys Val
                35                  40                  45

Ser Tyr Glu Leu Gly Gln Asp Arg Lys Thr Gly Lys Ser Lys Ala Glu
    50                  55                  60

Asn Val Thr Leu Leu
65

<210> SEQ ID NO 24
<211> LENGTH: 67
<212> TYPE: PRT
<213> ORGANISM: Artificial Sequence
<220> FEATURE:
<223> OTHER INFORMATION: synthetic sequence, Bs-CspB variant 8

<400> SEQUENCE: 24

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
                35                  40                  45

Phe Glu Ile Val Glu Gly Asn Arg Gly Pro Gln Ala Ile Gln Val Ile
    50                  55                  60

Glu Pro Ala
65

<210> SEQ ID NO 25
<211> LENGTH: 67
<212> TYPE: PRT
<213> ORGANISM: Artificial Sequence
<220> FEATURE:
<223> OTHER INFORMATION: synthetic sequence, Bs-CspB variant 9

<400> SEQUENCE: 25

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
                35                  40                  45

Phe Glu Ile Val Glu Gly Asn Arg Gly Pro Gln Ala Gly Lys Val Lys
```

```
                50              55              60

Ile Lys Ala
65

<210> SEQ ID NO 26
<211> LENGTH: 76
<212> TYPE: PRT
<213> ORGANISM: Artificial Sequence
<220> FEATURE:
<223> OTHER INFORMATION: synthetic sequence, Bs-CspB variant 10

<400> SEQUENCE: 26

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ile Gln Val Ile
        50                  55                  60

Lys Leu Ala Ser Trp Gln Ser Tyr Lys Thr Ser Val
65                  70                  75

<210> SEQ ID NO 27
<211> LENGTH: 67
<212> TYPE: PRT
<213> ORGANISM: Artificial Sequence
<220> FEATURE:
<223> OTHER INFORMATION: synthetic sequence, Bs-CspB variant 11

<400> SEQUENCE: 27

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Gly Gln Val Val
        50                  55                  60

Asn Gln Arg
65

<210> SEQ ID NO 28
<211> LENGTH: 68
<212> TYPE: PRT
<213> ORGANISM: Artificial Sequence
<220> FEATURE:
<223> OTHER INFORMATION: synthetic sequence, Bs-CspB variant 13

<400> SEQUENCE: 28

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Val Gln Val Cys
        50                  55                  60

Asn Thr Ser Val
65
```

<210> SEQ ID NO 29
<211> LENGTH: 67
<212> TYPE: PRT
<213> ORGANISM: Artificial Sequence
<220> FEATURE:
<223> OTHER INFORMATION: synthetic sequence, Bs-CspB variant 14

<400> SEQUENCE: 29

Met Val Glu Gly Lys Val Lys Trp Phe Asn Ser Glu Lys Gly Phe Gly
1               5                   10                  15

Phe Ile Thr Thr Asp Gly Ala Asn Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 30
<211> LENGTH: 67
<212> TYPE: PRT
<213> ORGANISM: Artificial Sequence
<220> FEATURE:
<223> OTHER INFORMATION: synthetic sequence, Bs-CspB variant 15

<400> SEQUENCE: 30

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Asn Glu Asp Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 31
<211> LENGTH: 65
<212> TYPE: PRT
<213> ORGANISM: Artificial Sequence
<220> FEATURE:
<223> OTHER INFORMATION: synthetic sequence, Bs-CspB variant 16

<400> SEQUENCE: 31

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Gln Val Glu
    50                  55                  60

Arg
65

<210> SEQ ID NO 32
<211> LENGTH: 67

<212> TYPE: PRT
<213> ORGANISM: Artificial Sequence
<220> FEATURE:
<223> OTHER INFORMATION: synthetic sequence, Bs-CspB variant 17

<400> SEQUENCE: 32

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Cys Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 33
<211> LENGTH: 67
<212> TYPE: PRT
<213> ORGANISM: Artificial Sequence
<220> FEATURE:
<223> OTHER INFORMATION: synthetic sequence, Bs-CspB variant 18

<400> SEQUENCE: 33

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Gly Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 34
<211> LENGTH: 204
<212> TYPE: DNA
<213> ORGANISM: Artificial Sequence
<220> FEATURE:
<223> OTHER INFORMATION: synthetic sequence, Bs-CspB variant 2

<400> SEQUENCE: 34

```
atggtagaag gtaaagtaaa atggttcaac gacagaaaag gttacggatt catcgaagta      60
gaaggtcaag acgatgtatt cgttcatttc tctgctattc aaggcgaagg cttcaaaact     120
ttagaagaag gccaagctgt ttcttttgaa atcgttgaag gaaaccgcgg accacaagct     180
gctaacgtta ctaaagaagc gtga                                            204
```

<210> SEQ ID NO 35
<211> LENGTH: 225
<212> TYPE: DNA
<213> ORGANISM: Artificial Sequence
<220> FEATURE:
<223> OTHER INFORMATION: synthetic sequence, Ec_CspD variant 2

<400> SEQUENCE: 35

```
atggaaaagg gtactgttaa gtggttcgac tccaagaaag ggtttggttt catctgccct      60
gaaggcggcg gcgaagatat tttcgctcat tattccacca tcagatgga tggttacaga     120
```

```
acgctaaaag ctggacaatc cgttcagttt gatgtccacc aggggccaaa aggcaatcac    180
gccagtgtta ttgtgcccgt cgaagtagaa gcggcagtcg catag                    225
```

<210> SEQ ID NO 36
<211> LENGTH: 204
<212> TYPE: DNA
<213> ORGANISM: Artificial Sequence
<220> FEATURE:
<223> OTHER INFORMATION: synthetic sequence, Bs-CspB variant 5

<400> SEQUENCE: 36

```
atggtagaag gtaaagtaaa atggttcaac tctgaaaaag gtttcggatt catcacgaag     60
gacgagggcg gcgatgtatt cgttcatttc tctgctattc aaggcgaagg cttcaaaact    120
ttagaagaag gccaagctgt ttcttttgaa atcgttgaag aaaccgcgg  accacaagct    180 gctaacgtta ctaaagaagc gtga                                           204
```

<210> SEQ ID NO 37
<211> LENGTH: 225
<212> TYPE: DNA
<213> ORGANISM: Artificial Sequence
<220> FEATURE:
<223> OTHER INFORMATION: synthetic sequence, Ec_CspD variant 5

<400> SEQUENCE: 37

```
atggaaaagg gtactgttaa gtggttcaac aatgccaaag ggtttggttt catctgccct     60
gaaggcggcg gcgaagatat tttcgctcat tattccacca ttcaaggcga aggtttcaaa    120
acgctaaaag ctggacaatc cgttcagttt gatgtccacc aggggccaaa aggcaatcac    180
gccagtgtta ttgtgcccgt cgaagtagaa gcggcagtcg catag                    225
```

<210> SEQ ID NO 38
<211> LENGTH: 204
<212> TYPE: DNA
<213> ORGANISM: Artificial Sequence
<220> FEATURE:
<223> OTHER INFORMATION: synthetic sequence, Ab_Csp2 variant 1

<400> SEQUENCE: 38

```
atggcaactg gcactgtaaa attcttcgct caggacaagg gctttggctt cattacccct     60
gacaatggcg gtcctgacgt attcgttcac atctcggcag tcggtttcgg cggctctctt    120
caggatggtc agaaggtgag ctacgagatt caggacggcc agaagaccgg taaatcgaaa    180
gccgagaacg tcactctcct ttag                                           204
```

<210> SEQ ID NO 39
<211> LENGTH: 201
<212> TYPE: DNA
<213> ORGANISM: Artificial Sequence
<220> FEATURE:
<223> OTHER INFORMATION: synthetic sequence, Tm_Csp1 variant 3

<400> SEQUENCE: 39

```
atgcgcggca aggtgaagtg gttcgactcc aagaagggct acggcttcat cacgaaggac     60
gagggcggcg atgtcttcgt gcactggagc gccatcgaga tggagggctt caagacgctc    120
aaggagggtc aagtggtcga gttcgagatt caagacggac agaaaggtcc gcaggccgcg    180
cacgtcaagg tcgtcgaatg a                                              201
```

<210> SEQ ID NO 40
<211> LENGTH: 204

```
<212> TYPE: DNA
<213> ORGANISM: Artificial Sequence
<220> FEATURE:
<223> OTHER INFORMATION: synthetic sequence, Bs-CspB variant 7

<400> SEQUENCE: 40
atggtagaag gtaaagtaaa atggttcaac tctgaaaaag gtttcggatt catcgaagta      60
gaaggtcaag acgatgtatt cgttcatttc tctgctattc aaggcgaagg cttcaaaact     120
ttagaagaag gccaagctgt ttcttttgaa atcgttgaag gaaaccgcgg accagcagct     180
gttaacgtta ctgctatcgc gtga                                            204

<210> SEQ ID NO 41
<211> LENGTH: 201
<212> TYPE: DNA
<213> ORGANISM: Artificial Sequence
<220> FEATURE:
<223> OTHER INFORMATION: synthetic sequence, Tt_Csp1 variant 1

<400> SEQUENCE: 41
atggtgcgcg gcaaggtgaa gtggttcaac gctgagaagg gctacggctt catcgagcgc      60
gaggacggca ccgacgtctt cgtgcactac tccgccatcg agatggaggg tttcaagacg     120
ctggaggagg gacaggccgt cgagttcgaa gtcgtccaag ccgcgaaggg tccacaggcg     180
agcaaggtcc ggaaactgtg a                                               201

<210> SEQ ID NO 42
<211> LENGTH: 210
<212> TYPE: DNA
<213> ORGANISM: Artificial Sequence
<220> FEATURE:
<223> OTHER INFORMATION: synthetic sequence, Ab_Csp2 variant 2

<400> SEQUENCE: 42
atggcaactg gcactgtaaa attcttcgct caggacaagg gctttggctt cattaccccct     60 gacaatggcg gtcctgacgt attcgttcac atctcggcag tcgagatgga gggcttcaag     120
acgcttcagg atggtcagaa ggtgagctac gagttgggac aagaccgcaa gaccggtaaa     180
tcgaaagccg agaacgtcac tctcctttag                                      210

<210> SEQ ID NO 43
<211> LENGTH: 204
<212> TYPE: DNA
<213> ORGANISM: Artificial Sequence
<220> FEATURE:
<223> OTHER INFORMATION: synthetic sequence, Bs-CspB variant 8

<400> SEQUENCE: 43
atggtagaag gtaaagtaaa atggttcaac tctgaaaaag gtttcggatt catcgaagta      60
gaaggtcaag acgatgtatt cgttcatttc tctgctattc aaggcgaagg cttcaaaact     120
ttagaagaag gccaagctgt ttcttttgaa atcgttgaag gaaaccgcgg accacaagct     180
atccaagtta tagaaccagc gtga                                            204

<210> SEQ ID NO 44
<211> LENGTH: 204
<212> TYPE: DNA
<213> ORGANISM: Artificial Sequence
<220> FEATURE:
<223> OTHER INFORMATION: synthetic sequence, Bs-CspB variant 9

<400> SEQUENCE: 44
```

```
atggtagaag gtaaagtaaa atggttcaac tctgaaaaag gtttcggatt catcgaagta      60
gaaggtcaag acgatgtatt cgttcatttc tctgctattc aaggcgaagg cttcaaaact     120
ttagaagaag gccaagctgt ttcttttgaa atcgttgaag gaaaccgcgg accacaagct     180
ggcaaagtta aaataaaagc gtga                                            204
```

```
<210> SEQ ID NO 45
<211> LENGTH: 270
<212> TYPE: DNA
<213> ORGANISM: Artificial Sequence
<220> FEATURE:
<223> OTHER INFORMATION: synthetic sequence, Bs-CspB variant 10

<400> SEQUENCE: 45
```

```
atggtagaag gtaaagtaaa atggttcaac tctgaaaaag gtttcggatt catcgaagta      60
gaaggtcaag acgatgtatt cgttcatttc tctgctattc aaggcgaagg cttcaaaact     120
ttagaagaag gccaagctgt ttcttttgaa atcgttgaag gaaaccgcgg accacaagct     180
atccaagtta taaaactagc aagctggcaa agttacaaaa ccagcgtgac tcgagcacca     240
ccaccaccac cactgagatc cggctgctaa                                       270
```

```
<210> SEQ ID NO 46
<211> LENGTH: 297
<212> TYPE: DNA
<213> ORGANISM: Artificial Sequence
<220> FEATURE:
<223> OTHER INFORMATION: synthetic sequence, Bs-CspB variant 11

<400> SEQUENCE: 46
```

```
atggtagaag gtaaagtaaa atggttcaac tctgaaaaag gtttcggatt catcgaagta      60
gaaggtcaag acgatgtatt cgttcatttc tctgctattc aaggcgaagg cttcaaaact     120
ttagaagaag gccaagctgt ttcttttgaa atcgttgaag gaaaccgcgg accacaagct     180
ggccaagttg taaccagcg tgactcgagc accaccacca ccaccactga gatccggctg     240
ctaacaaagc ccgaaaggaa gctgagttgg ctgctgccac cgctgagcaa taactag        297
```

```
<210> SEQ ID NO 47
<211> LENGTH: 246
<212> TYPE: DNA
<213> ORGANISM: Artificial Sequence
<220> FEATURE:
<223> OTHER INFORMATION: synthetic sequence, Bs-CspB variant 13

<400> SEQUENCE: 47
```

```
atggtagaag gtaaagtaaa atggttcaac tctgaaaaag gtttcggatt catcgaagta      60
gaaggtcaag acgatgtatt cgttcatttc tctgctattc aaggcgaagg cttcaaaact     120
ttagaagaag gccaagctgt ttcttttgaa atcgttgaag gaaaccgcgg accacaagct     180
gtccaagttt gtaatactag cgtgactcga gcaccaccac caccaccact gagatccggc     240
tgctaa                                                                246
```

```
<210> SEQ ID NO 48
<211> LENGTH: 204
<212> TYPE: DNA
<213> ORGANISM: Artificial Sequence
<220> FEATURE:
<223> OTHER INFORMATION: synthetic sequence, Bs-CspB variant 14

<400> SEQUENCE: 48
```

```
atggtagaag gtaaagtaaa atggttcaac tctgaaaaag gtttcggatt catcacaacg      60
```

```
gatggtgcaa acgatgtatt cgttcatttc tctgctattc aaggcgaagg cttcaaaact    120
ttagaagaag gccaagctgt ttcttttgaa atcgttgaag aaaccgcgg accacaagct     180 gctaacgtta ctaaagaagc gtga                                           204
```

<210> SEQ ID NO 49
<211> LENGTH: 204
<212> TYPE: DNA
<213> ORGANISM: Artificial Sequence
<220> FEATURE:
<223> OTHER INFORMATION: synthetic sequence, Bs-CspB variant 15

<400> SEQUENCE: 49

```
atggtagaag gtaaagtaaa atggttcaac tctgaaaaag gtttcggatt catcgaagta    60
gaaggtcaag acgatgtatt cgttcatttc tctgctattc aaggcgaagg cttcaaatcc    120
ttaaacgaag accaagctgt ttcttttgaa atcgttgaag aaaccgcgg accacaagct     180 gctaacgtta ctaaagaagc gtga                                           204
```

<210> SEQ ID NO 50
<211> LENGTH: 195
<212> TYPE: DNA
<213> ORGANISM: Artificial Sequence
<220> FEATURE:
<223> OTHER INFORMATION: synthetic sequence, Bs-CspB variant 16

<400> SEQUENCE: 50

```
atggtagaag gtaaagtaaa atggttcaac tctgaaaaag gtttcggatt catcgaagta    60
gaaggtcaag acgatgtatt cgttcatttc tctgctattc aaggcgaagg cttcaaaact    120
ttagaagaag gccaagctgt ttcttttgaa atcgttgaag aaaccgcgg accacaagct     180 gtccaagttg agtaa                                                     195
```

<210> SEQ ID NO 51
<211> LENGTH: 204
<212> TYPE: DNA
<213> ORGANISM: Artificial Sequence
<220> FEATURE:
<223> OTHER INFORMATION: synthetic sequence, Bs-CspB variant 17

<400> SEQUENCE: 51

```
atggtagaag gtaaagtaaa atggttcaac tctgaaaaag gtttcggatt catcgaagta    60
gaaggtcaag acgatgtatt cgttcatttc tgcgctattc aaggcgaagg cttcaaaact    120
ttagaagaag gccaagctgt ttcttttgaa atcgttgaag aaaccgcgg accacaagct     180 gctaacgtta ctaaagaagc gtga                                           204
```

<210> SEQ ID NO 52
<211> LENGTH: 204
<212> TYPE: DNA
<213> ORGANISM: Artificial Sequence
<220> FEATURE:
<223> OTHER INFORMATION: synthetic sequence, Bs-CspB variant 18

<400> SEQUENCE: 52

```
atggtagaag gtaaagtaaa atggttcaac tctgaaaaag gtttcggatt catcgaagta    60
gaaggtcaag acgatgtatt cgttcatttc ggggctattc aaggcgaagg cttcaaaact    120
ttagaagaag gccaagctgt ttcttttgaa atcgttgaag aaaccgcgg accacaagct     180 gctaacgtta ctaaagaagc gtga                                           204
```

<210> SEQ ID NO 53
<211> LENGTH: 67
<212> TYPE: PRT
<213> ORGANISM: Artificial Sequence
<220> FEATURE:
<223> OTHER INFORMATION: synthetic sequence, Bs_cspB-L2V-F30R

<400> SEQUENCE: 53

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Arg Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 54
<211> LENGTH: 67
<212> TYPE: PRT
<213> ORGANISM: Artificial Sequence
<220> FEATURE:
<223> OTHER INFORMATION: synthetic sequence, Bs_cspB-L2V-F15Y

<400> SEQUENCE: 54

```
Met Val Glu Gly Lys Val Lys Trp Phe Asn Ser Glu Lys Gly Tyr Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 55
<211> LENGTH: 67
<212> TYPE: PRT
<213> ORGANISM: Artificial Sequence
<220> FEATURE:
<223> OTHER INFORMATION: synthetic sequence, Bs_cspB-L2V-F15R

<400> SEQUENCE: 55

```
Met Val Glu Gly Lys Val Lys Trp Phe Asn Ser Glu Lys Gly Arg Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 56
<211> LENGTH: 67
<212> TYPE: PRT

<213> ORGANISM: Artificial Sequence
<220> FEATURE:
<223> OTHER INFORMATION: synthetic sequence, Bs_cspB-L2V-F30W

<400> SEQUENCE: 56

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Trp Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 57
<211> LENGTH: 67
<212> TYPE: PRT
<213> ORGANISM: Artificial Sequence
<220> FEATURE:
<223> OTHER INFORMATION: synthetic sequence, Bs_cspB-L2V-F15Y:F30W

<400> SEQUENCE: 57

```
Met Val Glu Gly Lys Val Lys Trp Phe Asn Ser Glu Lys Gly Tyr Gly
1               5                   10                  15

Phe Ile Glu Val Glu Gly Gln Asp Asp Val Phe Val His Trp Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 58
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 58

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Glu Ile Arg Gly Tyr Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 59
<211> LENGTH: 67
<212> TYPE: PRT
<213> ORGANISM: Artificial Sequence
<220> FEATURE:
<223> OTHER INFORMATION: synthetic sequence, Bs-CspB variant -continued

```
<400> SEQUENCE: 59

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Glu Ser Gly Gly Phe Arg Thr Leu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 60
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 60

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Ser Leu Ala Glu Tyr Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 61
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 61

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Ser Leu Gly Glu Asp Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 62
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 62

Met Val Glu Gly Lys Val Lys Trp Phe Asn Ser Glu Lys Gly Phe Gly
1               5                   10                  15
```

```
Phe Ile Glu Val Glu Gly Gln Asp Asp Val Phe Val His Phe Ser Ala
            20                  25                  30

Ile Gln Gly Glu Gly Phe Lys Ser Leu Gly Glu Ser Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 63
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 63

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Ser Glu Asp Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 64
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 64

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Thr Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 65
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 65

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30
```

Ile Gln Gly Glu Gly Phe Lys Thr Leu Asp Glu Asp Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 66
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 66

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Asp Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 67
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 67

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Ala Lys Gly Pro Gln Ala Ala Asn Val Thr
    50                  55                  60

Lys Glu Ala
65

<210> SEQ ID NO 68
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 68

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asp Lys Gly Pro Gln Ala Ala Asn Val Thr

Lys Glu Ala
65

<210> SEQ ID NO 69
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 69

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asp Arg Gly Pro Gln Ala Ala Asn Val Thr
        50                  55                  60

Lys Glu Ala
65

<210> SEQ ID NO 70
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 70

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Glu Lys Gly Pro Gln Ala Ala Asn Val Thr
        50                  55                  60

Lys Glu Ala
65

<210> SEQ ID NO 71
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 71

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly His Arg Gly Pro Gln Ala Ala Asn Val Thr
        50                  55                  60

Lys Glu Ala
65

<210> SEQ ID NO 72
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 72

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Lys Gly Pro Gln Ala Ala Asn Val Thr
    50                  55                  60

Lys Glu Ala
65

<210> SEQ ID NO 73
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 73

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Lys Leu Gln
    50                  55                  60

Lys Lys Arg
65

<210> SEQ ID NO 74
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 74

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 75
<211> LENGTH: 67

```
<212> TYPE: PRT
<213> ORGANISM: Artificial Sequence
<220> FEATURE:
<223> OTHER INFORMATION: synthetic sequence, Bs-CspB variant

<400> SEQUENCE: 75

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Lys Val Ala
    50                  55                  60

Lys Gln Ala
65

<210> SEQ ID NO 76
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 76

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Lys Val Glu
    50                  55                  60

Lys Leu Ala
65

<210> SEQ ID NO 77
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 77

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Asn Val Lys
    50                  55                  60

Ile Thr Ala
65

<210> SEQ ID NO 78
<211> LENGTH: 67
<212> TYPE: PRT
<213> ORGANISM: Artificial Sequence
<220> FEATURE:
<223> OTHER INFORMATION: synthetic sequence, Bs-CspB variant
```

<400> SEQUENCE: 78

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Asn Val Thr
    50                  55                  60

Ala Glu Ala
65

<210> SEQ ID NO 79
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 79

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Gln Val Lys
    50                  55                  60

Ala Thr Ala
65

<210> SEQ ID NO 80
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 80

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Gln Val Lys
    50                  55                  60

Thr Thr Ala
65

<210> SEQ ID NO 81
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 81

Met Val Glu Gly Lys Val Lys Trp Phe Asn Ser Glu Lys Gly Phe Gly

```
                1               5                  10                  15
            Phe Ile Glu Val Glu Gly Gln Asp Asp Val Phe Val His Phe Ser Ala
                            20                  25                  30

Ile Gln Gly Glu Gly Phe Lys Thr Leu Glu Glu Gly Gln Ala Val Ser
                        35                  40                  45

Phe Glu Ile Val Glu Gly Asn Arg Gly Pro Gln Ala Ile Gln Val Thr
                50                  55                  60

Thr Thr Ala
            65

<210> SEQ ID NO 82
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 82

Met Val Glu Gly Lys Val Lys Trp Phe Asn Ser Glu Lys Gly Phe Gly
            1               5                  10                  15

Phe Ile Glu Val Glu Gly Gln Asp Asp Val Phe Val His Phe Ser Ala
                            20                  25                  30

Ile Gln Gly Glu Gly Phe Lys Thr Leu Glu Glu Gly Gln Ala Val Ser
                        35                  40                  45

Phe Glu Ile Val Glu Gly Asn Arg Gly Pro Gln Ala Thr His Val Ile
                50                  55                  60

Ile Lys Ala
            65

<210> SEQ ID NO 83
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 83

Met Val Glu Gly Lys Val Lys Trp Phe Asn Ser Glu Lys Gly Phe Gly
            1               5                  10                  15

Phe Ile Glu Val Glu Gly Gln Asp Asp Val Phe Val His Phe Ser Ala
                            20                  25                  30

Ile Gln Gly Glu Gly Phe Lys Thr Leu Glu Glu Gly Gln Ala Val Ser
                        35                  40                  45

Phe Glu Ile Val Glu Gly Asn Arg Gly Pro Gln Ala Thr His Val Val
                50                  55                  60

Val Pro Ala
            65

<210> SEQ ID NO 84
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 84

Met Val Glu Gly Lys Val Lys Trp Phe Asn Ser Glu Lys Gly Phe Gly
            1               5                  10                  15

Phe Ile Glu Val Glu Gly Gln Asp Asp Val Phe Val His Phe Ser Ala
                            20                  25                  30
```

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Thr Asn Val Ala
 50                  55                  60

Lys Gln Ala
 65

<210> SEQ ID NO 85
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 85

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Thr Asn Val Ile
 50                  55                  60

Glu Val Ala
 65

<210> SEQ ID NO 86
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 86

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Thr Asn Val Ile
 50                  55                  60

Thr Ala Ala
 65

<210> SEQ ID NO 87
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 87

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Thr Asn Val Ile
            50                  55                  60

Val Val Ala
65

<210> SEQ ID NO 88
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 88

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Thr Gln Val Lys
            50                  55                  60

Ile Ile Ala
65

<210> SEQ ID NO 89
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 89

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val His Val Ile
            50                  55                  60

Ala Ala Ala
65

<210> SEQ ID NO 90
<211> LENGTH: 64
<212> TYPE: PRT
<213> ORGANISM: Artificial Sequence
<220> FEATURE:
<223> OTHER INFORMATION: synthetic sequence, Bs-CspB variant

<400> SEQUENCE: 90

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Lys Leu Lys
            50                  55                  60

<210> SEQ ID NO 91
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 91

```
Met Val Glu Gly Lys Val Lys Trp Phe Asn Ser Glu Lys Gly Phe Gly
1               5                   10                  15
Phe Ile Glu Val Glu Gly Gln Asp Asp Val Phe Val His Phe Ser Ala
                20                  25                  30
Ile Gln Gly Glu Gly Phe Lys Thr Leu Glu Glu Gly Gln Ala Val Ser
            35                  40                  45
Phe Glu Ile Val Glu Gly Asn Arg Gly Pro Gln Ala Val Lys Val Ala
        50                  55                  60
Ile Glu Ala
65
```

<210> SEQ ID NO 92
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 92

```
Met Val Glu Gly Lys Val Lys Trp Phe Asn Ser Glu Lys Gly Phe Gly
1               5                   10                  15
Phe Ile Glu Val Glu Gly Gln Asp Asp Val Phe Val His Phe Ser Ala
                20                  25                  30
Ile Gln Gly Glu Gly Phe Lys Thr Leu Glu Glu Gly Gln Ala Val Ser
            35                  40                  45
Phe Glu Ile Val Glu Gly Asn Arg Gly Pro Gln Ala Val Lys Val Val
        50                  55                  60
Ala Ile Ala
65
```

<210> SEQ ID NO 93
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 93

```
Met Val Glu Gly Lys Val Lys Trp Phe Asn Ser Glu Lys Gly Phe Gly
1               5                   10                  15
Phe Ile Glu Val Glu Gly Gln Asp Asp Val Phe Val His Phe Ser Ala
                20                  25                  30
Ile Gln Gly Glu Gly Phe Lys Thr Leu Glu Glu Gly Gln Ala Val Ser
            35                  40                  45
Phe Glu Ile Val Glu Gly Asn Arg Gly Pro Gln Ala Val Asn Val Ile
        50                  55                  60
Ile Ala Ala
65
```

<210> SEQ ID NO 94
<211> LENGTH: 67
<212> TYPE: PRT
<213> ORGANISM: Artificial Sequence -continued
<220> FEATURE:
<223> OTHER INFORMATION: synthetic sequence, Bs-CspB variant

<400> SEQUENCE: 94

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Asn Val Lys
    50                  55                  60

Ile Lys Ala
65

<210> SEQ ID NO 95
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 95

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Asn Val Lys
    50                  55                  60

Lys Ile Ala
65

<210> SEQ ID NO 96
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 96

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Gln Val Glu
    50                  55                  60

Ile Leu Ala
65

<210> SEQ ID NO 97
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 97

```
Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Val Gln Val Ile
    50                  55                  60

Lys Lys Ala
65

<210> SEQ ID NO 98
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 98

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Val Gln Val Lys
    50                  55                  60

Thr Ala Ala
65

<210> SEQ ID NO 99
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 99

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Pro Arg Gly Pro Gln Ala Ala Asn Val Thr
    50                  55                  60

Lys Glu Ala
65

<210> SEQ ID NO 100
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 100

Met Val Glu Gly Lys Val Lys Trp Phe Asn Ser Glu Lys Gly Phe Gly
1               5                   10                  15
```

```
Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Gln Lys Gly Pro Gln Ala Ala Asn Val Thr
    50                  55                  60

Lys Glu Ala
65

<210> SEQ ID NO 101
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 101

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Arg Lys Gly Pro Gln Ala Ala Asn Val Thr
    50                  55                  60

Lys Glu Ala
65

<210> SEQ ID NO 102
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 102

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Arg Lys Gly Pro Gln Ala Ala Asn Val Thr
    50                  55                  60

Lys Glu Ala
65

<210> SEQ ID NO 103
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 103

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
```

35                  40                  45

Phe Glu Ile Val Glu Gly Ser Arg Gly Pro Gln Ala Ala Asn Val Thr
        50                  55                  60

Lys Glu Ala
 65

<210> SEQ ID NO 104
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 104

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Thr Arg Gly Pro Gln Ala Ala Asn Val Thr
        50                  55                  60

Lys Glu Ala
 65

<210> SEQ ID NO 105
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 105

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Asn Val Val Pro Gly Asn Arg Gly Pro Gln Ala Ala Asn Val Thr
        50                  55                  60

Lys Glu Ala
 65

<210> SEQ ID NO 106
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 106

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Thr Ile Gln Gln Gly Asn Arg Gly Pro Gln Ala Ala Asn Val Thr
        50                  55                  60

Lys Glu Ala
65

<210> SEQ ID NO 107
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 107

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Ser Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 108
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 108

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Gly Glu Asn Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 109
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 109

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Asn Glu Asp Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 110
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 110

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Ser Glu Asp Gln Ala Val Ser
            35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 111
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 111

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Thr Glu Asp Gln Ala Val Ser
            35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 112
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 112

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Arg Glu Gly Tyr Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 113
<211> LENGTH: 67
<212> TYPE: PRT

<213> ORGANISM: Artificial Sequence
<220> FEATURE:
<223> OTHER INFORMATION: synthetic sequence, Bs-CspB variant

<400> SEQUENCE: 113

```
Met Val Glu Gly Lys Val Lys Trp Phe Asn Ser Glu Lys Gly Phe Gly
1               5                   10                  15

Phe Ile Glu Val Glu Gly Gln Thr Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65
```

<210> SEQ ID NO 114
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 114

```
Met Val Glu Gly Lys Val Lys Trp Phe Asn Ser Glu Lys Gly Tyr Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65
```

<210> SEQ ID NO 115
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 115

```
Met Val Glu Gly Lys Val Lys Trp Phe Asp Thr Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65
```

<210> SEQ ID NO 116
<211> LENGTH: 67
<212> TYPE: PRT
<213> ORGANISM: Artificial Sequence
<220> FEATURE:
<223> OTHER INFORMATION: synthetic sequence, Bs-CspB variant

```
<400> SEQUENCE: 116

Met Val Glu Gly Lys Val Lys Trp Phe Asn Asp Ser Lys Gly Tyr Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 117
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 117

Met Val Glu Gly Lys Val Lys Trp Phe Asn Ser Glu Lys Gly Phe Gly
 1               5                  10                  15

Phe Ile Ala Met Asp Gly Pro Thr Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 118
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 118

Met Val Glu Gly Lys Val Lys Trp Phe Asn Ser Glu Lys Gly Phe Gly
 1               5                  10                  15

Phe Ile Ala Met Asp Gly Pro Thr Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 119
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 119

Met Val Glu Gly Lys Val Lys Trp Phe Asn Ser Glu Lys Gly Phe Gly
 1               5                  10                  15
```

```
Phe Ile Glu Ala Ala Gly Lys Asn Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 120
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 120

Met Val Glu Gly Lys Val Lys Trp Phe Asn Ser Glu Lys Gly Phe Gly
1               5                   10                  15

Phe Ile Glu Ala Asp Gly Thr Thr Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 121
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 121

Met Val Glu Gly Lys Val Lys Trp Phe Asn Ser Glu Lys Gly Phe Gly
1               5                   10                  15

Phe Ile Glu Ala Asp Gly Thr Thr Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 122
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 122

Met Val Glu Gly Lys Val Lys Trp Phe Asn Ser Glu Lys Gly Phe Gly
1               5                   10                  15

Phe Ile Glu Leu Asp Gly Pro Ala Asp Val Phe Val His Phe Ser Ala
            20                  25                  30
```

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 123
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 123

Met Val Glu Gly Lys Val Lys Trp Phe Asn Ser Glu Lys Gly Phe Gly
1               5                   10                  15

Phe Ile Glu Leu Asp Gly Pro Ala Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 124
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 124

Met Val Glu Gly Lys Val Lys Trp Phe Asn Ser Glu Lys Gly Phe Gly
1               5                   10                  15

Phe Ile Glu Met Glu Gly Gln Thr Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 125
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 125

Met Val Glu Gly Lys Val Lys Trp Phe Asn Ser Glu Lys Gly Phe Gly
1               5                   10                  15

Phe Ile Glu Met Glu Gly Gln Thr Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr

<210> SEQ ID NO 126
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 126

Met Val Glu Gly Lys Val Lys Trp Phe Asn Ser Glu Lys Gly Phe Gly
1               5                   10                  15

Phe Ile Glu Gln Glu Gly Arg Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 127
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 127

Met Val Glu Gly Lys Val Lys Trp Phe Asn Ser Glu Lys Gly Phe Gly
1               5                   10                  15

Phe Ile Glu Gln Glu Gly Arg Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 128
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 128

Met Val Glu Gly Lys Val Lys Trp Phe Asn Ser Glu Lys Gly Phe Gly
1               5                   10                  15

Phe Ile Glu Thr Asp Gly Ala Glu Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 129
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 129

Met Val Glu Gly Lys Val Lys Trp Phe Asn Ser Glu Lys Gly Phe Gly
1               5                   10                  15

Phe Ile Glu Thr Asp Gly Ala Glu Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 130
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 130

Met Val Glu Gly Lys Val Lys Trp Phe Asn Ser Glu Lys Gly Phe Gly
1               5                   10                  15

Phe Ile Glu Val Ala Gly Lys Ser Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 131
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 131

Met Val Glu Gly Lys Val Lys Trp Phe Asn Ser Glu Lys Gly Phe Gly
1               5                   10                  15

Phe Ile Pro Arg Glu Gly Ala Glu Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 132
<211> LENGTH: 67

```
<212> TYPE: PRT
<213> ORGANISM: Artificial Sequence
<220> FEATURE:
<223> OTHER INFORMATION: synthetic sequence, Bs-CspB variant

<400> SEQUENCE: 132

Met Val Glu Gly Lys Val Lys Trp Phe Asn Ser Glu Lys Gly Phe Gly
1               5                  10                  15

Phe Ile Gln Glu Asp Gly Ala Gly Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
50                  55                  60

Lys Glu Ala
65

<210> SEQ ID NO 133
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 133

Met Val Glu Gly Lys Val Lys Trp Phe Asn Ser Glu Lys Gly Phe Gly
1               5                  10                  15

Phe Ile Gln Glu Asp Gly Ala Gly Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
50                  55                  60

Lys Glu Ala
65

<210> SEQ ID NO 134
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 134

Met Val Glu Gly Lys Val Lys Trp Phe Asn Ser Glu Lys Gly Phe Gly
1               5                  10                  15

Phe Ile Gln Gly Asp Gly Glu Ser Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
50                  55                  60

Lys Glu Ala
65

<210> SEQ ID NO 135
<211> LENGTH: 67
<212> TYPE: PRT
<213> ORGANISM: Artificial Sequence
<220> FEATURE:
<223> OTHER INFORMATION: synthetic sequence, Bs-CspB variant
```

<400> SEQUENCE: 135

Met Val Glu Gly Lys Val Lys Trp Phe Asn Ser Glu Lys Gly Phe Gly
1               5                   10                  15

Phe Ile Gln Gly Asp Gly Glu Ser Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 136
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 136

Met Val Glu Gly Lys Val Lys Trp Phe Asn Ser Glu Lys Gly Phe Gly
1               5                   10                  15

Phe Ile Gln Gln Asp Gly Pro Glu Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 137
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 137

Met Val Glu Gly Lys Val Lys Trp Phe Asn Ser Glu Lys Gly Phe Gly
1               5                   10                  15

Phe Ile Gln Arg Glu Gly Gly Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 138
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 138

Met Val Glu Gly Lys Val Lys Trp Phe Asn Ser Glu Lys Gly Phe Gly

```
                1               5                  10                  15
            Phe Ile Gln Arg Glu Gly Gly Gly Asp Val Phe Val His Phe Ser Ala
                            20                  25                  30

Ile Gln Gly Glu Gly Phe Lys Thr Leu Glu Glu Gly Gln Ala Val Ser
                        35                  40                  45

Phe Glu Ile Val Glu Gly Asn Arg Gly Pro Gln Ala Ala Asn Val Thr
                    50                  55                  60

Lys Glu Ala
            65
```

<210> SEQ ID NO 139
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 139

```
            Met Val Glu Gly Lys Val Lys Trp Phe Asn Ser Glu Lys Gly Phe Gly
            1               5                  10                  15

Phe Ile Gln Arg Glu Gly Gly Gly Asp Val Phe Val His Phe Ser Ala
                            20                  25                  30

Ile Gln Gly Glu Gly Phe Lys Thr Leu Glu Glu Gly Gln Ala Val Ser
                        35                  40                  45

Phe Glu Ile Val Glu Gly Asn Arg Gly Pro Gln Ala Ala Asn Val Thr
                    50                  55                  60

Lys Glu Ala
            65
```

<210> SEQ ID NO 140
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 140

```
            Met Val Glu Gly Lys Val Lys Trp Phe Asn Ser Glu Lys Gly Phe Gly
            1               5                  10                  15

Phe Ile Gln Thr Ala Gly Gly Asp Asp Val Phe Val His Phe Ser Ala
                            20                  25                  30

Ile Gln Gly Glu Gly Phe Lys Thr Leu Glu Glu Gly Gln Ala Val Ser
                        35                  40                  45

Phe Glu Ile Val Glu Gly Asn Arg Gly Pro Gln Ala Ala Asn Val Thr
                    50                  55                  60

Lys Glu Ala
            65
```

<210> SEQ ID NO 141
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 141

```
            Met Val Glu Gly Lys Val Lys Trp Phe Asn Ser Glu Lys Gly Phe Gly
            1               5                  10                  15

Phe Ile Gln Thr Glu Gly Thr Glu Asp Val Phe Val His Phe Ser Ala
                            20                  25                  30
```

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 142
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 142

Met Val Glu Gly Lys Val Lys Trp Phe Asn Ser Glu Lys Gly Phe Gly
1               5                   10                  15

Phe Ile Gln Thr Glu Gly Thr Glu Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 143
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 143

Met Val Glu Gly Lys Val Lys Trp Phe Asn Ser Glu Lys Gly Phe Gly
1               5                   10                  15

Phe Ile Gln Val Ala Gly Thr Thr Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 144
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 144

Met Val Glu Gly Lys Val Lys Trp Phe Asn Ser Glu Lys Gly Phe Gly
1               5                   10                  15

Phe Ile Gln Val Ala Gly Thr Thr Asp Val Phe Val His Phe Ser Ala
            20                  25                  30

Ile Gln Gly Glu Gly Phe Lys Thr Leu Glu Glu Gly Gln Ala Val Ser
            35                  40                  45

```
Phe Glu Ile Val Glu Gly Asn Arg Gly Pro Gln Ala Ala Asn Val Thr
    50                  55                  60

Lys Glu Ala
65

<210> SEQ ID NO 145
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 145

Met Val Glu Gly Lys Val Lys Trp Phe Asn Ser Glu Lys Gly Phe Gly
1               5                   10                  15

Phe Ile Thr Thr Asp Gly Ala Asn Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 146
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 146

Met Val Glu Gly Lys Val Lys Trp Phe Thr Ala Asp Lys Gly Tyr Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 147
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 147

Met Val Glu Gly Lys Val Lys Trp Phe Thr Asp Lys Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
```

<210> SEQ ID NO 148
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 148

Met Val Glu Gly Lys Val Lys Trp Phe Thr Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 149
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 149

Met Val Glu Gly Lys Val Lys Trp Phe Thr Ser Glu Lys Gly Tyr Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 150
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 150

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Glu Ala Ser Gly Tyr Arg Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 151

```
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 151

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Glu Gly Asn Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 152
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 152

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Glu Gly Asn Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 153
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 153

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Glu Gly Ser Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 154
<211> LENGTH: 67
<212> TYPE: PRT
<213> ORGANISM: Artificial Sequence
<220> FEATURE:
```

<223> OTHER INFORMATION: synthetic sequence, Bs-CspB variant

<400> SEQUENCE: 154

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Glu Gly Ser Gly Tyr Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 155
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 155

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Glu Lys Asp Gly Tyr Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 156
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 156

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Glu Lys Ser Gly Phe Arg Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 157
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 157

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Glu Lys Ser Gly Phe Arg Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 158
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 158

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Glu Asn Glu Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 159
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 159

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Glu Asn Gly Gly Phe Arg Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 160
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 160

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala

```
                 20                  25                  30

Ile Glu Asn Gly Gly Phe Arg Thr Leu Glu Glu Gly Gln Ala Val Ser
             35                  40                  45

Phe Glu Ile Val Glu Gly Asn Arg Gly Pro Gln Ala Ala Asn Val Thr
         50                  55                  60

Lys Glu Ala
 65

<210> SEQ ID NO 161
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 161

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
             20                  25                  30

Ile Gln Ala Glu Gly Tyr Arg Thr Leu Glu Glu Gly Gln Ala Val Ser
             35                  40                  45

Phe Glu Ile Val Glu Gly Asn Arg Gly Pro Gln Ala Ala Asn Val Thr
         50                  55                  60

Lys Glu Ala
 65

<210> SEQ ID NO 162
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 162

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
             20                  25                  30

Ile Gln Ala Glu Gly Tyr Arg Thr Leu Glu Glu Gly Gln Ala Val Ser
             35                  40                  45

Phe Glu Ile Val Glu Gly Asn Arg Gly Pro Gln Ala Ala Asn Val Thr
         50                  55                  60

Lys Glu Ala
 65

<210> SEQ ID NO 163
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 163

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
             20                  25                  30

Ile Gln Ala Gly Gly Phe Lys Thr Leu Glu Glu Gly Gln Ala Val Ser
             35                  40                  45
```

-continued

Phe Glu Ile Val Glu Gly Asn Arg Gly Pro Gln Ala Ala Asn Val Thr
            50                  55                  60

Lys Glu Ala
65

<210> SEQ ID NO 164
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 164

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Ala Gly Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 165
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 165

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Ala Gly Gly Phe Arg Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 166
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 166

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Ala Ser Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 167
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 167

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Ala Ser Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 168
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 168

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Ala Ser Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 169
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 169

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Asp Asn Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

-continued

<210> SEQ ID NO 170
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 170

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Asp Asn Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 171
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 171

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Asp Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 172
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 172

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Asp Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 173
<211> LENGTH: 67
<212> TYPE: PRT
<213> ORGANISM: Artificial Sequence

```
<220> FEATURE:
<223> OTHER INFORMATION: synthetic sequence, Bs-CspB variant

<400> SEQUENCE: 173

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Ala Glu Ser Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 174
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 174

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Thr Glu Asp Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 175
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 175

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Thr Glu Ser Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 176
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 176
```

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
            20                  25                  30

Ile Gln Gly Glu Gly Phe Lys Ser Leu Thr Glu Ser Gln Ala Val Ser
        35                  40                  45

Phe Glu Ile Val Glu Gly Asn Arg Gly Pro Gln Ala Ala Asn Val Thr
        50                  55                  60

Lys Glu Ala
65

<210> SEQ ID NO 177
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 177

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
            20                  25                  30

Ile Gln Gly Glu Gly Phe Lys Thr Leu Ala Glu Asn Gln Ala Val Ser
        35                  40                  45

Phe Glu Ile Val Glu Gly Asn Arg Gly Pro Gln Ala Ala Asn Val Thr
        50                  55                  60

Lys Glu Ala
65

<210> SEQ ID NO 178
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 178

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Ala Arg Gly Pro Gln Ala Ala Asn Val Thr
        50                  55                  60

Lys Glu Ala
65

<210> SEQ ID NO 179
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 179

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Lys Lys Gly Pro Gln Ala Ala Asn Val Thr
    50                  55                  60

Lys Glu Ala
65

<210> SEQ ID NO 180
<211> LENGTH: 70
<212> TYPE: PRT
<213> ORGANISM: Artificial Sequence
<220> FEATURE:
<223> OTHER INFORMATION: synthetic sequence, Bs-CspB variant

<400> SEQUENCE: 180

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Pro Lys Gly Pro Lys Gly Pro Gln Ala Ala
    50                  55                  60

Asn Val Thr Lys Glu Ala
65                  70

<210> SEQ ID NO 181
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 181

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Arg Arg Gly Pro Gln Ala Ala Asn Val Thr
    50                  55                  60

Lys Glu Ala
65

<210> SEQ ID NO 182
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 182

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser

```
                   35                  40                  45

Phe Glu Ile Val Glu Gly Thr Lys Gly Pro Gln Ala Ala Asn Val Thr
    50                  55                  60

Lys Glu Ala
65

<210> SEQ ID NO 183
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 183

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Gly Gly Phe Arg Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 184
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 184

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Gly Gly Phe Arg Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 185
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 185

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Asn Gly Phe Arg Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60
```

Lys Glu Ala
65

<210> SEQ ID NO 186
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 186

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Ile Glu Gly Phe Arg Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 187
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 187

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Ile Asn Gly Tyr Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 188
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 188

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Ile Ser Gly Tyr Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 189
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 189

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Lys Asp Gly Tyr Arg Thr Leu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 190
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 190

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Lys Asp Gly Tyr Arg Thr Leu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 191
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 191

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Lys Gly Gly Phe Arg Thr Leu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 192
<211> LENGTH: 67
<212> TYPE: PRT

```
<213> ORGANISM: Artificial Sequence
<220> FEATURE:
<223> OTHER INFORMATION: synthetic sequence, Bs-CspB variant

<400> SEQUENCE: 192

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Lys Ser Gly Tyr Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 193
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 193

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Lys Ser Gly Tyr Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 194
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 194

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Met Lys Gly Phe Lys Thr Leu Glu Glu Gly Gln Ala Val Ser
            35                  40                  45

Phe Glu Asn Val Glu Gly Asn Arg Gly Pro Gln Ala Ala Asn Val Thr
        50                  55                  60

Lys Glu Ala
65

<210> SEQ ID NO 195
<211> LENGTH: 67
<212> TYPE: PRT
<213> ORGANISM: Artificial Sequence
<220> FEATURE:
<223> OTHER INFORMATION: synthetic sequence, Bs-CspB variant
```

```
<400> SEQUENCE: 195

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Asn Asp Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 196
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 196

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Asn Gly Gly Phe Arg Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 197
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 197

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Asn Gly Gly Phe Arg Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 198
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 198

Met Val Glu Gly Lys Val Lys Trp Phe Asn Ser Glu Lys Gly Phe Gly
1               5                   10                  15
```

-continued

Phe Ile Glu Val Glu Gly Gln Asp Asp Val Phe Val His Phe Ser Ala
            20                  25                  30

Ile Gln Asn Lys Gly Tyr Arg Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 199
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 199

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Asn Asn Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 200
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 200

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Asn Asn Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 201
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 201

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Asn Ser Gly Tyr Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 202
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 202

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Asn Ser Gly Tyr Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 203
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 203

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Asn Ser Gly Tyr Arg Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 204
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 204

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Asn Ser Gly Tyr Arg Thr Leu Glu Glu Gly Gln Ala Val Ser
            35                  40                  45

Phe Glu Ile Val Glu Gly Asn Arg Gly Pro Gln Ala Ala Asn Val Thr

Lys Glu Ala
65

<210> SEQ ID NO 205
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 205

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Arg Asp Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 206
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 206

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Arg Glu Gly Tyr Arg Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 207
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 207

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Thr Asn Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 208
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 208

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Thr Ser Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 209
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 209

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Thr Ser Gly Tyr Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 210
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 210

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Val Gly Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 211
<211> LENGTH: 67

<212> TYPE: PRT
<213> ORGANISM: Artificial Sequence
<220> FEATURE:
<223> OTHER INFORMATION: synthetic sequence, Bs-CspB variant

<400> SEQUENCE: 211

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Val Gly Gly Phe Arg Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 212
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 212

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Val Asn Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 213
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 213

Met Val Glu Gly Lys Val Lys Trp Phe Ala Ala Gly Lys Gly Tyr Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 214
<211> LENGTH: 67
<212> TYPE: PRT
<213> ORGANISM: Artificial Sequence
<220> FEATURE:
<223> OTHER INFORMATION: synthetic sequence, Bs-CspB variant -continued

<400> SEQUENCE: 214

Met Val Glu Gly Lys Val Lys Trp Phe Asn Asp Asn Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 215
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 215

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Glu Thr Ser Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 216
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 216

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Gly Glu Asn Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 217
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 217

Met Val Glu Gly Lys Val Lys Trp Phe Asn Ser Glu Lys Gly Phe Gly

```
                1               5                  10                  15
            Phe Ile Glu Val Glu Gly Gln Asp Asp Val Phe Val His Phe Ser Ala
                         20                  25                  30

Ile Gln Gly Glu Gly Phe Lys Ser Leu Ser Glu Asn Gln Ala Val Ser
                         35                  40                  45

Phe Glu Ile Val Glu Gly Asn Arg Gly Pro Gln Ala Ala Asn Val Thr
                         50                  55                  60

Lys Glu Ala
             65

<210> SEQ ID NO 218
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 218

Met Val Glu Gly Lys Val Lys Trp Phe Asn Ser Glu Lys Gly Phe Gly
             1               5                  10                  15

Phe Ile Glu Val Glu Gly Gln Asp Asp Val Phe Val His Phe Ser Ala
                         20                  25                  30

Ile Gln Gly Glu Gly Phe Lys Thr Leu Ala Glu Asp Gln Ala Val Ser
                         35                  40                  45

Phe Glu Ile Val Glu Gly Asn Arg Gly Pro Gln Ala Ala Asn Val Thr
                         50                  55                  60

Lys Glu Ala
             65

<210> SEQ ID NO 219
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 219

Met Val Glu Gly Lys Val Lys Trp Phe Asn Ser Glu Lys Gly Phe Gly
             1               5                  10                  15

Phe Ile Glu Val Glu Gly Gln Asp Asp Val Phe Val His Phe Ser Ala
                         20                  25                  30

Ile Gln Gly Glu Gly Phe Lys Thr Leu Glu Glu Asp Gln Ala Val Ser
                         35                  40                  45

Phe Glu Ile Val Glu Gly Asn Arg Gly Pro Gln Ala Ala Asn Val Thr
                         50                  55                  60

Lys Glu Ala
             65

<210> SEQ ID NO 220
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 220

Met Val Glu Gly Lys Val Lys Trp Phe Asn Ser Glu Lys Gly Phe Gly
             1               5                  10                  15

Phe Ile Glu Val Glu Gly Gln Asp Asp Val Phe Val His Phe Ser Ala
                         20                  25                  30
```

```
Ile Gln Gly Glu Gly Phe Lys Thr Leu Glu Glu Gly Gln Ala Val Ser
        35                  40                  45

Phe Glu Ile Val Glu Gly Ala Arg Gly Pro Gln Ala Ala Asn Val Thr
50                  55                  60

Lys Glu Ala
65

<210> SEQ ID NO 221
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 221

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
        35                  40                  45

Phe Glu Ile Val Glu Gly Ala Arg Gly Pro Gln Ala Ala Asn Val Thr
50                  55                  60

Lys Glu Ala
65

<210> SEQ ID NO 222
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 222

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
        35                  40                  45

Phe Glu Ile Val Glu Gly Asn Cys Gly Pro Gln Ala Ser Asn Val Pro
50                  55                  60

Ala Thr Ala
65

<210> SEQ ID NO 223
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 223

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
        35                  40                  45
```

Phe Glu Ile Val Glu Gly Asn Arg Gly Pro Gln Ala Ala His Val Glu
            50                  55                  60

Glu Thr Ala
65

<210> SEQ ID NO 224
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 224

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Gln Val Ala
    50                  55                  60

Thr Thr Ala
65

<210> SEQ ID NO 225
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 225

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Gln Val Glu
    50                  55                  60

Lys Lys Ala
65

<210> SEQ ID NO 226
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 226

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Gln Val Thr
    50                  55                  60

Lys Glu Ala

<210> SEQ ID NO 227
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 227

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Gly His Val Val
    50                  55                  60

Ile Lys Ala
65

<210> SEQ ID NO 228
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 228

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Gly Lys Val Glu
    50                  55                  60

Glu Lys Ala
65

<210> SEQ ID NO 229
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 229

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Gly Lys Val Glu
    50                  55                  60

Thr Lys Ala
65

<210> SEQ ID NO 230

<211> LENGTH: 70
<212> TYPE: PRT
<213> ORGANISM: Artificial Sequence
<220> FEATURE:
<223> OTHER INFORMATION: synthetic sequence, Bs-CspB variant

<400> SEQUENCE: 230

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Gly Gln Ala Ile
    50                  55                  60

Lys Val Glu Glu Thr Ala
65                  70

<210> SEQ ID NO 231
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 231

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile His Val Ile
    50                  55                  60

Lys Lys Ala
65

<210> SEQ ID NO 232
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 232

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile His Val Val
    50                  55                  60

Thr Lys Ala
65

<210> SEQ ID NO 233
<211> LENGTH: 67
<212> TYPE: PRT
<213> ORGANISM: Artificial Sequence
<220> FEATURE:

<223> OTHER INFORMATION: synthetic sequence, Bs-CspB variant

<400> SEQUENCE: 233

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Lys Val Lys
    50                  55                  60

Lys Ile Ala
65

<210> SEQ ID NO 234
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 234

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Asn Val Ala
    50                  55                  60

Glu Gln Ala
65

<210> SEQ ID NO 235
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 235

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Asn Val Ile
    50                  55                  60

Glu Pro Ala
65

<210> SEQ ID NO 236
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 236

-continued

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Asn Val Lys
    50                  55                  60

Glu Lys Ala
65

<210> SEQ ID NO 237
<211> LENGTH: 68
<212> TYPE: PRT
<213> ORGANISM: Artificial Sequence
<220> FEATURE:
<223> OTHER INFORMATION: synthetic sequence, Bs-CspB variant

<400> SEQUENCE: 237

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Asn Val Lys
    50                  55                  60

Lys Gln Ala Leu
65

<210> SEQ ID NO 238
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 238

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Gln Val Lys
    50                  55                  60

Glu Lys Ala
65

<210> SEQ ID NO 239
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 239

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala

```
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Gln Val Val
    50                  55                  60

Glu Gln Ala
65

<210> SEQ ID NO 240
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 240

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ser Lys Val Ile
    50                  55                  60

Glu Glu Ala
65

<210> SEQ ID NO 241
<211> LENGTH: 68
<212> TYPE: PRT
<213> ORGANISM: Artificial Sequence
<220> FEATURE:
<223> OTHER INFORMATION: synthetic sequence, Bs-CspB variant

<400> SEQUENCE: 241

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ser Gln Arg Cys
    50                  55                  60

Lys Arg Ser Val
65

<210> SEQ ID NO 242
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 242

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45
```

-continued

Phe Glu Ile Val Glu Gly Asn Arg Gly Pro Gln Ala Thr His Val Thr
    50                  55                  60

Ile Lys Ala
65

<210> SEQ ID NO 243
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 243

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Thr Gln Val Lys
    50                  55                  60

Glu Thr Ala
65

<210> SEQ ID NO 244
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 244

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val His Val Ile
    50                  55                  60

Ala Leu Ala
65

<210> SEQ ID NO 245
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 245

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val His Val Ile
    50                  55                  60

```
Ile Pro Ala
            65

<210> SEQ ID NO 246
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 246

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Lys Val Ile
    50                  55                  60

Asn Lys Arg
65

<210> SEQ ID NO 247
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 247

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Arg Arg Gly Pro Gln Ala Ala Asn Val Thr
    50                  55                  60

Lys Glu Ala
65

<210> SEQ ID NO 248
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 248

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Thr Lys Gly Pro Gln Ala Ala Asn Val Thr
    50                  55                  60

Lys Glu Ala
65
```

```
<210> SEQ ID NO 249
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 249
```

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Asn Leu Val Ser Gly Asn Arg Gly Pro Gln Ala Ala Asn Val Thr
    50                  55                  60

Lys Glu Ala
65

```
<210> SEQ ID NO 250
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 250
```

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Ser Leu Val Gln Gly Asn Arg Gly Pro Gln Ala Ala Asn Val Thr
    50                  55                  60

Lys Glu Ala
65

```
<210> SEQ ID NO 251
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 251
```

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Thr Leu Gln Pro Gly Asn Arg Gly Pro Gln Ala Ala Asn Val Thr
    50                  55                  60

Lys Glu Ala
65

```
<210> SEQ ID NO 252
<211> LENGTH: 67
<212> TYPE: PRT
<213> ORGANISM: Artificial Sequence
```

<220> FEATURE:
<223> OTHER INFORMATION: synthetic sequence, Bs-CspB variant

<400> SEQUENCE: 252

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Thr Val Val Ser Gly Asn Arg Gly Pro Gln Ala Ala Asn Val Thr
        50                  55                  60

Lys Glu Ala
65

<210> SEQ ID NO 253
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 253

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Gly Asn Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 254
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 254

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Lys Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 255
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 255

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
                20                  25                  30

Ile Gln Gly Glu Gly Phe Lys Thr Leu Lys Glu Asn Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 256
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 256

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
                20                  25                  30

Ile Gln Gly Glu Gly Phe Lys Thr Leu Lys Glu Ser Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 257
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 257

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
                20                  25                  30

Ile Gln Gly Glu Gly Phe Lys Thr Leu Asn Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 258
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 258

Met Val Glu Gly Lys Val Lys Trp Phe Asn Ser Glu Lys Gly Phe Gly
1               5                   10                  15

-continued

Phe Ile Glu Val Glu Gly Gln Asp Asp Val Phe Val His Phe Ser Ala
            20                  25                  30

Ile Gln Gly Glu Gly Phe Lys Thr Leu Asn Glu Asn Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 259
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 259

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Arg Glu Asn Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 260
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 260

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Thr Glu Asn Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 261
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 261

Met Val Glu Gly Lys Val Lys Trp Phe Asn Ser Glu Lys Gly Phe Gly
1               5                   10                  15

Phe Ile Glu Val Glu Gly Gln Glu Asp Val Phe Val His Phe Ser Ala
            20                  25                  30

Ile Gln Gly Glu Gly Phe Lys Thr Leu Glu Glu Gly Gln Ala Val Ser

```
                35                  40                  45

Phe Glu Ile Val Glu Gly Asn Arg Gly Pro Gln Ala Ala Asn Val Thr
 50                  55                  60

Lys Glu Ala
 65

<210> SEQ ID NO 262
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 262

Met Val Glu Gly Lys Val Lys Trp Phe Asn Ser Glu Lys Gly Phe Gly
  1               5                  10                  15

Phe Ile Thr Leu Asp Gly Lys Lys Asp Val Phe Val His Phe Ser Ala
                 20                  25                  30

Ile Gln Gly Glu Gly Phe Lys Thr Leu Glu Glu Gly Gln Ala Val Ser
             35                  40                  45

Phe Glu Ile Val Glu Gly Asn Arg Gly Pro Gln Ala Ala Asn Val Thr
 50                  55                  60

Lys Glu Ala
 65

<210> SEQ ID NO 263
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 263

Met Val Glu Gly Lys Val Lys Trp Phe Asn Thr Glu Lys Gly Phe Gly
  1               5                  10                  15

Phe Ile Glu Val Glu Gly Gln Asp Asp Val Phe Val His Phe Ser Ala
                 20                  25                  30

Ile Gln Gly Glu Gly Phe Lys Thr Leu Glu Glu Gly Gln Ala Val Ser
             35                  40                  45

Phe Glu Ile Val Glu Gly Asn Arg Gly Pro Gln Ala Ala Asn Val Thr
 50                  55                  60

Lys Glu Ala
 65

<210> SEQ ID NO 264
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 264

Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
                 20                  25                  30

Ile Gln Gly Glu Gly Phe Lys Ser Leu Asn Glu Ser Gln Ala Val Ser
             35                  40                  45

Phe Glu Ile Val Glu Gly Asn Arg Gly Pro Gln Ala Ala Asn Val Thr
 50                  55                  60
```

Lys Glu Ala
65

<210> SEQ ID NO 265
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 265

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Ala Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 266
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 266

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly His Lys Gly Pro Gln Ala Ala Asn Val Thr
    50                  55                  60

Lys Glu Ala
65

<210> SEQ ID NO 267
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 267

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Arg Lys Gly Pro Gln Ala Ala Asn Val Thr
    50                  55                  60

Lys Glu Ala
65

<210> SEQ ID NO 268
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 268

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Gly Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 269
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 269

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Ser Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 270
<211> LENGTH: 67
<212> TYPE: PRT
<213> ORGANISM: Artificial Sequence
<220> FEATURE:
<223> OTHER INFORMATION: synthetic sequence, Bs_CspB_G22A_D24A_E3A-K5A

<400> SEQUENCE: 270

```
Met Val Ala Gly Ala Val Lys Trp Phe Asn Ser Glu Lys Gly Phe Gly
1               5                   10                  15

Phe Ile Glu Val Glu Ala Gln Ala Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 271
<211> LENGTH: 67
<212> TYPE: PRT

<213> ORGANISM: Artificial Sequence
<220> FEATURE:
<223> OTHER INFORMATION: synthetic sequence, Bs_CspB_G22A_D24A_G57A-Q59A

<400> SEQUENCE: 271

```
Met Val Glu Gly Lys Val Lys Trp Phe Asn Ser Glu Lys Gly Phe Gly
1               5                   10                  15
Phe Ile Glu Val Glu Ala Gln Ala Asp Val Phe Val His Phe Ser Ala
                20                  25                  30
Ile Gln Gly Glu Gly Phe Lys Thr Leu Glu Gly Gln Ala Val Ser
            35                  40                  45
Phe Glu Ile Val Glu Gly Asn Arg Ala Pro Ala Ala Ala Asn Val Thr
    50                  55                  60
Lys Glu Ala
65
```

<210> SEQ ID NO 272
<211> LENGTH: 67
<212> TYPE: PRT
<213> ORGANISM: Artificial Sequence
<220> FEATURE:
<223> OTHER INFORMATION: synthetic sequence, Bs_CspB_G22A_D24A_T64A_E66A

<400> SEQUENCE: 272

```
Met Val Glu Gly Lys Val Lys Trp Phe Asn Ser Glu Lys Gly Phe Gly
1               5                   10                  15
Phe Ile Glu Val Glu Ala Gln Ala Asp Val Phe Val His Phe Ser Ala
                20                  25                  30
Ile Gln Gly Glu Gly Phe Lys Thr Leu Glu Gly Gln Ala Val Ser
            35                  40                  45
Phe Glu Ile Val Glu Gly Asn Arg Gly Pro Gln Ala Ala Asn Val Ala
    50                  55                  60
Lys Ala Ala
65
```

<210> SEQ ID NO 273
<211> LENGTH: 67
<212> TYPE: PRT
<213> ORGANISM: Artificial Sequence
<220> FEATURE:
<223> OTHER INFORMATION: synthetic sequence, Bs_CspB_G22A_D24A_T40A_E42A

<400> SEQUENCE: 273

```
Met Val Glu Gly Lys Val Lys Trp Phe Asn Ser Glu Lys Gly Phe Gly
1               5                   10                  15
Phe Ile Glu Val Glu Ala Gln Ala Asp Val Phe Val His Phe Ser Ala
                20                  25                  30
Ile Gln Gly Glu Gly Phe Lys Ala Leu Ala Glu Gly Gln Ala Val Ser
            35                  40                  45
Phe Glu Ile Val Glu Gly Asn Arg Gly Pro Gln Ala Ala Asn Val Thr
    50                  55                  60
Lys Glu Ala
65
```

<210> SEQ ID NO 274
<211> LENGTH: 67
<212> TYPE: PRT
<213> ORGANISM: Artificial Sequence
<220> FEATURE:
<223> OTHER INFORMATION: synthetic sequence, Bs_CspB_G22A_D24A_Q59A-A61S

```
<400> SEQUENCE: 274

Met Val Glu Gly Lys Val Lys Trp Phe Asn Ser Glu Lys Gly Phe Gly
1               5                   10                  15

Phe Ile Glu Val Glu Ala Gln Ala Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Ala Ala Ser Asn Val Thr
        50                  55                  60

Lys Glu Ala
65

<210> SEQ ID NO 275
<211> LENGTH: 67
<212> TYPE: PRT
<213> ORGANISM: Artificial Sequence
<220> FEATURE:
<223> OTHER INFORMATION: synthetic sequence, Bs_CspB_E3A-K5A

<400> SEQUENCE: 275

Met Val Ala Gly Ala Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 276
<211> LENGTH: 67
<212> TYPE: PRT
<213> ORGANISM: Artificial Sequence
<220> FEATURE:
<223> OTHER INFORMATION: synthetic sequence, Bs_CspB_K5A-K7A

<400> SEQUENCE: 276

Met Val Glu Gly Ala Val Ala Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 277
<211> LENGTH: 67
<212> TYPE: PRT
<213> ORGANISM: Artificial Sequence
<220> FEATURE:
<223> OTHER INFORMATION: synthetic sequence, Bs_CspB_W8A-N10A

<400> SEQUENCE: 277

Met Val Glu Gly Lys Val Lys Ala Phe Ala Ser Glu Lys Gly Phe Gly
1               5                   10                  15
```

```
Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 278
<211> LENGTH: 67
<212> TYPE: PRT
<213> ORGANISM: Artificial Sequence
<220> FEATURE:
<223> OTHER INFORMATION: synthetic sequence, Bs_CspB_F9A-S11A

<400> SEQUENCE: 278

Met Val Glu Gly Lys Val Lys Trp Ala Asn Ala Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 279
<211> LENGTH: 67
<212> TYPE: PRT
<213> ORGANISM: Artificial Sequence
<220> FEATURE:
<223> OTHER INFORMATION: synthetic sequence, Bs_CspB_N10A-E12A

<400> SEQUENCE: 279

Met Val Glu Gly Lys Val Lys Trp Phe Ala Ser Ala Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 280
<211> LENGTH: 67
<212> TYPE: PRT
<213> ORGANISM: Artificial Sequence
<220> FEATURE:
<223> OTHER INFORMATION: synthetic sequence, Bs_CspB_V20A-G22A

<400> SEQUENCE: 280

Met Val Glu Gly Lys Val Lys Trp Phe Asn Ser Glu Lys Gly Phe Gly
1               5                   10                  15

Phe Ile Glu Ala Glu Ala Gln Asp Asp Val Phe Val His Phe Ser Ala
            20                  25                  30
```

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 281
<211> LENGTH: 67
<212> TYPE: PRT
<213> ORGANISM: Artificial Sequence
<220> FEATURE:
<223> OTHER INFORMATION: synthetic sequence, Bs_CspB_E21A-Q23A

<400> SEQUENCE: 281

Met Val Glu Gly Lys Val Lys Trp Phe Asn Ser Glu Lys Gly Phe Gly
1               5                   10                  15

Phe Ile Glu Val Ala Gly Ala Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 282
<211> LENGTH: 67
<212> TYPE: PRT
<213> ORGANISM: Artificial Sequence
<220> FEATURE:
<223> OTHER INFORMATION: synthetic sequence, Bs_CspB_G22A-D24A

<400> SEQUENCE: 282

Met Val Glu Gly Lys Val Lys Trp Phe Asn Ser Glu Lys Gly Phe Gly
1               5                   10                  15

Phe Ile Glu Val Glu Ala Gln Ala Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 283
<211> LENGTH: 67
<212> TYPE: PRT
<213> ORGANISM: Artificial Sequence
<220> FEATURE:
<223> OTHER INFORMATION: synthetic sequence, Bs_CspB_D24A-V26A

<400> SEQUENCE: 283

Met Val Glu Gly Lys Val Lys Trp Phe Asn Ser Glu Lys Gly Phe Gly
1               5                   10                  15

Phe Ile Glu Val Glu Gly Gln Ala Asp Ala Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr

```
                50                  55                  60

Lys Glu Ala
65

<210> SEQ ID NO 284
<211> LENGTH: 67
<212> TYPE: PRT
<213> ORGANISM: Artificial Sequence
<220> FEATURE:
<223> OTHER INFORMATION: synthetic sequence, Bs_CspB_H29A-S31A

<400> SEQUENCE: 284

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Ala Phe Ala Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 285
<211> LENGTH: 67
<212> TYPE: PRT
<213> ORGANISM: Artificial Sequence
<220> FEATURE:
<223> OTHER INFORMATION: synthetic sequence, Bs_CspB_F30A-A32S

<400> SEQUENCE: 285

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Ala Ser Ser
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 286
<211> LENGTH: 67
<212> TYPE: PRT
<213> ORGANISM: Artificial Sequence
<220> FEATURE:
<223> OTHER INFORMATION: synthetic sequence, Bs_CspB_Q34A-E36A

<400> SEQUENCE: 286

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Ala Gly Ala Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 287
<211> LENGTH: 67
<212> TYPE: PRT
<213> ORGANISM: Artificial Sequence
<220> FEATURE:
<223> OTHER INFORMATION: synthetic sequence, Bs_CspB_G35A-G37A

<400> SEQUENCE: 287

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Ala Glu Ala Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 288
<211> LENGTH: 67
<212> TYPE: PRT
<213> ORGANISM: Artificial Sequence
<220> FEATURE:
<223> OTHER INFORMATION: synthetic sequence, Bs_CspB_E36A-F38A

<400> SEQUENCE: 288

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Ala Gly Ala Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 289
<211> LENGTH: 67
<212> TYPE: PRT
<213> ORGANISM: Artificial Sequence
<220> FEATURE:
<223> OTHER INFORMATION: synthetic sequence, Bs_CspB_G37A-K39A

<400> SEQUENCE: 289

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Ala Phe Ala Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 290
<211> LENGTH: 67

<212> TYPE: PRT
<213> ORGANISM: Artificial Sequence
<220> FEATURE:
<223> OTHER INFORMATION: synthetic sequence, Bs_CspB_F38A-T40A

<400> SEQUENCE: 290

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Ala Lys Ala Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 291
<211> LENGTH: 67
<212> TYPE: PRT
<213> ORGANISM: Artificial Sequence
<220> FEATURE:
<223> OTHER INFORMATION: synthetic sequence, Bs_CspB_T40A-E42A

<400> SEQUENCE: 291

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ala Leu Ala Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 292
<211> LENGTH: 67
<212> TYPE: PRT
<213> ORGANISM: Artificial Sequence
<220> FEATURE:
<223> OTHER INFORMATION: synthetic sequence, Bs_CspB_L41A-E43A

<400> SEQUENCE: 292

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Ala Glu Ala Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 293
<211> LENGTH: 67
<212> TYPE: PRT
<213> ORGANISM: Artificial Sequence
<220> FEATURE:
<223> OTHER INFORMATION: synthetic sequence, Bs_CspB_E42A-G44A

<400> SEQUENCE: 293

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Ala Glu Ala Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 294
<211> LENGTH: 67
<212> TYPE: PRT
<213> ORGANISM: Artificial Sequence
<220> FEATURE:
<223> OTHER INFORMATION: synthetic sequence, Bs_CspB_G44A-A46S

<400> SEQUENCE: 294

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Ala Gln Ser Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 295
<211> LENGTH: 67
<212> TYPE: PRT
<213> ORGANISM: Artificial Sequence
<220> FEATURE:
<223> OTHER INFORMATION: synthetic sequence, Bs_CspB_Q45A-V47A

<400> SEQUENCE: 295

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Ala Ala Ala Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 296
<211> LENGTH: 67
<212> TYPE: PRT
<213> ORGANISM: Artificial Sequence
<220> FEATURE:
<223> OTHER INFORMATION: synthetic sequence, Bs_CspB_S48A-E50A

<400> SEQUENCE: 296

Met Val Glu Gly Lys Val Lys Trp Phe Asn Ser Glu Lys Gly Phe Gly

```
                1               5                  10                  15
            Phe Ile Glu Val Glu Gly Gln Asp Asp Val Phe Val His Phe Ser Ala
                            20                  25                  30
            Ile Gln Gly Glu Gly Phe Lys Thr Leu Glu Glu Gly Gln Ala Val Ala
                        35                  40                  45
            Phe Ala Ile Val Glu Gly Asn Arg Gly Pro Gln Ala Ala Asn Val Thr
                50                  55                  60

Lys Glu Ala
            65

<210> SEQ ID NO 297
<211> LENGTH: 67
<212> TYPE: PRT
<213> ORGANISM: Artificial Sequence
<220> FEATURE:
<223> OTHER INFORMATION: synthetic sequence, Bs_CspB_E50A-V52A

<400> SEQUENCE: 297

Met Val Glu Gly Lys Val Lys Trp Phe Asn Ser Glu Lys Gly Phe Gly
            1               5                  10                  15
            Phe Ile Glu Val Glu Gly Gln Asp Asp Val Phe Val His Phe Ser Ala
                            20                  25                  30
            Ile Gln Gly Glu Gly Phe Lys Thr Leu Glu Glu Gly Gln Ala Val Ser
                        35                  40                  45
            Phe Ala Ile Ala Glu Gly Asn Arg Gly Pro Gln Ala Ala Asn Val Thr
                50                  55                  60

Lys Glu Ala
            65

<210> SEQ ID NO 298
<211> LENGTH: 67
<212> TYPE: PRT
<213> ORGANISM: Artificial Sequence
<220> FEATURE:
<223> OTHER INFORMATION: synthetic sequence, Bs_CspB_I51A-E53A

<400> SEQUENCE: 298

Met Val Glu Gly Lys Val Lys Trp Phe Asn Ser Glu Lys Gly Phe Gly
            1               5                  10                  15
            Phe Ile Glu Val Glu Gly Gln Asp Asp Val Phe Val His Phe Ser Ala
                            20                  25                  30
            Ile Gln Gly Glu Gly Phe Lys Thr Leu Glu Glu Gly Gln Ala Val Ser
                        35                  40                  45
            Phe Glu Ala Val Ala Gly Asn Arg Gly Pro Gln Ala Ala Asn Val Thr
                50                  55                  60

Lys Glu Ala
            65

<210> SEQ ID NO 299
<211> LENGTH: 67
<212> TYPE: PRT
<213> ORGANISM: Artificial Sequence
<220> FEATURE:
<223> OTHER INFORMATION: synthetic sequence, Bs_CspB_V52A-G54A

<400> SEQUENCE: 299

Met Val Glu Gly Lys Val Lys Trp Phe Asn Ser Glu Lys Gly Phe Gly
            1               5                  10                  15
            Phe Ile Glu Val Glu Gly Gln Asp Asp Val Phe Val His Phe Ser Ala
                            20                  25                  30
```

```
Ile Gln Gly Glu Gly Phe Lys Thr Leu Glu Glu Gly Gln Ala Val Ser
            35                  40                  45

Phe Glu Ile Ala Glu Ala Asn Arg Gly Pro Gln Ala Ala Asn Val Thr
 50                  55                  60

Lys Glu Ala
 65

<210> SEQ ID NO 300
<211> LENGTH: 67
<212> TYPE: PRT
<213> ORGANISM: Artificial Sequence
<220> FEATURE:
<223> OTHER INFORMATION: synthetic sequence, Bs_CspB_E53A-N55A

<400> SEQUENCE: 300

Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
             20                  25                  30

Ile Gln Gly Glu Gly Phe Lys Thr Leu Glu Glu Gly Gln Ala Val Ser
            35                  40                  45

Phe Glu Ile Val Ala Gly Ala Arg Gly Pro Gln Ala Ala Asn Val Thr
 50                  55                  60

Lys Glu Ala
 65

<210> SEQ ID NO 301
<211> LENGTH: 67
<212> TYPE: PRT
<213> ORGANISM: Artificial Sequence
<220> FEATURE:
<223> OTHER INFORMATION: synthetic sequence, Bs_CspB_G54A-R56A

<400> SEQUENCE: 301

Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
             20                  25                  30

Ile Gln Gly Glu Gly Phe Lys Thr Leu Glu Glu Gly Gln Ala Val Ser
            35                  40                  45

Phe Glu Ile Val Glu Ala Asn Ala Gly Pro Gln Ala Ala Asn Val Thr
 50                  55                  60

Lys Glu Ala
 65

<210> SEQ ID NO 302
<211> LENGTH: 67
<212> TYPE: PRT
<213> ORGANISM: Artificial Sequence
<220> FEATURE:
<223> OTHER INFORMATION: synthetic sequence, Bs_CspB_N55A-G57A

<400> SEQUENCE: 302

Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
             20                  25                  30

Ile Gln Gly Glu Gly Phe Lys Thr Leu Glu Glu Gly Gln Ala Val Ser
            35                  40                  45
```

```
Phe Glu Ile Val Glu Gly Ala Arg Ala Pro Gln Ala Ala Asn Val Thr
        50                  55                  60

Lys Glu Ala
 65
```

<210> SEQ ID NO 303
<211> LENGTH: 67
<212> TYPE: PRT
<213> ORGANISM: Artificial Sequence
<220> FEATURE:
<223> OTHER INFORMATION: synthetic sequence, Bs_CspB_R56A-P58A

<400> SEQUENCE: 303

```
Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
                 20                  25                  30

Ile Gln Gly Glu Gly Phe Lys Thr Leu Glu Glu Gly Gln Ala Val Ser
            35                  40                  45

Phe Glu Ile Val Glu Gly Asn Ala Gly Ala Gln Ala Ala Asn Val Thr
        50                  55                  60

Lys Glu Ala
 65
```

<210> SEQ ID NO 304
<211> LENGTH: 67
<212> TYPE: PRT
<213> ORGANISM: Artificial Sequence
<220> FEATURE:
<223> OTHER INFORMATION: synthetic sequence, Bs_CspB_G57A-Q59A

<400> SEQUENCE: 304

```
Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
                 20                  25                  30

Ile Gln Gly Glu Gly Phe Lys Thr Leu Glu Glu Gly Gln Ala Val Ser
            35                  40                  45

Phe Glu Ile Val Glu Gly Asn Arg Ala Pro Ala Ala Ala Asn Val Thr
        50                  55                  60

Lys Glu Ala
 65
```

<210> SEQ ID NO 305
<211> LENGTH: 67
<212> TYPE: PRT
<213> ORGANISM: Artificial Sequence
<220> FEATURE:
<223> OTHER INFORMATION: synthetic sequence, Bs_CspB_P58A-A60S

<400> SEQUENCE: 305

```
Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
                 20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Ala Gln Ser Ala Asn Val Thr
        50                  55                  60

Lys Glu Ala
```

<210> SEQ ID NO 306
<211> LENGTH: 67
<212> TYPE: PRT
<213> ORGANISM: Artificial Sequence
<220> FEATURE:
<223> OTHER INFORMATION: synthetic sequence, Bs_CspB_Q59A-A61S

<400> SEQUENCE: 306

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Ala Ala Ser Asn Val Thr
        50                  55                  60

Lys Glu Ala
65

<210> SEQ ID NO 307
<211> LENGTH: 67
<212> TYPE: PRT
<213> ORGANISM: Artificial Sequence
<220> FEATURE:
<223> OTHER INFORMATION: synthetic sequence, Bs_CspB_N62A-T64A

<400> SEQUENCE: 307

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Ala Val Ala
        50                  55                  60

Lys Glu Ala
65

<210> SEQ ID NO 308
<211> LENGTH: 67
<212> TYPE: PRT
<213> ORGANISM: Artificial Sequence
<220> FEATURE:
<223> OTHER INFORMATION: synthetic sequence, Bs_CspB_V63A-K65A

<400> SEQUENCE: 308

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Ala Thr
        50                  55                  60

Ala Glu Ala
65

<210> SEQ ID NO 309

```
<211> LENGTH: 67
<212> TYPE: PRT
<213> ORGANISM: Artificial Sequence
<220> FEATURE:
<223> OTHER INFORMATION: synthetic sequence, Bs_CspB_T64A-E66A

<400> SEQUENCE: 309

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Ala
    50                  55                  60

Lys Ala Ala
65

<210> SEQ ID NO 310
<211> LENGTH: 67
<212> TYPE: PRT
<213> ORGANISM: Artificial Sequence
<220> FEATURE:
<223> OTHER INFORMATION: synthetic sequence, Bs_CspB_K65A-A67S

<400> SEQUENCE: 310

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Ala Glu Ser
65

<210> SEQ ID NO 311
<211> LENGTH: 67
<212> TYPE: PRT
<213> ORGANISM: Artificial Sequence
<220> FEATURE:
<223> OTHER INFORMATION: synthetic sequence, Bs_CspB_A46S-S48A

<400> SEQUENCE: 311

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ser Val Ala
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 312
<211> LENGTH: 67
<212> TYPE: PRT
<213> ORGANISM: Artificial Sequence
<220> FEATURE:
```

<223> OTHER INFORMATION: synthetic sequence, Bs_CspB_A32S-Q34A

<400> SEQUENCE: 312

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ser
            20                  25                  30

Ile Ala Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 313
<211> LENGTH: 69
<212> TYPE: PRT
<213> ORGANISM: Artificial Sequence
<220> FEATURE:
<223> OTHER INFORMATION: synthetic sequence, Chimeric
      Ab_Csp2_R1_Ec_CspC_bb

<400> SEQUENCE: 313

Met Ala Lys Ile Lys Gly Gln Val Lys Phe Phe Ala Gln Asp Lys Gly
1               5                   10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Ile Gln Asp Gly Gln Lys Gly Pro Ala Ala Val
    50                  55                  60

Asn Val Thr Ala Ile
65

<210> SEQ ID NO 314
<211> LENGTH: 69
<212> TYPE: PRT
<213> ORGANISM: Artificial Sequence
<220> FEATURE:
<223> OTHER INFORMATION: synthetic sequence,
      Chimeric Tm_Csp1_R1_Ec_CspC_bb

<400> SEQUENCE: 314

Met Ala Lys Ile Lys Gly Gln Val Lys Trp Phe Asp Ser Lys Lys Gly
1               5                   10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Ile Gln Asp Gly Gln Lys Gly Pro Ala Ala Val
    50                  55                  60

Asn Val Thr Ala Ile
65

<210> SEQ ID NO 315
<211> LENGTH: 69
<212> TYPE: PRT
<213> ORGANISM: Artificial Sequence
<220> FEATURE:
<223> OTHER INFORMATION: synthetic sequence, Chimeric
      Tt_Csp1_R1_Ec_CspC_bb

<400> SEQUENCE: 315

Met Ala Lys Ile Lys Gly Gln Val Lys Trp Phe Asn Ala Glu Lys Gly
1               5                   10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Ile Gln Asp Gly Gln Lys Gly Pro Ala Ala Val
    50                  55                  60

Asn Val Thr Ala Ile
65

<210> SEQ ID NO 316
<211> LENGTH: 68
<212> TYPE: PRT
<213> ORGANISM: Artificial Sequence
<220> FEATURE:
<223> OTHER INFORMATION: synthetic sequence, Chimeric
      Tt_Csp1_R2_Ec_CspC_bb

<400> SEQUENCE: 316

Met Ala Lys Ile Lys Gly Gln Val Lys Trp Phe Asn Glu Ser Lys Gly
1               5                   10                  15

Phe Gly Phe Ile Glu Arg Glu Asp Gly Thr Asp Val Phe Val His Phe
            20                  25                  30

Ser Ala Ile Gln Gly Asn Gly Phe Lys Thr Leu Ala Glu Gly Gln Asn
        35                  40                  45

Val Glu Phe Glu Ile Gln Asp Gly Gln Lys Gly Pro Ala Ala Val Asn
    50                  55                  60

Val Thr Ala Ile
65

<210> SEQ ID NO 317
<211> LENGTH: 68
<212> TYPE: PRT
<213> ORGANISM: Artificial Sequence
<220> FEATURE:
<223> OTHER INFORMATION: synthetic sequence, Chimeric
      Tm_Csp1_R2_Ec_CspC_bb

<400> SEQUENCE: 317

Met Ala Lys Ile Lys Gly Gln Val Lys Trp Phe Asn Glu Ser Lys Gly
1               5                   10                  15

Phe Gly Phe Ile Thr Lys Asp Glu Gly Asp Val Phe Val His Phe
            20                  25                  30

Ser Ala Ile Gln Gly Asn Gly Phe Lys Thr Leu Ala Glu Gly Gln Asn
        35                  40                  45

Val Glu Phe Glu Ile Gln Asp Gly Gln Lys Gly Pro Ala Ala Val Asn
    50                  55                  60

Val Thr Ala Ile
65

<210> SEQ ID NO 318
<211> LENGTH: 69
<212> TYPE: PRT
<213> ORGANISM: Artificial Sequence
<220> FEATURE:
<223> OTHER INFORMATION: synthetic sequence, Chimeric
      Tt_Csp1_R3_Ec_CspC_bb

<400> SEQUENCE: 318

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Ile Gln Asp Gly Gln Lys Gly Pro Ala Ala Val
    50                  55                  60

Asn Val Thr Ala Ile
65

<210> SEQ ID NO 319
<211> LENGTH: 69
<212> TYPE: PRT
<213> ORGANISM: Artificial Sequence
<220> FEATURE:
<223> OTHER INFORMATION: synthetic sequence, Chimeric
      Ec_CspD_R3_Ec_CspC_bb

<400> SEQUENCE: 319

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
            20                  25                  30

Phe Ser Ala Ile Gln Met Asp Gly Tyr Arg Thr Leu Ala Glu Gly Gln
        35                  40                  45

Asn Val Glu Phe Glu Ile Gln Asp Gly Gln Lys Gly Pro Ala Ala Val
    50                  55                  60

Asn Val Thr Ala Ile
65

<210> SEQ ID NO 320
<211> LENGTH: 69
<212> TYPE: PRT
<213> ORGANISM: Artificial Sequence
<220> FEATURE:
<223> OTHER INFORMATION: synthetic sequence, Chimeric
      Ec_CspG_R2_Ec_CspC_bb

<400> SEQUENCE: 320

Met Ala Lys Ile Lys Gly Gln Val Lys Trp Phe Asn Glu Ser Lys Gly
1               5                   10                  15

Phe Gly Phe Ile Thr Pro Asp Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Ile Gln Asp Gly Gln Lys Gly Pro Ala Ala Val
    50                  55                  60

Asn Val Thr Ala Ile
65

<210> SEQ ID NO 321
<211> LENGTH: 69
<212> TYPE: PRT
<213> ORGANISM: Artificial Sequence
<220> FEATURE:
<223> OTHER INFORMATION: synthetic sequence, Chimeric
      Ec_CspD_R1_Ec_CspC_bb

<400> SEQUENCE: 321

```
Met Ala Lys Ile Lys Gly Gln Val Lys Trp Phe Asn Ala Lys Gly
1               5                   10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Ile Gln Asp Gly Gln Lys Gly Pro Ala Ala Val
    50                  55                  60

Asn Val Thr Ala Ile
65

<210> SEQ ID NO 322
<211> LENGTH: 69
<212> TYPE: PRT
<213> ORGANISM: Artificial Sequence
<220> FEATURE:
<223> OTHER INFORMATION: synthetic sequence, Chimeric
      Ec_CspC_R3_Ab_Csp2_bb

<400> SEQUENCE: 322

Met Ala Thr Gly Thr Val Lys Phe Phe Ala Gln Asp Lys Gly Phe Gly
1               5                   10                  15

Phe Ile Thr Pro Asp Asn Gly Gly Pro Asp Val Phe Val His Ile Ser
            20                  25                  30

Ala Val Gln Gly Asn Gly Phe Lys Thr Leu Gln Asp Gly Gln Lys Val
        35                  40                  45

Ser Tyr Glu Leu Gly Gln Asp Arg Lys Thr Gly Lys Ser Lys Ala Glu
    50                  55                  60

Asn Val Thr Leu Leu
65

<210> SEQ ID NO 323
<211> LENGTH: 67
<212> TYPE: PRT
<213> ORGANISM: Artificial Sequence
<220> FEATURE:
<223> OTHER INFORMATION: synthetic sequence, Chimeric
      Tm_Csp1_R1_Ab_Csp2_bb

<400> SEQUENCE: 323

Met Ala Thr Gly Thr Val Lys Trp Phe Asp Ser Lys Lys Gly Phe Gly
1               5                   10                  15

Phe Ile Thr Pro Asp Asn Gly Gly Pro Asp Val Phe Val His Ile Ser
            20                  25                  30

Ala Val Gly Phe Gly Gly Ser Leu Gln Asp Gly Gln Lys Val Ser Tyr
        35                  40                  45

Glu Leu Gly Gln Asp Arg Lys Thr Gly Lys Ser Lys Ala Glu Asn Val
    50                  55                  60

Thr Leu Leu
65

<210> SEQ ID NO 324
<211> LENGTH: 67
<212> TYPE: PRT
<213> ORGANISM: Artificial Sequence
<220> FEATURE:
<223> OTHER INFORMATION: synthetic sequence, Chimeric
      Ec_CspC_R1_Ab_Csp2_bb

<400> SEQUENCE: 324
```

```
Met Ala Thr Gly Thr Val Lys Trp Phe Asn Glu Ser Lys Gly Phe Gly
1               5                   10                  15

Phe Ile Thr Pro Asp Asn Gly Gly Pro Asp Val Phe Val His Ile Ser
            20                  25                  30

Ala Val Gly Phe Gly Gly Ser Leu Gln Asp Gly Gln Lys Val Ser Tyr
        35                  40                  45

Glu Leu Gly Gln Asp Arg Lys Thr Gly Lys Ser Lys Ala Glu Asn Val
    50                  55                  60

Thr Leu Leu
65
```

<210> SEQ ID NO 325
<211> LENGTH: 74
<212> TYPE: PRT
<213> ORGANISM: Artificial Sequence
<220> FEATURE:
<223> OTHER INFORMATION: synthetic sequence, Chimeric
      Ec_CspG_R1_Ec_CspD_bb

<400> SEQUENCE: 325

```
Met Glu Lys Gly Thr Val Lys Trp Phe Asn Ala Asp Lys Gly Phe Gly
1               5                   10                  15

Phe Ile Cys Pro Glu Gly Gly Gly Glu Asp Ile Phe Ala His Tyr Ser
            20                  25                  30

Thr Ile Gln Met Asp Gly Tyr Arg Thr Leu Lys Ala Gly Gln Ser Val
        35                  40                  45

Gln Phe Asp Val His Gln Gly Pro Lys Gly Asn His Ala Ser Val Ile
    50                  55                  60

Val Pro Val Glu Val Glu Ala Ala Val Ala
65                  70
```

<210> SEQ ID NO 326
<211> LENGTH: 74
<212> TYPE: PRT
<213> ORGANISM: Artificial Sequence
<220> FEATURE:
<223> OTHER INFORMATION: synthetic sequence, Chimeric
      Tt_Csp1_R1_Ec_CspD_bb

<400> SEQUENCE: 326

```
Met Glu Lys Gly Thr Val Lys Trp Phe Asn Ala Glu Lys Gly Phe Gly
1               5                   10                  15

Phe Ile Cys Pro Glu Gly Gly Gly Glu Asp Ile Phe Ala His Tyr Ser
            20                  25                  30

Thr Ile Gln Met Asp Gly Tyr Arg Thr Leu Lys Ala Gly Gln Ser Val
        35                  40                  45

Gln Phe Asp Val His Gln Gly Pro Lys Gly Asn His Ala Ser Val Ile
    50                  55                  60

Val Pro Val Glu Val Glu Ala Ala Val Ala
65                  70
```

<210> SEQ ID NO 327
<211> LENGTH: 74
<212> TYPE: PRT
<213> ORGANISM: Artificial Sequence
<220> FEATURE:
<223> OTHER INFORMATION: synthetic sequence, Chimeric
      Ec_CspC_R1_Ec_CspD_bb

<400> SEQUENCE: 327

```
Met Glu Lys Gly Thr Val Lys Trp Phe Asn Glu Ser Lys Gly Phe Gly
```

```
    1               5                   10                  15
Phe Ile Cys Pro Glu Gly Gly Gly Glu Asp Ile Phe Ala His Tyr Ser
                20                  25                  30

Thr Ile Gln Met Asp Gly Tyr Arg Thr Leu Lys Ala Gly Gln Ser Val
            35                  40                  45

Gln Phe Asp Val His Gln Gly Pro Lys Gly Asn His Ala Ser Val Ile
        50                  55                  60

Val Pro Val Glu Val Glu Ala Ala Val Ala
65                  70

<210> SEQ ID NO 328
<211> LENGTH: 74
<212> TYPE: PRT
<213> ORGANISM: Artificial Sequence
<220> FEATURE:
<223> OTHER INFORMATION: synthetic sequence, Chimeric
      Tm_Csp1_R3_Ec_CspD_bb

<400> SEQUENCE: 328

Met Glu Lys Gly Thr Val Lys Trp Phe Asn Asn Ala Lys Gly Phe Gly
1               5                   10                  15

Phe Ile Cys Pro Glu Gly Gly Gly Glu Asp Ile Phe Ala His Tyr Ser
                20                  25                  30

Thr Ile Glu Met Glu Gly Phe Lys Thr Leu Lys Ala Gly Gln Ser Val
            35                  40                  45

Gln Phe Asp Val His Gln Gly Pro Lys Gly Asn His Ala Ser Val Ile
        50                  55                  60

Val Pro Val Glu Val Glu Ala Ala Val Ala
65                  70

<210> SEQ ID NO 329
<211> LENGTH: 73
<212> TYPE: PRT
<213> ORGANISM: Artificial Sequence
<220> FEATURE:
<223> OTHER INFORMATION: synthetic sequence, Chimeric
      Bs_CspB_R2_Ec_CspD_bb

<400> SEQUENCE: 329

Met Glu Lys Gly Thr Val Lys Trp Phe Asn Asn Ala Lys Gly Phe Gly
1               5                   10                  15

Phe Ile Glu Val Glu Gly Gln Asp Asp Ile Phe Ala His Tyr Ser Thr
                20                  25                  30

Ile Gln Met Asp Gly Tyr Arg Thr Leu Lys Ala Gly Gln Ser Val Gln
            35                  40                  45

Phe Asp Val His Gln Gly Pro Lys Gly Asn His Ala Ser Val Ile Val
        50                  55                  60

Pro Val Glu Val Glu Ala Ala Val Ala
65                  70

<210> SEQ ID NO 330
<211> LENGTH: 74
<212> TYPE: PRT
<213> ORGANISM: Artificial Sequence
<220> FEATURE:
<223> OTHER INFORMATION: synthetic sequence, Chimeric
      Ec_CspC_R2_Ec_CspD_bb

<400> SEQUENCE: 330

Met Glu Lys Gly Thr Val Lys Trp Phe Asn Asn Ala Lys Gly Phe Gly
1               5                   10                  15
```

Phe Ile Thr Pro Ala Asp Gly Ser Lys Asp Ile Phe Ala His Tyr Ser
            20                  25                  30

Thr Ile Gln Met Asp Gly Tyr Arg Thr Leu Lys Ala Gly Gln Ser Val
            35                  40                  45

Gln Phe Asp Val His Gln Gly Pro Lys Gly Asn His Ala Ser Val Ile
        50                  55                  60

Val Pro Val Glu Val Glu Ala Ala Val Ala
65                  70

<210> SEQ ID NO 331
<211> LENGTH: 74
<212> TYPE: PRT
<213> ORGANISM: Artificial Sequence
<220> FEATURE:
<223> OTHER INFORMATION: synthetic sequence, Chimeric
      Ec_CspG_R2_Ec_CspD_bb

<400> SEQUENCE: 331

Met Glu Lys Gly Thr Val Lys Trp Phe Asn Asn Ala Lys Gly Phe Gly
1               5                   10                  15

Phe Ile Thr Pro Asp Asp Gly Ser Lys Asp Ile Phe Ala His Tyr Ser
            20                  25                  30

Thr Ile Gln Met Asp Gly Tyr Arg Thr Leu Lys Ala Gly Gln Ser Val
            35                  40                  45

Gln Phe Asp Val His Gln Gly Pro Lys Gly Asn His Ala Ser Val Ile
        50                  55                  60

Val Pro Val Glu Val Glu Ala Ala Val Ala
65                  70

<210> SEQ ID NO 332
<211> LENGTH: 74
<212> TYPE: PRT
<213> ORGANISM: Artificial Sequence
<220> FEATURE:
<223> OTHER INFORMATION: synthetic sequence, Chimeric
      Ab_Csp2_R2_Ec_CspD_bb

<400> SEQUENCE: 332

Met Glu Lys Gly Thr Val Lys Trp Phe Asn Asn Ala Lys Gly Phe Gly
1               5                   10                  15

Phe Ile Thr Pro Asp Asn Gly Gly Pro Asp Ile Phe Ala His Tyr Ser
            20                  25                  30

Thr Ile Gln Met Asp Gly Tyr Arg Thr Leu Lys Ala Gly Gln Ser Val
            35                  40                  45

Gln Phe Asp Val His Gln Gly Pro Lys Gly Asn His Ala Ser Val Ile
        50                  55                  60

Val Pro Val Glu Val Glu Ala Ala Val Ala
65                  70

<210> SEQ ID NO 333
<211> LENGTH: 74
<212> TYPE: PRT
<213> ORGANISM: Artificial Sequence
<220> FEATURE:
<223> OTHER INFORMATION: synthetic sequence, Chimeric
      Bs_CspB_R1_Ec_CspD_bb

<400> SEQUENCE: 333

Met Glu Lys Gly Thr Val Lys Trp Phe Asn Ser Glu Lys Gly Phe Gly
1               5                   10                  15

```
Phe Ile Cys Pro Gly Gly Gly Glu Asp Ile Phe Ala His Tyr Ser
             20                  25                  30

Thr Ile Gln Met Asp Gly Tyr Arg Thr Leu Lys Ala Gln Ser Val
         35                  40                  45

Gln Phe Asp Val His Gln Gly Pro Lys Gly Asn His Ala Ser Val Ile
 50                      55                  60

Val Pro Val Glu Val Glu Ala Ala Val Ala
 65                  70

<210> SEQ ID NO 334
<211> LENGTH: 66
<212> TYPE: PRT
<213> ORGANISM: Artificial Sequence
<220> FEATURE:
<223> OTHER INFORMATION: synthetic sequence, Chimeric
      Ab_Csp2_R1_Tm_Csp1_bb

<400> SEQUENCE: 334

Met Arg Gly Lys Val Lys Phe Phe Ala Gln Asp Lys Gly Tyr Gly Phe
 1               5                  10                  15

Ile Thr Lys Asp Glu Gly Gly Asp Val Phe Val His Trp Ser Ala Ile
             20                  25                  30

Glu Met Glu Gly Phe Lys Thr Leu Lys Glu Gly Gln Val Val Glu Phe
         35                  40                  45

Glu Ile Gln Glu Gly Lys Lys Gly Pro Gln Ala Ala His Val Lys Val
 50                      55                  60

Val Glu
 65

<210> SEQ ID NO 335
<211> LENGTH: 66
<212> TYPE: PRT
<213> ORGANISM: Artificial Sequence
<220> FEATURE:
<223> OTHER INFORMATION: synthetic sequence, Chimeric
      Tt_Csp1_R2_Tm_Csp1_bb

<400> SEQUENCE: 335

Met Arg Gly Lys Val Lys Trp Phe Asp Ser Lys Lys Gly Tyr Gly Phe
 1               5                  10                  15

Ile Glu Arg Glu Asp Gly Thr Asp Val Phe Val His Trp Ser Ala Ile
             20                  25                  30

Glu Met Glu Gly Phe Lys Thr Leu Lys Glu Gly Gln Val Val Glu Phe
         35                  40                  45

Glu Ile Gln Glu Gly Lys Lys Gly Pro Gln Ala Ala His Val Lys Val
 50                      55                  60

Val Glu
 65

<210> SEQ ID NO 336
<211> LENGTH: 66
<212> TYPE: PRT
<213> ORGANISM: Artificial Sequence
<220> FEATURE:
<223> OTHER INFORMATION: synthetic sequence, Chimeric
      Bs_CspB_R2_Tm_Csp1_bb

<400> SEQUENCE: 336

Met Arg Gly Lys Val Lys Trp Phe Asp Ser Lys Lys Gly Tyr Gly Phe
 1               5                  10                  15

Ile Glu Val Glu Gly Gln Asp Asp Val Phe Val His Trp Ser Ala Ile
```

```
            20                  25                  30
Glu Met Glu Gly Phe Lys Thr Leu Lys Glu Gly Gln Val Val Glu Phe
            35                  40                  45

Glu Ile Gln Glu Gly Lys Lys Gly Pro Gln Ala Ala His Val Lys Val
        50                  55                  60

Val Glu
65

<210> SEQ ID NO 337
<211> LENGTH: 66
<212> TYPE: PRT
<213> ORGANISM: Artificial Sequence
<220> FEATURE:
<223> OTHER INFORMATION: synthetic sequence, Chimeric
      Bs_CspB_R3_Tm_Csp1_bb

<400> SEQUENCE: 337

Met Arg Gly Lys Val Lys Trp Phe Asp Ser Lys Lys Gly Tyr Gly Phe
1               5                   10                  15

Ile Thr Lys Asp Glu Gly Gly Asp Val Phe Val His Trp Ser Ala Ile
            20                  25                  30

Gln Gly Glu Gly Phe Lys Thr Leu Lys Glu Gly Gln Val Val Glu Phe
            35                  40                  45

Glu Ile Gln Glu Gly Lys Lys Gly Pro Gln Ala Ala His Val Lys Val
        50                  55                  60

Val Glu
65

<210> SEQ ID NO 338
<211> LENGTH: 67
<212> TYPE: PRT
<213> ORGANISM: Artificial Sequence
<220> FEATURE:
<223> OTHER INFORMATION: synthetic sequence, Chimeric
      Ec_CspC_R2_Tm_Csp1_bb

<400> SEQUENCE: 338

Met Arg Gly Lys Val Lys Trp Phe Asp Ser Lys Lys Gly Tyr Gly Phe
1               5                   10                  15

Ile Thr Pro Ala Asp Gly Ser Lys Asp Val Phe Val His Trp Ser Ala
            20                  25                  30

Ile Glu Met Glu Gly Phe Lys Thr Leu Lys Glu Gly Gln Val Val Glu
            35                  40                  45

Phe Glu Ile Gln Glu Gly Lys Lys Gly Pro Gln Ala Ala His Val Lys
        50                  55                  60

Val Val Glu
65

<210> SEQ ID NO 339
<211> LENGTH: 67
<212> TYPE: PRT
<213> ORGANISM: Artificial Sequence
<220> FEATURE:
<223> OTHER INFORMATION: synthetic sequence, Chimeric
      Ec_CspG_R2_Tm_Csp1_bb

<400> SEQUENCE: 339

Met Arg Gly Lys Val Lys Trp Phe Asp Ser Lys Lys Gly Tyr Gly Phe
1               5                   10                  15

Ile Thr Pro Asp Asp Gly Ser Lys Asp Val Phe Val His Trp Ser Ala
            20                  25                  30
```

Ile Glu Met Glu Gly Phe Lys Thr Leu Lys Glu Gly Gln Val Val Glu
            35                  40                  45

Phe Glu Ile Gln Glu Gly Lys Lys Gly Pro Gln Ala Ala His Val Lys
    50                  55                  60

Val Val Glu
65

<210> SEQ ID NO 340
<211> LENGTH: 67
<212> TYPE: PRT
<213> ORGANISM: Artificial Sequence
<220> FEATURE:
<223> OTHER INFORMATION: synthetic sequence, Chimeric
      Ab_Csp2_R2_Tm_Csp1_bb

<400> SEQUENCE: 340

Met Arg Gly Lys Val Lys Trp Phe Asp Ser Lys Lys Gly Tyr Gly Phe
1               5                   10                  15

Ile Thr Pro Asp Asn Gly Gly Pro Asp Val Phe Val His Trp Ser Ala
            20                  25                  30

Ile Glu Met Glu Gly Phe Lys Thr Leu Lys Glu Gly Gln Val Val Glu
            35                  40                  45

Phe Glu Ile Gln Glu Gly Lys Lys Gly Pro Gln Ala Ala His Val Lys
    50                  55                  60

Val Val Glu
65

<210> SEQ ID NO 341
<211> LENGTH: 66
<212> TYPE: PRT
<213> ORGANISM: Artificial Sequence
<220> FEATURE:
<223> OTHER INFORMATION: synthetic sequence, Chimeric
      Ec_CspG_R1_Tm_Csp1_bb

<400> SEQUENCE: 341

Met Arg Gly Lys Val Lys Trp Phe Asn Ala Asp Lys Gly Tyr Gly Phe
1               5                   10                  15

Ile Thr Lys Asp Glu Gly Gly Asp Val Phe Val His Trp Ser Ala Ile
            20                  25                  30

Glu Met Glu Gly Phe Lys Thr Leu Lys Glu Gly Gln Val Val Glu Phe
            35                  40                  45

Glu Ile Gln Glu Gly Lys Lys Gly Pro Gln Ala Ala His Val Lys Val
    50                  55                  60

Val Glu
65

<210> SEQ ID NO 342
<211> LENGTH: 66
<212> TYPE: PRT
<213> ORGANISM: Artificial Sequence
<220> FEATURE:
<223> OTHER INFORMATION: synthetic sequence, Chimeric
      Tt_Csp1_R1_Tm_Csp1_bb

<400> SEQUENCE: 342

Met Arg Gly Lys Val Lys Trp Phe Asn Ala Glu Lys Gly Tyr Gly Phe
1               5                   10                  15

Ile Thr Lys Asp Glu Gly Gly Asp Val Phe Val His Trp Ser Ala Ile
            20                  25                  30

-continued

Glu Met Glu Gly Phe Lys Thr Leu Lys Glu Gly Gln Val Val Glu Phe
            35                  40                  45

Glu Ile Gln Glu Gly Lys Lys Gly Pro Gln Ala Ala His Val Lys Val
        50                  55                  60

Val Glu
65

<210> SEQ ID NO 343
<211> LENGTH: 66
<212> TYPE: PRT
<213> ORGANISM: Artificial Sequence
<220> FEATURE:
<223> OTHER INFORMATION: synthetic sequence, Chimeric
      Ec_CspC_R1_Tm_Csp1_bb

<400> SEQUENCE: 343

Met Arg Gly Lys Val Lys Trp Phe Asn Glu Ser Lys Gly Tyr Gly Phe
1               5                   10                  15

Ile Thr Lys Asp Glu Gly Gly Asp Val Phe Val His Trp Ser Ala Ile
            20                  25                  30

Glu Met Glu Gly Phe Lys Thr Leu Lys Glu Gly Gln Val Val Glu Phe
        35                      40                  45

Glu Ile Gln Glu Gly Lys Lys Gly Pro Gln Ala Ala His Val Lys Val
    50                      55                  60

Val Glu
65

<210> SEQ ID NO 344
<211> LENGTH: 66
<212> TYPE: PRT
<213> ORGANISM: Artificial Sequence
<220> FEATURE:
<223> OTHER INFORMATION: synthetic sequence, Chimeric
      Ec_CspD_R1_Tm_Csp1_bb

<400> SEQUENCE: 344

Met Arg Gly Lys Val Lys Trp Phe Asn Asn Ala Lys Gly Tyr Gly Phe
1               5                   10                  15

Ile Thr Lys Asp Glu Gly Gly Asp Val Phe Val His Trp Ser Ala Ile
            20                  25                  30

Glu Met Glu Gly Phe Lys Thr Leu Lys Glu Gly Gln Val Val Glu Phe
        35                      40                  45

Glu Ile Gln Glu Gly Lys Lys Gly Pro Gln Ala Ala His Val Lys Val
    50                      55                  60

Val Glu
65

<210> SEQ ID NO 345
<211> LENGTH: 66
<212> TYPE: PRT
<213> ORGANISM: Artificial Sequence
<220> FEATURE:
<223> OTHER INFORMATION: synthetic sequence, Chimeric
      Bs_CspB_R1_Tm_Csp1_bb

<400> SEQUENCE: 345

Met Arg Gly Lys Val Lys Trp Phe Asn Ser Glu Lys Gly Tyr Gly Phe
1               5                   10                  15

Ile Thr Lys Asp Glu Gly Gly Asp Val Phe Val His Trp Ser Ala Ile
            20                  25                  30

Glu Met Glu Gly Phe Lys Thr Leu Lys Glu Gly Gln Val Val Glu Phe

```
                35                  40                  45
Glu Ile Gln Glu Gly Lys Lys Gly Pro Gln Ala Ala His Val Lys Val
        50                  55                  60

Val Glu
65
```

<210> SEQ ID NO 346
<211> LENGTH: 70
<212> TYPE: PRT
<213> ORGANISM: Artificial Sequence
<220> FEATURE:
<223> OTHER INFORMATION: synthetic sequence, Chimeric
    Tm_Csp1_R1_Ec_CspG_bb

<400> SEQUENCE: 346

```
Met Ser Asn Lys Met Thr Gly Leu Val Lys Trp Phe Asp Ser Lys
1               5                   10                  15

Gly Phe Gly Phe Ile Thr Pro Asp Asp Gly Ser Lys Asp Val Phe Val
                20                  25                  30

His Phe Thr Ala Ile Gln Ser Asn Glu Phe Arg Thr Leu Asn Glu Asn
            35                  40                  45

Gln Lys Val Glu Phe Ser Ile Glu Gln Gly Gln Arg Gly Pro Ala Ala
        50                  55                  60

Ala Asn Val Val Thr Leu
65                  70
```

<210> SEQ ID NO 347
<211> LENGTH: 70
<212> TYPE: PRT
<213> ORGANISM: Artificial Sequence
<220> FEATURE:
<223> OTHER INFORMATION: synthetic sequence, Chimeric
    Tm_Csp1_R3_Ec_CspG_bb

<400> SEQUENCE: 347

```
Met Ser Asn Lys Met Thr Gly Leu Val Lys Trp Phe Asn Ala Asp Lys
1               5                   10                  15

Gly Phe Gly Phe Ile Thr Pro Asp Asp Gly Ser Lys Asp Val Phe Val
                20                  25                  30

His Phe Thr Ala Ile Glu Met Glu Gly Phe Lys Thr Leu Asn Glu Asn
            35                  40                  45

Gln Lys Val Glu Phe Ser Ile Glu Gln Gly Gln Arg Gly Pro Ala Ala
        50                  55                  60

Ala Asn Val Val Thr Leu
65                  70
```

<210> SEQ ID NO 348
<211> LENGTH: 70
<212> TYPE: PRT
<213> ORGANISM: Artificial Sequence
<220> FEATURE:
<223> OTHER INFORMATION: synthetic sequence, Chimeric
    Ec_CspC_R3_Ec_CspG_bb

<400> SEQUENCE: 348

```
Met Ser Asn Lys Met Thr Gly Leu Val Lys Trp Phe Asn Ala Asp Lys
1               5                   10                  15

Gly Phe Gly Phe Ile Thr Pro Asp Asp Gly Ser Lys Asp Val Phe Val
                20                  25                  30

His Phe Thr Ala Ile Gln Gly Asn Gly Phe Lys Thr Leu Asn Glu Asn
            35                  40                  45
```

```
Gln Lys Val Glu Phe Ser Ile Glu Gln Gly Gln Arg Gly Pro Ala Ala
    50                  55                  60

Ala Asn Val Val Thr Leu
65                  70

<210> SEQ ID NO 349
<211> LENGTH: 70
<212> TYPE: PRT
<213> ORGANISM: Artificial Sequence
<220> FEATURE:
<223> OTHER INFORMATION: synthetic sequence, Chimeric
      Ec_CspD_R3_Ec_CspG_bb

<400> SEQUENCE: 349

Met Ser Asn Lys Met Thr Gly Leu Val Lys Trp Phe Asn Ala Asp Lys
1               5                   10                  15

Gly Phe Gly Phe Ile Thr Pro Asp Asp Gly Ser Lys Asp Val Phe Val
                20                  25                  30

His Phe Thr Ala Ile Gln Met Asp Gly Tyr Arg Thr Leu Asn Glu Asn
            35                  40                  45

Gln Lys Val Glu Phe Ser Ile Glu Gln Gly Gln Arg Gly Pro Ala Ala
    50                  55                  60

Ala Asn Val Val Thr Leu
65                  70

<210> SEQ ID NO 350
<211> LENGTH: 70
<212> TYPE: PRT
<213> ORGANISM: Artificial Sequence
<220> FEATURE:
<223> OTHER INFORMATION: synthetic sequence, Chimeric
      Tt_Csp1_R1_Ec_CspG_bb

<400> SEQUENCE: 350

Met Ser Asn Lys Met Thr Gly Leu Val Lys Trp Phe Asn Ala Glu Lys
1               5                   10                  15

Gly Phe Gly Phe Ile Thr Pro Asp Asp Gly Ser Lys Asp Val Phe Val
                20                  25                  30

His Phe Thr Ala Ile Gln Ser Asn Glu Phe Arg Thr Leu Asn Glu Asn
            35                  40                  45

Gln Lys Val Glu Phe Ser Ile Glu Gln Gly Gln Arg Gly Pro Ala Ala
    50                  55                  60

Ala Asn Val Val Thr Leu
65                  70

<210> SEQ ID NO 351
<211> LENGTH: 70
<212> TYPE: PRT
<213> ORGANISM: Artificial Sequence
<220> FEATURE:
<223> OTHER INFORMATION: synthetic sequence, Chimeric
      Ec_CspC_R1_Ec_CspG_bb

<400> SEQUENCE: 351

Met Ser Asn Lys Met Thr Gly Leu Val Lys Trp Phe Asn Ala Glu Ser Lys
1               5                   10                  15

Gly Phe Gly Phe Ile Thr Pro Asp Asp Gly Ser Lys Asp Val Phe Val
                20                  25                  30

His Phe Thr Ala Ile Gln Ser Asn Glu Phe Arg Thr Leu Asn Glu Asn
            35                  40                  45
```

```
Gln Lys Val Glu Phe Ser Ile Glu Gln Gly Gln Arg Gly Pro Ala Ala
 50                  55                  60

Ala Asn Val Val Thr Leu
 65                  70

<210> SEQ ID NO 352
<211> LENGTH: 70
<212> TYPE: PRT
<213> ORGANISM: Artificial Sequence
<220> FEATURE:
<223> OTHER INFORMATION: synthetic sequence, Chimeric
      Ec_CspD_R1_Ec_CspG_bb

<400> SEQUENCE: 352

Met Ser Asn Lys Met Thr Gly Leu Val Lys Trp Phe Asn Asn Ala Lys
 1                5                  10                  15

Gly Phe Gly Phe Ile Thr Pro Asp Asp Gly Ser Lys Asp Val Phe Val
                 20                  25                  30

His Phe Thr Ala Ile Gln Ser Asn Glu Phe Arg Thr Leu Asn Glu Asn
             35                  40                  45

Gln Lys Val Glu Phe Ser Ile Glu Gln Gly Gln Arg Gly Pro Ala Ala
 50                  55                  60

Ala Asn Val Val Thr Leu
 65                  70

<210> SEQ ID NO 353
<211> LENGTH: 68
<212> TYPE: PRT
<213> ORGANISM: Artificial Sequence
<220> FEATURE:
<223> OTHER INFORMATION: synthetic sequence, Chimeric
      Ec_CspD_R2_Bs_CspB_bb

<400> SEQUENCE: 353

Met Val Glu Gly Lys Val Lys Trp Phe Asn Ser Glu Lys Gly Phe Gly
 1                5                  10                  15

Phe Ile Cys Pro Glu Gly Gly Gly Glu Asp Val Phe Val His Phe Ser
                 20                  25                  30

Ala Ile Gln Gly Glu Gly Phe Lys Thr Leu Glu Glu Gly Gln Ala Val
             35                  40                  45

Ser Phe Glu Ile Val Glu Gly Asn Arg Gly Pro Gln Ala Ala Asn Val
 50                  55                  60

Thr Lys Glu Ala
 65

<210> SEQ ID NO 354
<211> LENGTH: 67
<212> TYPE: PRT
<213> ORGANISM: Artificial Sequence
<220> FEATURE:
<223> OTHER INFORMATION: synthetic sequence, Chimeric
      Tt_Csp1_R2_Bs_CspB_bb

<400> SEQUENCE: 354

Met Val Glu Gly Lys Val Lys Trp Phe Asn Ser Glu Lys Gly Phe Gly
 1                5                  10                  15

Phe Ile Glu Arg Glu Asp Gly Thr Asp Val Phe Val His Phe Ser Ala
                 20                  25                  30

Ile Gln Gly Glu Gly Phe Lys Thr Leu Glu Glu Gly Gln Ala Val Ser
             35                  40                  45

Phe Glu Ile Val Glu Gly Asn Arg Gly Pro Gln Ala Ala Asn Val Thr
```

```
                50                  55                  60

Lys Glu Ala
 65

<210> SEQ ID NO 355
<211> LENGTH: 67
<212> TYPE: PRT
<213> ORGANISM: Artificial Sequence
<220> FEATURE:
<223> OTHER INFORMATION: synthetic sequence, Chimeric
      Tt_Csp1_R3_Bs_CspB_bb

<400> SEQUENCE: 355

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Glu Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
 65

<210> SEQ ID NO 356
<211> LENGTH: 65
<212> TYPE: PRT
<213> ORGANISM: Artificial Sequence
<220> FEATURE:
<223> OTHER INFORMATION: synthetic sequence, Chimeric
      Ab_Csp2_R3_Bs_CspB_bb

<400> SEQUENCE: 356

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gly Phe Gly Gly Ser Leu Glu Glu Gly Gln Ala Val Ser Phe Glu
            35                  40                  45

Ile Val Glu Gly Asn Arg Gly Pro Gln Ala Ala Asn Val Thr Lys Glu
        50                  55                  60

Ala
 65

<210> SEQ ID NO 357
<211> LENGTH: 67
<212> TYPE: PRT
<213> ORGANISM: Artificial Sequence
<220> FEATURE:
<223> OTHER INFORMATION: synthetic sequence, Chimeric
      Ec_CspC_R3_Bs_CspB_bb

<400> SEQUENCE: 357

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Asn Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60
```

Lys Glu Ala
65

<210> SEQ ID NO 358
<211> LENGTH: 67
<212> TYPE: PRT
<213> ORGANISM: Artificial Sequence
<220> FEATURE:
<223> OTHER INFORMATION: synthetic sequence, Chimeric
      Ec_CspD_R3_Bs_CspB_bb

<400> SEQUENCE: 358

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Met Asp Gly Tyr Arg Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 359
<211> LENGTH: 68
<212> TYPE: PRT
<213> ORGANISM: Artificial Sequence
<220> FEATURE:
<223> OTHER INFORMATION: synthetic sequence, Chimeric
      Ec_CspC_R2_Bs_CspB_bb

<400> SEQUENCE: 359

Met Val Glu Gly Lys Val Lys Trp Phe Asn Ser Glu Lys Gly Phe Gly
1               5                   10                  15

Phe Ile Thr Pro Ala Asp Gly Ser Lys Asp Val Phe Val His Phe Ser
            20                  25                  30

Ala Ile Gln Gly Glu Gly Phe Lys Thr Leu Glu Glu Gly Gln Ala Val
        35                  40                  45

Ser Phe Glu Ile Val Glu Gly Asn Arg Gly Pro Gln Ala Ala Asn Val
    50                  55                  60

Thr Lys Glu Ala
65

<210> SEQ ID NO 360
<211> LENGTH: 68
<212> TYPE: PRT
<213> ORGANISM: Artificial Sequence
<220> FEATURE:
<223> OTHER INFORMATION: synthetic sequence, Chimeric
      Ab_Csp2_R2_Bs_CspB_bb

<400> SEQUENCE: 360

Met Val Glu Gly Lys Val Lys Trp Phe Asn Ser Glu Lys Gly Phe Gly
1               5                   10                  15

Phe Ile Thr Pro Asp Asn Gly Gly Pro Asp Val Phe Val His Phe Ser
            20                  25                  30

Ala Ile Gln Gly Glu Gly Phe Lys Thr Leu Glu Glu Gly Gln Ala Val
        35                  40                  45

Ser Phe Glu Ile Val Glu Gly Asn Arg Gly Pro Gln Ala Ala Asn Val
    50                  55                  60

Thr Lys Glu Ala
65

<210> SEQ ID NO 361
<211> LENGTH: 69
<212> TYPE: PRT
<213> ORGANISM: Artificial Sequence
<220> FEATURE:
<223> OTHER INFORMATION: synthetic sequence, Chimeric
      Tm_Csp1_R3_Ec_CspC_bb

<400> SEQUENCE: 361

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
                20                  25                  30

Phe Ser Ala Ile Glu Met Glu Gly Phe Lys Thr Leu Ala Glu Gly Gln
            35                  40                  45

Asn Val Glu Phe Glu Ile Gln Asp Gly Gln Lys Gly Pro Ala Ala Val
    50                  55                  60

Asn Val Thr Ala Ile
65

<210> SEQ ID NO 362
<211> LENGTH: 69
<212> TYPE: PRT
<213> ORGANISM: Artificial Sequence
<220> FEATURE:
<223> OTHER INFORMATION: synthetic sequence, Chimeric
      Bs_CspB_R3_Ec_CspC_bb

<400> SEQUENCE: 362

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
                20                  25                  30

Phe Ser Ala Ile Gln Gly Glu Gly Phe Lys Thr Leu Ala Glu Gly Gln
            35                  40                  45

Asn Val Glu Phe Glu Ile Gln Asp Gly Gln Lys Gly Pro Ala Ala Val
    50                  55                  60

Asn Val Thr Ala Ile
65

<210> SEQ ID NO 363
<211> LENGTH: 69
<212> TYPE: PRT
<213> ORGANISM: Artificial Sequence
<220> FEATURE:
<223> OTHER INFORMATION: synthetic sequence, Chimeric
      Ec_CspD_R4_Ec_CspC_bb

<400> SEQUENCE: 363

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
                20                  25                  30

Phe Ser Ala Ile Gln Gly Asn Gly Phe Lys Thr Leu Ala Glu Gly Gln
            35                  40                  45

Asn Val Glu Phe Asp Val His Gln Gly Pro Lys Gly Pro Ala Ala Val
    50                  55                  60

Asn Val Thr Ala Ile

<210> SEQ ID NO 364
<211> LENGTH: 69
<212> TYPE: PRT
<213> ORGANISM: Artificial Sequence
<220> FEATURE:
<223> OTHER INFORMATION: synthetic sequence, Chimeric
      Bs_CspB_R5_Ec_CspC_bb

<400> SEQUENCE: 364

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
                20                  25                  30

Phe Ser Ala Ile Gln Gly Asn Gly Phe Lys Thr Leu Ala Glu Gly Gln
            35                  40                  45

Asn Val Glu Phe Glu Ile Gln Asp Gly Gln Lys Gly Pro Gln Ala Ala
        50                  55                  60

Asn Val Thr Lys Glu
65

<210> SEQ ID NO 365
<211> LENGTH: 69
<212> TYPE: PRT
<213> ORGANISM: Artificial Sequence
<220> FEATURE:
<223> OTHER INFORMATION: synthetic sequence, Chimeric
      Tm_Csp1_R4_Ec_CspC_bb

<400> SEQUENCE: 365

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
                20                  25                  30

Phe Ser Ala Ile Gln Gly Asn Gly Phe Lys Thr Leu Ala Glu Gly Gln
            35                  40                  45

Asn Val Glu Phe Glu Ile Gln Glu Gly Lys Lys Gly Pro Ala Ala Val
        50                  55                  60

Asn Val Thr Ala Ile
65

<210> SEQ ID NO 366
<211> LENGTH: 69
<212> TYPE: PRT
<213> ORGANISM: Artificial Sequence
<220> FEATURE:
<223> OTHER INFORMATION: synthetic sequence, Chimeric
      Bs_CspB_R4_Ec_CspC_bb

<400> SEQUENCE: 366

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
                20                  25                  30

Phe Ser Ala Ile Gln Gly Asn Gly Phe Lys Thr Leu Ala Glu Gly Gln
            35                  40                  45

Asn Val Glu Phe Glu Ile Val Glu Gly Asn Arg Gly Pro Ala Ala Val
        50                  55                  60

Asn Val Thr Ala Ile
65

```
<210> SEQ ID NO 367
<211> LENGTH: 69
<212> TYPE: PRT
<213> ORGANISM: Artificial Sequence
<220> FEATURE:
<223> OTHER INFORMATION: synthetic sequence, Chimeric
      Ab_Csp2_R4_Ec_CspC_bb

<400> SEQUENCE: 367

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Leu Gly Gln Asp Arg Lys Gly Pro Ala Ala Val
    50                  55                  60

Asn Val Thr Ala Ile
65

<210> SEQ ID NO 368
<211> LENGTH: 69
<212> TYPE: PRT
<213> ORGANISM: Artificial Sequence
<220> FEATURE:
<223> OTHER INFORMATION: synthetic sequence, Chimeric
      Tt_Csp1_R4_Ec_CspC_bb

<400> SEQUENCE: 368

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Val Val Gln Ala Ala Lys Gly Pro Ala Ala Val
    50                  55                  60

Asn Val Thr Ala Ile
65

<210> SEQ ID NO 369
<211> LENGTH: 69
<212> TYPE: PRT
<213> ORGANISM: Artificial Sequence
<220> FEATURE:
<223> OTHER INFORMATION: synthetic sequence, Chimeric
      Ec_CspG_R4_Ec_CspC_bb

<400> SEQUENCE: 369

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Ser Ile Glu Gln Gly Gln Arg Gly Pro Ala Ala Val
    50                  55                  60

Asn Val Thr Ala Ile
65
```

-continued

<210> SEQ ID NO 370
<211> LENGTH: 69
<212> TYPE: PRT
<213> ORGANISM: Artificial Sequence
<220> FEATURE:
<223> OTHER INFORMATION: synthetic sequence, Chimeric
      Tt_Csp1_R3_Ab_Csp2_bb

<400> SEQUENCE: 370

Met Ala Thr Gly Thr Val Lys Phe Phe Ala Gln Asp Lys Gly Phe Gly
1               5                   10                  15

Phe Ile Thr Pro Asp Asn Gly Gly Pro Asp Val Phe Val His Ile Ser
            20                  25                  30

Ala Val Glu Gly Glu Gly Phe Lys Thr Leu Gln Asp Gly Gln Lys Val
        35                  40                  45

Ser Tyr Glu Leu Gly Gln Asp Arg Lys Thr Gly Lys Ser Lys Ala Glu
    50                  55                  60

Asn Val Thr Leu Leu
65

<210> SEQ ID NO 371
<211> LENGTH: 67
<212> TYPE: PRT
<213> ORGANISM: Artificial Sequence
<220> FEATURE:
<223> OTHER INFORMATION: synthetic sequence, Chimeric
      Tm_Csp1_R4_Ab_Csp2_bb

<400> SEQUENCE: 371

Met Ala Thr Gly Thr Val Lys Phe Phe Ala Gln Asp Lys Gly Phe Gly
1               5                   10                  15

Phe Ile Thr Pro Asp Asn Gly Gly Pro Asp Val Phe Val His Ile Ser
            20                  25                  30

Ala Val Gly Phe Gly Gly Ser Leu Gln Asp Gly Gln Lys Val Ser Tyr
        35                  40                  45

Glu Ile Gln Glu Gly Lys Lys Thr Gly Lys Ser Lys Ala Glu Asn Val
    50                  55                  60

Thr Leu Leu
65

<210> SEQ ID NO 372
<211> LENGTH: 69
<212> TYPE: PRT
<213> ORGANISM: Artificial Sequence
<220> FEATURE:
<223> OTHER INFORMATION: synthetic sequence, Chimeric
      Ec_CspD_R3_Ab_Csp2_bb

<400> SEQUENCE: 372

Met Ala Thr Gly Thr Val Lys Phe Phe Ala Gln Asp Lys Gly Phe Gly
1               5                   10                  15

Phe Ile Thr Pro Asp Asn Gly Gly Pro Asp Val Phe Val His Ile Ser
            20                  25                  30

Ala Val Gln Met Asp Gly Tyr Arg Thr Leu Gln Asp Gly Gln Lys Val
        35                  40                  45

Ser Tyr Glu Leu Gly Gln Asp Arg Lys Thr Gly Lys Ser Lys Ala Glu
    50                  55                  60

Asn Val Thr Leu Leu
65

<210> SEQ ID NO 373
<211> LENGTH: 74
<212> TYPE: PRT
<213> ORGANISM: Artificial Sequence
<220> FEATURE:
<223> OTHER INFORMATION: synthetic sequence, Chimeric
      Ec_CspC_R3_Ec_CspD_bb

<400> SEQUENCE: 373

```
Met Glu Lys Gly Thr Val Lys Trp Phe Asn Asn Ala Lys Gly Phe Gly
1               5                   10                  15

Phe Ile Cys Pro Glu Gly Gly Gly Glu Asp Ile Phe Ala His Tyr Ser
                20                  25                  30

Thr Ile Gln Gly Asn Gly Phe Lys Thr Leu Lys Ala Gly Gln Ser Val
            35                  40                  45

Gln Phe Asp Val His Gln Gly Pro Lys Gly Asn His Ala Ser Val Ile
        50                  55                  60

Val Pro Val Glu Val Glu Ala Ala Val Ala
65                  70
```

<210> SEQ ID NO 374
<211> LENGTH: 74
<212> TYPE: PRT
<213> ORGANISM: Artificial Sequence
<220> FEATURE:
<223> OTHER INFORMATION: synthetic sequence, Chimeric
      Ec_CspC_R5_Ec_CspD_bb

<400> SEQUENCE: 374

```
Met Glu Lys Gly Thr Val Lys Trp Phe Asn Asn Ala Lys Gly Phe Gly
1               5                   10                  15

Phe Ile Cys Pro Glu Gly Gly Gly Glu Asp Ile Phe Ala His Tyr Ser
                20                  25                  30

Thr Ile Gln Met Asp Gly Tyr Arg Thr Leu Lys Ala Gly Gln Ser Val
            35                  40                  45

Gln Phe Asp Val His Gln Gly Pro Lys Gly Asn Ala Ala Val Asn Val
        50                  55                  60

Thr Ala Ile Glu Val Glu Ala Ala Val Ala
65                  70
```

<210> SEQ ID NO 375
<211> LENGTH: 74
<212> TYPE: PRT
<213> ORGANISM: Artificial Sequence
<220> FEATURE:
<223> OTHER INFORMATION: synthetic sequence, Chimeric
      Tm_Csp1_R5_Ec_CspC_bb

<400> SEQUENCE: 375

```
Met Glu Lys Gly Thr Val Lys Trp Phe Asn Asn Ala Lys Gly Phe Gly
1               5                   10                  15

Phe Ile Cys Pro Glu Gly Gly Gly Glu Asp Ile Phe Ala His Tyr Ser
                20                  25                  30

Thr Ile Gln Met Asp Gly Tyr Arg Thr Leu Lys Ala Gly Gln Ser Val
            35                  40                  45

Gln Phe Asp Val His Gln Gly Pro Lys Gly Asn Gln Ala Ala Asn Val
        50                  55                  60

Thr Lys Glu Glu Val Glu Ala Ala Val Ala
65                  70
```

<210> SEQ ID NO 376

<211> LENGTH: 74
<212> TYPE: PRT
<213> ORGANISM: Artificial Sequence
<220> FEATURE:
<223> OTHER INFORMATION: synthetic sequence, Chimeric
      Tt_Csp1_R5_Ec_CspD_bb

<400> SEQUENCE: 376

Met Glu Lys Gly Thr Val Lys Trp Phe Asn Asn Ala Lys Gly Phe Gly
1               5                   10                  15

Phe Ile Cys Pro Glu Gly Gly Gly Glu Asp Ile Phe Ala His Tyr Ser
                20                  25                  30

Thr Ile Gln Met Asp Gly Tyr Arg Thr Leu Lys Ala Gly Gln Ser Val
            35                  40                  45

Gln Phe Asp Val His Gln Gly Pro Lys Gly Asn Gln Ala Ser Lys Val
        50                  55                  60

Arg Lys Leu Glu Val Glu Ala Ala Val Ala
65                  70

<210> SEQ ID NO 377
<211> LENGTH: 74
<212> TYPE: PRT
<213> ORGANISM: Artificial Sequence
<220> FEATURE:
<223> OTHER INFORMATION: synthetic sequence, Chimeric
      Tm_Csp1_R4_Ec_CspD_bb

<400> SEQUENCE: 377

Met Glu Lys Gly Thr Val Lys Trp Phe Asn Asn Ala Lys Gly Phe Gly
1               5                   10                  15

Phe Ile Cys Pro Glu Gly Gly Gly Glu Asp Ile Phe Ala His Tyr Ser
                20                  25                  30

Thr Ile Gln Met Asp Gly Tyr Arg Thr Leu Lys Ala Gly Gln Ser Val
35                  40                  45

Gln Phe Glu Ile Gln Glu Gly Lys Lys Gly Asn His Ala Ser Val Ile
            50                  55                  60

Val Pro Val Glu Val Glu Ala Ala Val Ala
65                  70

<210> SEQ ID NO 378
<211> LENGTH: 74
<212> TYPE: PRT
<213> ORGANISM: Artificial Sequence
<220> FEATURE:
<223> OTHER INFORMATION: synthetic sequence, Chimeric
      Bs_CspB_R4_Ec_CspD_bb

<400> SEQUENCE: 378

Met Glu Lys Gly Thr Val Lys Trp Phe Asn Asn Ala Lys Gly Phe Gly
1               5                   10                  15

Phe Ile Cys Pro Glu Gly Gly Gly Glu Asp Ile Phe Ala His Tyr Ser
                20                  25                  30

Thr Ile Gln Met Asp Gly Tyr Arg Thr Leu Lys Ala Gly Gln Ser Val
            35                  40                  45

Gln Phe Glu Ile Val Glu Gly Asn Arg Gly Asn His Ala Ser Val Ile
        50                  55                  60

Val Pro Val Glu Val Glu Ala Ala Val Ala
65                  70

<210> SEQ ID NO 379
<211> LENGTH: 74

<212> TYPE: PRT
<213> ORGANISM: Artificial Sequence
<220> FEATURE:
<223> OTHER INFORMATION: synthetic sequence, Chimeric
    Ab_Csp2_R4_Ec_CspD_bb

<400> SEQUENCE: 379

Met Glu Lys Gly Thr Val Lys Trp Phe Asn Asn Ala Lys Gly Phe Gly
1               5                   10                  15

Phe Ile Cys Pro Glu Gly Gly Glu Asp Ile Phe Ala His Tyr Ser
                20                  25                  30

Thr Ile Gln Met Asp Gly Tyr Arg Thr Leu Lys Ala Gly Gln Ser Val
            35                  40                  45

Gln Phe Glu Leu Gly Gln Asp Arg Lys Gly Asn His Ala Ser Val Ile
    50                  55                  60

Val Pro Val Glu Val Glu Ala Ala Val Ala
65                  70

<210> SEQ ID NO 380
<211> LENGTH: 74
<212> TYPE: PRT
<213> ORGANISM: Artificial Sequence
<220> FEATURE:
<223> OTHER INFORMATION: synthetic sequence, Chimeric
    Tt_Csp1_R4_Ec_CspD_bb

<400> SEQUENCE: 380

Met Glu Lys Gly Thr Val Lys Trp Phe Asn Asn Ala Lys Gly Phe Gly
1               5                   10                  15

Phe Ile Cys Pro Glu Gly Gly Glu Asp Ile Phe Ala His Tyr Ser
                20                  25                  30

Thr Ile Gln Met Asp Gly Tyr Arg Thr Leu Lys Ala Gly Gln Ser Val
            35                  40                  45

Gln Phe Glu Val Val Gln Ala Ala Lys Gly Asn His Ala Ser Val Ile
    50                  55                  60

Val Pro Val Glu Val Glu Ala Ala Val Ala
65                  70

<210> SEQ ID NO 381
<211> LENGTH: 74
<212> TYPE: PRT
<213> ORGANISM: Artificial Sequence
<220> FEATURE:
<223> OTHER INFORMATION: synthetic sequence, Chimeric
    Ec_CspG_R4_Ec_CspD_bb

<400> SEQUENCE: 381

Met Glu Lys Gly Thr Val Lys Trp Phe Asn Asn Ala Lys Gly Phe Gly
1               5                   10                  15

Phe Ile Cys Pro Glu Gly Gly Glu Asp Ile Phe Ala His Tyr Ser
                20                  25                  30

Thr Ile Gln Met Asp Gly Tyr Arg Thr Leu Lys Ala Gly Gln Ser Val
            35                  40                  45

Gln Phe Ser Ile Glu Gln Gly Gln Arg Gly Asn His Ala Ser Val Ile
    50                  55                  60

Val Pro Val Glu Val Glu Ala Ala Val Ala
65                  70

<210> SEQ ID NO 382
<211> LENGTH: 66
<212> TYPE: PRT

```
<213> ORGANISM: Artificial Sequence
<220> FEATURE:
<223> OTHER INFORMATION: synthetic sequence, Chimeric
      Tt_Csp1_R3_Tm_Csp1_bb

<400> SEQUENCE: 382

Met Arg Gly Lys Val Lys Trp Phe Asp Ser Lys Gly Tyr Gly Phe
1               5                   10                  15

Ile Thr Lys Asp Glu Gly Gly Asp Val Phe Val His Trp Ser Ala Ile
                20                  25                  30

Glu Gly Glu Gly Phe Lys Thr Leu Lys Glu Gly Gln Val Val Glu Phe
            35                  40                  45

Glu Ile Gln Glu Gly Lys Lys Gly Pro Gln Ala Ala His Val Lys Val
        50                  55                  60

Val Glu
65

<210> SEQ ID NO 383
<211> LENGTH: 66
<212> TYPE: PRT
<213> ORGANISM: Artificial Sequence
<220> FEATURE:
<223> OTHER INFORMATION: synthetic sequence, Chimeric
      Ab_Csp2_R4_Tm_Csp1_bb

<400> SEQUENCE: 383

Met Arg Gly Lys Val Lys Trp Phe Asp Ser Lys Gly Tyr Gly Phe
1               5                   10                  15

Ile Thr Lys Asp Glu Gly Gly Asp Val Phe Val His Trp Ser Ala Ile
                20                  25                  30

Glu Met Glu Gly Phe Lys Thr Leu Lys Glu Gly Gln Val Val Glu Phe
            35                  40                  45

Glu Leu Gly Gln Asp Arg Lys Gly Pro Gln Ala Ala His Val Lys Val
        50                  55                  60

Val Glu
65

<210> SEQ ID NO 384
<211> LENGTH: 66
<212> TYPE: PRT
<213> ORGANISM: Artificial Sequence
<220> FEATURE:
<223> OTHER INFORMATION: synthetic sequence, Chimeric
      Ec_CspG_R4_Tm_Csp1_bb

<400> SEQUENCE: 384

Met Arg Gly Lys Val Lys Trp Phe Asp Ser Lys Gly Tyr Gly Phe
1               5                   10                  15

Ile Thr Lys Asp Glu Gly Gly Asp Val Phe Val His Trp Ser Ala Ile
                20                  25                  30

Glu Met Glu Gly Phe Lys Thr Leu Lys Glu Gly Gln Val Val Glu Phe
            35                  40                  45

Ser Ile Glu Gln Gly Gln Arg Gly Pro Gln Ala Ala His Val Lys Val
        50                  55                  60

Val Glu
65

<210> SEQ ID NO 385
<211> LENGTH: 64
<212> TYPE: PRT
<213> ORGANISM: Artificial Sequence
```

<220> FEATURE:
<223> OTHER INFORMATION: synthetic sequence, Chimeric
    Ab_Csp2_R3_Tm_Csp1_bb

<400> SEQUENCE: 385

Met Arg Gly Lys Val Lys Trp Phe Asp Ser Lys Lys Gly Tyr Gly Phe
1               5                   10                  15

Ile Thr Lys Asp Glu Gly Gly Asp Val Phe Val His Trp Ser Ala Ile
            20                  25                  30

Gly Phe Gly Gly Ser Leu Lys Glu Gly Gln Val Val Glu Phe Glu Ile
        35                  40                  45

Gln Glu Gly Lys Lys Gly Pro Gln Ala Ala His Val Lys Val Val Glu
    50                  55                  60

<210> SEQ ID NO 386
<211> LENGTH: 66
<212> TYPE: PRT
<213> ORGANISM: Artificial Sequence
<220> FEATURE:
<223> OTHER INFORMATION: synthetic sequence, Chimeric
    Ec_CspC_R3_Tm_Csp1_bb

<400> SEQUENCE: 386

Met Arg Gly Lys Val Lys Trp Phe Asp Ser Lys Lys Gly Tyr Gly Phe
1               5                   10                  15

Ile Thr Lys Asp Glu Gly Gly Asp Val Phe Val His Trp Ser Ala Ile
            20                  25                  30

Gln Gly Asn Gly Phe Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 387
<211> LENGTH: 66
<212> TYPE: PRT
<213> ORGANISM: Artificial Sequence
<220> FEATURE:
<223> OTHER INFORMATION: synthetic sequence, Chimeric
    Ec_CspD_R3_Tm_Csp1_bb

<400> SEQUENCE: 387

Met Arg Gly Lys Val Lys Trp Phe Asp Ser Lys Lys Gly Tyr Gly Phe
1               5                   10                  15

Ile Thr Lys Asp Glu Gly Gly Asp Val Phe Val His Trp Ser Ala Ile
            20                  25                  30

Gln Met Asp Gly Tyr Arg Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 388
<211> LENGTH: 70
<212> TYPE: PRT
<213> ORGANISM: Artificial Sequence
<220> FEATURE:
<223> OTHER INFORMATION: synthetic sequence, Chimeric
    Ec_CspC_R4_Ec_CspG_bb

<400> SEQUENCE: 388

Met Ser Asn Lys Met Thr Gly Leu Val Lys Trp Phe Asn Ala Asp Lys
1               5                   10                  15

Gly Phe Gly Phe Ile Thr Pro Asp Asp Gly Ser Lys Asp Val Phe Val
                20                  25                  30

His Phe Thr Ala Ile Gln Ser Asn Glu Phe Arg Thr Leu Asn Glu Asn
            35                  40                  45

Gln Lys Val Glu Phe Glu Ile Gln Asp Gly Lys Gly Pro Ala Ala
    50                  55                  60

Ala Asn Val Val Thr Leu
65                  70

<210> SEQ ID NO 389
<211> LENGTH: 70
<212> TYPE: PRT
<213> ORGANISM: Artificial Sequence
<220> FEATURE:
<223> OTHER INFORMATION: synthetic sequence, Chimeric
      Tm_Csp1_R5_Ec_CspG_bb

<400> SEQUENCE: 389

Met Ser Asn Lys Met Thr Gly Leu Val Lys Trp Phe Asn Ala Asp Lys
1               5                   10                  15

Gly Phe Gly Phe Ile Thr Pro Asp Asp Gly Ser Lys Asp Val Phe Val
                20                  25                  30

His Phe Thr Ala Ile Gln Ser Asn Glu Phe Arg Thr Leu Asn Glu Asn
            35                  40                  45

Gln Lys Val Glu Phe Ser Ile Glu Gln Gly Gln Arg Gly Pro Gln Ala
    50                  55                  60

Ala His Val Lys Val Val
65                  70

<210> SEQ ID NO 390
<211> LENGTH: 70
<212> TYPE: PRT
<213> ORGANISM: Artificial Sequence
<220> FEATURE:
<223> OTHER INFORMATION: synthetic sequence, Chimeric
      Ec_CspD_R5_Tm_Csp1_bb

<400> SEQUENCE: 390

Met Ser Asn Lys Met Thr Gly Leu Val Lys Trp Phe Asn Ala Asp Lys
1               5                   10                  15

Gly Phe Gly Phe Ile Thr Pro Asp Asp Gly Ser Lys Asp Val Phe Val
                20                  25                  30

His Phe Thr Ala Ile Gln Ser Asn Glu Phe Arg Thr Leu Asn Glu Asn
            35                  40                  45

Gln Lys Val Glu Phe Ser Ile Glu Gln Gly Gln Arg Gly Pro Gln Ala
    50                  55                  60

Ala His Val Lys Val Val
65                  70

<210> SEQ ID NO 391
<211> LENGTH: 70
<212> TYPE: PRT
<213> ORGANISM: Artificial Sequence
<220> FEATURE:
<223> OTHER INFORMATION: synthetic sequence, Chimeric
      Bs_CspB_R5_Ec_CspG_bb

<400> SEQUENCE: 391

Met Ser Asn Lys Met Thr Gly Leu Val Lys Trp Phe Asn Ala Asp Lys
1               5                   10                  15

Gly Phe Gly Phe Ile Thr Pro Asp Asp Gly Ser Lys Asp Val Phe Val
            20                  25                  30

His Phe Thr Ala Ile Gln Ser Asn Glu Phe Arg Thr Leu Asn Glu Asn
        35                  40                  45

Gln Lys Val Glu Phe Ser Ile Glu Gln Gly Gln Arg Gly Pro Gln Ala
    50                  55                  60

Ala Asn Val Thr Lys Glu
65                  70

<210> SEQ ID NO 392
<211> LENGTH: 66
<212> TYPE: PRT
<213> ORGANISM: Artificial Sequence
<220> FEATURE:
<223> OTHER INFORMATION: synthetic sequence, Chimeric
      Ec_CspC_R4_Tt_Csp1_bb

<400> SEQUENCE: 392

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Ile Gln Asp Gly Gln Lys Gly Pro Gln Ala Ser Lys Val Arg
    50                  55                  60

Lys Leu
65

<210> SEQ ID NO 393
<211> LENGTH: 66
<212> TYPE: PRT
<213> ORGANISM: Artificial Sequence
<220> FEATURE:
<223> OTHER INFORMATION: synthetic sequence, Chimeric
      Tm_Csp1_R4_Tt_Csp1_bb

<400> SEQUENCE: 393

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Ile Gln Glu Gly Lys Lys Gly Pro Gln Ala Ser Lys Val Arg
    50                  55                  60

Lys Leu
65

<210> SEQ ID NO 394
<211> LENGTH: 66
<212> TYPE: PRT
<213> ORGANISM: Artificial Sequence
<220> FEATURE:
<223> OTHER INFORMATION: synthetic sequence, Chimeric
      Ab_Csp2_R4_Tt_Csp1_bb

<400> SEQUENCE: 394

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Leu Gly Gln Asp Arg Lys Gly Pro Gln Ala Ser Lys Val Arg
    50                  55                  60

Lys Leu
65

<210> SEQ ID NO 395
<211> LENGTH: 66
<212> TYPE: PRT
<213> ORGANISM: Artificial Sequence
<220> FEATURE:
<223> OTHER INFORMATION: synthetic sequence, Chimeric
      Ec_CspC_R5_Tt_Csp1_bb

<400> SEQUENCE: 395

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Val Val Gln Ala Ala Lys Gly Pro Ala Ala Val Asn Val Thr
    50                  55                  60

Ala Ile
65

<210> SEQ ID NO 396
<211> LENGTH: 66
<212> TYPE: PRT
<213> ORGANISM: Artificial Sequence
<220> FEATURE:
<223> OTHER INFORMATION: synthetic sequence, Chimeric
      Ec_CspG_R4_Tt_Csp1_bb

<400> SEQUENCE: 396

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Ser Ile Glu Gln Gly Gln Arg Gly Pro Gln Ala Ser Lys Val Arg
    50                  55                  60

Lys Leu
65

<210> SEQ ID NO 397
<211> LENGTH: 64
<212> TYPE: PRT
<213> ORGANISM: Artificial Sequence
<220> FEATURE:
<223> OTHER INFORMATION: synthetic sequence, Chimeric
      Ab_Csp2_R3_Tt_Csp1_bb

<400> SEQUENCE: 397

Met Val Arg Gly Lys Val Lys Trp Phe Asn Ala Glu Lys Gly Tyr Gly

```
1               5                   10                  15
Phe Ile Glu Arg Glu Asp Gly Thr Asp Val Phe Val His Tyr Ser Ala
            20                  25                  30

Ile Gly Phe Gly Gly Ser Leu Glu Glu Gly Gln Ala Val Glu Phe Glu
        35                  40                  45

Val Val Gln Ala Ala Lys Gly Pro Gln Ala Ser Lys Val Arg Lys Leu
    50                  55                  60

<210> SEQ ID NO 398
<211> LENGTH: 66
<212> TYPE: PRT
<213> ORGANISM: Artificial Sequence
<220> FEATURE:
<223> OTHER INFORMATION: synthetic sequence, Chimeric
      Bs_CspB_R3_Tt_Csp1_bb

<400> SEQUENCE: 398

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Gln Gly Glu Gly Phe Lys Thr Leu Glu Glu Gly Gln Ala Val Glu
        35                  40                  45

Phe Glu Val Val Gln Ala Ala Lys Gly Pro Gln Ala Ser Lys Val Arg
    50                  55                  60

Lys Leu
65

<210> SEQ ID NO 399
<211> LENGTH: 66
<212> TYPE: PRT
<213> ORGANISM: Artificial Sequence
<220> FEATURE:
<223> OTHER INFORMATION: synthetic sequence, Chimeric
      Ec_CspC_R3_Tt_Csp1_bb

<400> SEQUENCE: 399

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Gln Gly Asn Gly Phe Lys Thr Leu Glu Glu Gly Gln Ala Val Glu
        35                  40                  45

Phe Glu Val Val Gln Ala Ala Lys Gly Pro Gln Ala Ser Lys Val Arg
    50                  55                  60

Lys Leu
65

<210> SEQ ID NO 400
<211> LENGTH: 66
<212> TYPE: PRT
<213> ORGANISM: Artificial Sequence
<220> FEATURE:
<223> OTHER INFORMATION: synthetic sequence, Chimeric
      Ec_CspG_R3_Tt_Csp1_bb

<400> SEQUENCE: 400

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30
```

```
Ile Gln Ser Asn Glu Phe Arg Thr Leu Glu Glu Gly Gln Ala Val Glu
            35                  40                  45

Phe Glu Val Val Gln Ala Ala Lys Gly Pro Gln Ala Ser Lys Val Arg
    50                  55                  60

Lys Leu
65

<210> SEQ ID NO 401
<211> LENGTH: 66
<212> TYPE: PRT
<213> ORGANISM: Artificial Sequence
<220> FEATURE:
<223> OTHER INFORMATION: synthetic sequence, Chimeric
      Tm_Csp1_R2_Tt_Csp1_bb

<400> SEQUENCE: 401

Met Val Arg Gly Lys Val Lys Trp Phe Asn Ala Glu Lys Gly Tyr Gly
1               5                   10                  15

Phe Ile Thr Lys Asp Glu Gly Gly Asp Val Phe Val His Tyr Ser Ala
            20                  25                  30

Ile Glu Gly Glu Gly Phe Lys Thr Leu Glu Glu Gly Gln Ala Val Glu
            35                  40                  45

Phe Glu Val Val Gln Ala Ala Lys Gly Pro Gln Ala Ser Lys Val Arg
    50                  55                  60

Lys Leu
65

<210> SEQ ID NO 402
<211> LENGTH: 67
<212> TYPE: PRT
<213> ORGANISM: Artificial Sequence
<220> FEATURE:
<223> OTHER INFORMATION: synthetic sequence, Chimeric
      Ec_CspC_R2_Tt_Csp1_bb

<400> SEQUENCE: 402

Met Val Arg Gly Lys Val Lys Trp Phe Asn Ala Glu Lys Gly Tyr Gly
1               5                   10                  15

Phe Ile Thr Pro Ala Asp Gly Ser Lys Asp Val Phe Val His Tyr Ser
            20                  25                  30

Ala Ile Glu Gly Glu Gly Phe Lys Thr Leu Glu Glu Gly Gln Ala Val
            35                  40                  45

Glu Phe Glu Val Val Gln Ala Ala Lys Gly Pro Gln Ala Ser Lys Val
    50                  55                  60

Arg Lys Leu
65

<210> SEQ ID NO 403
<211> LENGTH: 67
<212> TYPE: PRT
<213> ORGANISM: Artificial Sequence
<220> FEATURE:
<223> OTHER INFORMATION: synthetic sequence, Chimeric
      Ec_CspG_R2_Tt_Csp1_bb

<400> SEQUENCE: 403

Met Val Arg Gly Lys Val Lys Trp Phe Asn Ala Glu Lys Gly Tyr Gly
1               5                   10                  15

Phe Ile Thr Pro Asp Asp Gly Ser Lys Asp Val Phe Val His Tyr Ser
            20                  25                  30
```

```
Ala Ile Glu Gly Glu Gly Phe Lys Thr Leu Glu Glu Gly Gln Ala Val
            35                  40                  45

Glu Phe Glu Val Val Gln Ala Ala Lys Gly Pro Gln Ala Ser Lys Val
 50                  55                  60

Arg Lys Leu
 65

<210> SEQ ID NO 404
<211> LENGTH: 66
<212> TYPE: PRT
<213> ORGANISM: Artificial Sequence
<220> FEATURE:
<223> OTHER INFORMATION: synthetic sequence, Chimeric
      Ec_CspC_R1_Tt_Csp1_bb

<400> SEQUENCE: 404

Met Val Arg Gly Lys Val Lys Trp Phe Asn Glu Ser Lys Gly Tyr Gly
 1               5                  10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
            35                  40                  45

Phe Glu Val Val Gln Ala Ala Lys Gly Pro Gln Ala Ser Lys Val Arg
 50                  55                  60

Lys Leu
 65

<210> SEQ ID NO 405
<211> LENGTH: 67
<212> TYPE: PRT
<213> ORGANISM: Artificial Sequence
<220> FEATURE:
<223> OTHER INFORMATION: synthetic sequence, Chimeric
      Tm_Csp1_R3_Bs_CspB_bb

<400> SEQUENCE: 405

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
            20                  25                  30

Ile Glu Met Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
 50                  55                  60

Lys Glu Ala
 65

<210> SEQ ID NO 406
<211> LENGTH: 67
<212> TYPE: PRT
<213> ORGANISM: Artificial Sequence
<220> FEATURE:
<223> OTHER INFORMATION: synthetic sequence, Chimeric
      Ec_CspD_R4_Bs_CspB_bb

<400> SEQUENCE: 406

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
```

```
                35                  40                  45

Phe Asp Val His Gln Gly Pro Lys Gly Pro Gln Ala Ala Asn Val Thr
    50                  55                  60

Lys Glu Ala
65

<210> SEQ ID NO 407
<211> LENGTH: 67
<212> TYPE: PRT
<213> ORGANISM: Artificial Sequence
<220> FEATURE:
<223> OTHER INFORMATION: synthetic sequence, Chimeric
      Ec_CspC_R4_Bs_CspB_bb

<400> SEQUENCE: 407

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Gln Asp Gly Gln Lys Gly Pro Gln Ala Ala Asn Val Thr
    50                  55                  60

Lys Glu Ala
65

<210> SEQ ID NO 408
<211> LENGTH: 67
<212> TYPE: PRT
<213> ORGANISM: Artificial Sequence
<220> FEATURE:
<223> OTHER INFORMATION: synthetic sequence, Chimeric
      Tm_Csp1_R4_Bs_CspB_bb

<400> SEQUENCE: 408

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Gln Glu Gly Lys Lys Gly Pro Gln Ala Ala Asn Val Thr
    50                  55                  60

Lys Glu Ala
65

<210> SEQ ID NO 409
<211> LENGTH: 67
<212> TYPE: PRT
<213> ORGANISM: Artificial Sequence
<220> FEATURE:
<223> OTHER INFORMATION: synthetic sequence, Chimeric
      Ab_Csp2_R5_Bs_CspB_bb

<400> SEQUENCE: 409

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45
```

Phe Glu Ile Val Glu Gly Asn Arg Gly Pro Lys Ala Glu Asn Val Thr
        50                  55                  60

Leu Leu Ala
 65

<210> SEQ ID NO 410
<211> LENGTH: 67
<212> TYPE: PRT
<213> ORGANISM: Artificial Sequence
<220> FEATURE:
<223> OTHER INFORMATION: synthetic sequence, Chimeric
      Ec_CspG_R4_Bs_CspB_bb

<400> SEQUENCE: 410

Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
                 20                  25                  30

Ile Gln Gly Glu Gly Phe Lys Thr Leu Glu Gly Gln Ala Val Ser
            35                  40                  45

Phe Ser Ile Glu Gln Gly Gln Arg Gly Pro Gln Ala Ala Asn Val Thr
        50                  55                  60

Lys Glu Ala
 65

<210> SEQ ID NO 411
<211> LENGTH: 66
<212> TYPE: PRT
<213> ORGANISM: Artificial Sequence
<220> FEATURE:
<223> OTHER INFORMATION: synthetic sequence, Chimeric
      Ab_Csp2_R1_Tt_Csp1_bb

<400> SEQUENCE: 411

Met Val Arg Gly Lys Val Lys Phe Phe Ala Gln Asp Lys Gly Tyr Gly
  1               5                  10                  15

Phe Ile Glu Arg Glu Asp Gly Thr Asp Val Phe Val His Tyr Ser Ala
                 20                  25                  30

Ile Glu Gly Glu Gly Phe Lys Thr Leu Glu Glu Gly Gln Ala Val Glu
            35                  40                  45

Phe Glu Val Val Gln Ala Ala Lys Gly Pro Gln Ala Ser Lys Val Arg
        50                  55                  60

Lys Leu
 65

<210> SEQ ID NO 412
<211> LENGTH: 66
<212> TYPE: PRT
<213> ORGANISM: Artificial Sequence
<220> FEATURE:
<223> OTHER INFORMATION: synthetic sequence, Chimeric
      Tm_Csp1_R1_Tt_Csp1_bb

<400> SEQUENCE: 412

Met Val Arg Gly Lys Val Lys Trp Phe Asp Ser Lys Lys Gly Tyr Gly
  1               5                  10                  15

Phe Ile Glu Arg Glu Asp Gly Thr Asp Val Phe Val His Tyr Ser Ala
                 20                  25                  30

Ile Glu Gly Glu Gly Phe Lys Thr Leu Glu Glu Gly Gln Ala Val Glu
            35                  40                  45

```
Phe Glu Val Val Gln Ala Ala Lys Gly Pro Gln Ala Ser Lys Val Arg
    50                  55                  60

Lys Leu
65

<210> SEQ ID NO 413
<211> LENGTH: 66
<212> TYPE: PRT
<213> ORGANISM: Artificial Sequence
<220> FEATURE:
<223> OTHER INFORMATION: synthetic sequence, Chimeric
      Ec_CspG_R1_Tt_Csp1_bb

<400> SEQUENCE: 413

Met Val Arg Gly Lys Val Lys Trp Phe Asn Ala Asp Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Val Val Gln Ala Ala Lys Gly Pro Gln Ala Ser Lys Val Arg
    50                  55                  60

Lys Leu
65

<210> SEQ ID NO 414
<211> LENGTH: 66
<212> TYPE: PRT
<213> ORGANISM: Artificial Sequence
<220> FEATURE:
<223> OTHER INFORMATION: synthetic sequence, Chimeric
      Ec_CspD_R4_Tt_Csp1_bb

<400> SEQUENCE: 414

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Asp Val His Gln Gly Pro Lys Gly Pro Gln Ala Ser Lys Val Arg
    50                  55                  60

Lys Leu
65

<210> SEQ ID NO 415
<211> LENGTH: 66
<212> TYPE: PRT
<213> ORGANISM: Artificial Sequence
<220> FEATURE:
<223> OTHER INFORMATION: synthetic sequence, Chimeric
      Ec_CspC_R4_Tt_Csp1_bb

<400> SEQUENCE: 415

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Ile Gln Asp Gly Gln Lys Gly Pro Gln Ala Ser Lys Val Arg
```

Lys Leu
65

<210> SEQ ID NO 416
<211> LENGTH: 66
<212> TYPE: PRT
<213> ORGANISM: Artificial Sequence
<220> FEATURE:
<223> OTHER INFORMATION: synthetic sequence, Chimeric
      Bs_CspB_R4_Tt_Csp1_bb

<400> SEQUENCE: 416

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Ile Val Glu Gly Asn Arg Gly Pro Gln Ala Ser Lys Val Arg
    50                  55                  60

Lys Leu
65

<210> SEQ ID NO 417
<211> LENGTH: 66
<212> TYPE: PRT
<213> ORGANISM: Artificial Sequence
<220> FEATURE:
<223> OTHER INFORMATION: synthetic sequence, Chimeric
      Ab_Csp2_R4_Tt_Csp1_bb

<400> SEQUENCE: 417

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Leu Gly Gln Asp Arg Lys Gly Pro Gln Ala Ser Lys Val Arg
    50                  55                  60

Lys Leu
65

<210> SEQ ID NO 418
<211> LENGTH: 66
<212> TYPE: PRT
<213> ORGANISM: Artificial Sequence
<220> FEATURE:
<223> OTHER INFORMATION: synthetic sequence, Chimeric
      Ab_Csp2_R5_Tt_Csp1_bb

<400> SEQUENCE: 418

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Val Val Gln Ala Ala Lys Gly Pro Lys Ala Glu Asn Val Thr
    50                  55                  60

Leu Leu
65

<210> SEQ ID NO 419
<211> LENGTH: 66
<212> TYPE: PRT
<213> ORGANISM: Artificial Sequence
<220> FEATURE:
<223> OTHER INFORMATION: synthetic sequence, Chimeric
      Bs_CspB_R5_Tt_Csp1_bb

<400> SEQUENCE: 419

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
                20                  25                  30

Ile Glu Gly Glu Gly Phe Lys Thr Leu Glu Glu Gly Gln Ala Val Glu
            35                  40                  45

Phe Glu Val Val Gln Ala Ala Lys Gly Pro Gln Ala Ala Asn Val Thr
        50                  55                  60

Lys Glu
65

<210> SEQ ID NO 420
<211> LENGTH: 66
<212> TYPE: PRT
<213> ORGANISM: Artificial Sequence
<220> FEATURE:
<223> OTHER INFORMATION: synthetic sequence, Chimeric
      Tm_Csp1_R3_Tt_Csp1_bb

<400> SEQUENCE: 420

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
                20                  25                  30

Ile Glu Met Glu Gly Phe Lys Thr Leu Glu Glu Gly Gln Ala Val Glu
            35                  40                  45

Phe Glu Val Val Gln Ala Ala Lys Gly Pro Gln Ala Ser Lys Val Arg
        50                  55                  60

Lys Leu
65

<210> SEQ ID NO 421
<211> LENGTH: 66
<212> TYPE: PRT
<213> ORGANISM: Artificial Sequence
<220> FEATURE:
<223> OTHER INFORMATION: synthetic sequence, Chimeric
      Bs_CspB_R3_Tt_Csp1_bb

<400> SEQUENCE: 421

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
                20                  25                  30

Ile Gln Gly Glu Gly Phe Lys Thr Leu Glu Glu Gly Gln Ala Val Glu
            35                  40                  45

Phe Glu Val Val Gln Ala Ala Lys Gly Pro Gln Ala Ser Lys Val Arg
        50                  55                  60

Lys Leu
65

<210> SEQ ID NO 422
<211> LENGTH: 66
<212> TYPE: PRT
<213> ORGANISM: Artificial Sequence
<220> FEATURE:
<223> OTHER INFORMATION: synthetic sequence, Chimeric
      Ec_CspC_R3_Tt_Csp1_bb

<400> SEQUENCE: 422

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Gln Gly Asn Gly Phe Lys Thr Leu Glu Glu Gly Gln Ala Val Glu
        35                  40                  45

Phe Glu Val Val Gln Ala Ala Lys Gly Pro Gln Ala Ser Lys Val Arg
    50                  55                  60

Lys Leu
65

<210> SEQ ID NO 423
<211> LENGTH: 66
<212> TYPE: PRT
<213> ORGANISM: Artificial Sequence
<220> FEATURE:
<223> OTHER INFORMATION: synthetic sequence, Chimeric
      Ec_CspD_R3_Tt_Csp1_bb

<400> SEQUENCE: 423

Met Val Arg Gly Lys Val Lys Trp Phe Asn Ala Glu Lys Gly Tyr Gly
1               5                   10                  15

Phe Ile Glu Arg Glu Asp Gly Thr Asp Val Phe Val His Tyr Ser Ala
            20                  25                  30

Ile Gln Met Asp Gly Tyr Arg Thr Leu Glu Glu Gly Gln Ala Val Glu
        35                  40                  45

Phe Glu Val Val Gln Ala Ala Lys Gly Pro Gln Ala Ser Lys Val Arg
    50                  55                  60

Lys Leu
65

<210> SEQ ID NO 424
<211> LENGTH: 66
<212> TYPE: PRT
<213> ORGANISM: Artificial Sequence
<220> FEATURE:
<223> OTHER INFORMATION: synthetic sequence, Chimeric
      Bs_CspB_R2_Tt_Csp1_bb

<400> SEQUENCE: 424

Met Val Arg Gly Lys Val Lys Trp Phe Asn Ala Glu Lys Gly Tyr Gly
1               5                   10                  15

Phe Ile Glu Val Glu Gly Gln Asp Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Val Val Gln Ala Ala Lys Gly Pro Gln Ala Ser Lys Val Arg
    50                  55                  60

Lys Leu

<210> SEQ ID NO 425
<211> LENGTH: 67
<212> TYPE: PRT
<213> ORGANISM: Artificial Sequence
<220> FEATURE:
<223> OTHER INFORMATION: synthetic sequence, Chimeric
      Ab_Csp2_R2_Tt_Csp1_bb

<400> SEQUENCE: 425

Met Val Arg Gly Lys Val Lys Trp Phe Asn Ala Glu Lys Gly Tyr Gly
1               5                   10                  15

Phe Ile Thr Pro Asp Asn Gly Gly Pro Asp Val Phe Val His Tyr Ser
            20                  25                  30

Ala Ile Glu Gly Glu Gly Phe Lys Thr Leu Glu Glu Gly Gln Ala Val
        35                  40                  45

Glu Phe Glu Val Val Gln Ala Ala Lys Gly Pro Gln Ala Ser Lys Val
    50                  55                  60

Arg Lys Leu
65

<210> SEQ ID NO 426
<211> LENGTH: 66
<212> TYPE: PRT
<213> ORGANISM: Artificial Sequence
<220> FEATURE:
<223> OTHER INFORMATION: synthetic sequence, Chimeric
      Ec_CspC_R1_Tt_Csp1_bb

<400> SEQUENCE: 426

Met Val Arg Gly Lys Val Lys Trp Phe Asn Glu Ser Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Val Val Gln Ala Ala Lys Gly Pro Gln Ala Ser Lys Val Arg
    50                  55                  60

Lys Leu
65

<210> SEQ ID NO 427
<211> LENGTH: 66
<212> TYPE: PRT
<213> ORGANISM: Artificial Sequence
<220> FEATURE:
<223> OTHER INFORMATION: synthetic sequence, Chimeric
      Bs_CspB_R1_Tt_Csp1_bb

<400> SEQUENCE: 427

Met Val Arg Gly Lys Val Lys Trp Phe Asn Ser Glu Lys Gly Tyr Gly
1               5                   10                  15

Phe Ile Glu Arg Glu Asp Gly Thr Asp Val Phe Val His Tyr Ser Ala
            20                  25                  30

Ile Glu Gly Glu Gly Phe Lys Thr Leu Glu Glu Gly Gln Ala Val Glu
        35                  40                  45

Phe Glu Val Val Gln Ala Ala Lys Gly Pro Gln Ala Ser Lys Val Arg
    50                  55                  60

Lys Leu
65

<210> SEQ ID NO 428
<211> LENGTH: 67
<212> TYPE: PRT
<213> ORGANISM: Artificial Sequence
<220> FEATURE:
<223> OTHER INFORMATION: synthetic sequence, Bs-CspB_S31M

<400> SEQUENCE: 428

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Met Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 429
<211> LENGTH: 67
<212> TYPE: PRT
<213> ORGANISM: Artificial Sequence
<220> FEATURE:
<223> OTHER INFORMATION: synthetic sequence, Bs-CspB_S31A

<400> SEQUENCE: 429

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ala Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 430
<211> LENGTH: 67
<212> TYPE: PRT
<213> ORGANISM: Artificial Sequence
<220> FEATURE:
<223> OTHER INFORMATION: synthetic sequence, Bs-CspB_T40L

<400> SEQUENCE: 430

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Leu Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 431
<211> LENGTH: 67

<212> TYPE: PRT
<213> ORGANISM: Artificial Sequence
<220> FEATURE:
<223> OTHER INFORMATION: synthetic sequence, Bs-CspB_T40R

<400> SEQUENCE: 431

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Arg Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 432
<211> LENGTH: 67
<212> TYPE: PRT
<213> ORGANISM: Artificial Sequence
<220> FEATURE:
<223> OTHER INFORMATION: synthetic sequence, Bs-CspB_T40W

<400> SEQUENCE: 432

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Trp Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 433
<211> LENGTH: 67
<212> TYPE: PRT
<213> ORGANISM: Artificial Sequence
<220> FEATURE:
<223> OTHER INFORMATION: synthetic sequence, Bs-CspB_S31Q

<400> SEQUENCE: 433

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Gln Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 434
<211> LENGTH: 67
<212> TYPE: PRT
<213> ORGANISM: Artificial Sequence
<220> FEATURE:
<223> OTHER INFORMATION: synthetic sequence, Bs-CspB_T40F

<400> SEQUENCE: 434

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Phe Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 435
<211> LENGTH: 67
<212> TYPE: PRT
<213> ORGANISM: Artificial Sequence
<220> FEATURE:
<223> OTHER INFORMATION: synthetic sequence, Bs-CspB_T40H

<400> SEQUENCE: 435

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys His Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 436
<211> LENGTH: 67
<212> TYPE: PRT
<213> ORGANISM: Artificial Sequence
<220> FEATURE:
<223> OTHER INFORMATION: synthetic sequence, Bs-CspB_T40K

<400> SEQUENCE: 436

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Lys Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 437
<211> LENGTH: 67
<212> TYPE: PRT
<213> ORGANISM: Artificial Sequence
<220> FEATURE:
<223> OTHER INFORMATION: synthetic sequence, Bs-CspB_S31T

<400> SEQUENCE: 437

Met Val Glu Gly Lys Val Lys Trp Phe Asn Ser Glu Lys Gly Phe Gly

```
                1               5                  10                  15
Phe Ile Glu Val Glu Gly Gln Asp Asp Val Phe Val His Phe Thr Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 438
<211> LENGTH: 67
<212> TYPE: PRT
<213> ORGANISM: Artificial Sequence
<220> FEATURE:
<223> OTHER INFORMATION: synthetic sequence, Bs-CspB_S31R

<400> SEQUENCE: 438

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Arg Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 439
<211> LENGTH: 67
<212> TYPE: PRT
<213> ORGANISM: Artificial Sequence
<220> FEATURE:
<223> OTHER INFORMATION: synthetic sequence, Bs-CspB_S31N

<400> SEQUENCE: 439

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Asn Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 440
<211> LENGTH: 67
<212> TYPE: PRT
<213> ORGANISM: Artificial Sequence
<220> FEATURE:
<223> OTHER INFORMATION: synthetic sequence, Bs-CspB_T40M

<400> SEQUENCE: 440

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30
```

```
Ile Gln Gly Glu Gly Phe Lys Met Leu Glu Glu Gly Gln Ala Val Ser
        35                  40                  45

Phe Glu Ile Val Glu Gly Asn Arg Gly Pro Gln Ala Ala Asn Val Thr
 50                  55                  60

Lys Glu Ala
 65

<210> SEQ ID NO 441
<211> LENGTH: 67
<212> TYPE: PRT
<213> ORGANISM: Artificial Sequence
<220> FEATURE:
<223> OTHER INFORMATION: synthetic sequence, Bs-CspB_T40E

<400> SEQUENCE: 441

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Glu Leu Glu Glu Gly Gln Ala Val Ser
        35                  40                  45

Phe Glu Ile Val Glu Gly Asn Arg Gly Pro Gln Ala Ala Asn Val Thr
 50                  55                  60

Lys Glu Ala
 65

<210> SEQ ID NO 442
<211> LENGTH: 67
<212> TYPE: PRT
<213> ORGANISM: Artificial Sequence
<220> FEATURE:
<223> OTHER INFORMATION: synthetic sequence, Bs-CspB_T40Y

<400> SEQUENCE: 442

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Tyr Leu Glu Glu Gly Gln Ala Val Ser
        35                  40                  45

Phe Glu Ile Val Glu Gly Asn Arg Gly Pro Gln Ala Ala Asn Val Thr
 50                  55                  60

Lys Glu Ala
 65

<210> SEQ ID NO 443
<211> LENGTH: 67
<212> TYPE: PRT
<213> ORGANISM: Artificial Sequence
<220> FEATURE:
<223> OTHER INFORMATION: synthetic sequence, Bs-CspB_S31S

<400> SEQUENCE: 443

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
        35                  40                  45
```

```
Phe Glu Ile Val Glu Gly Asn Arg Gly Pro Gln Ala Ala Asn Val Thr
    50                  55                  60

Lys Glu Ala
65

<210> SEQ ID NO 444
<211> LENGTH: 67
<212> TYPE: PRT
<213> ORGANISM: Artificial Sequence
<220> FEATURE:
<223> OTHER INFORMATION: synthetic sequence, Bs-CspB_S31Y

<400> SEQUENCE: 444

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Tyr Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 445
<211> LENGTH: 67
<212> TYPE: PRT
<213> ORGANISM: Artificial Sequence
<220> FEATURE:
<223> OTHER INFORMATION: synthetic sequence, Bs-CspB_T40D

<400> SEQUENCE: 445

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Asp Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 446
<211> LENGTH: 67
<212> TYPE: PRT
<213> ORGANISM: Artificial Sequence
<220> FEATURE:
<223> OTHER INFORMATION: synthetic sequence, Bs-CspB_T40I

<400> SEQUENCE: 446

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Ile Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
```

<210> SEQ ID NO 447
<211> LENGTH: 67
<212> TYPE: PRT
<213> ORGANISM: Artificial Sequence
<220> FEATURE:
<223> OTHER INFORMATION: synthetic sequence, Bs-CspB_S31W

<400> SEQUENCE: 447

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Trp Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 448
<211> LENGTH: 67
<212> TYPE: PRT
<213> ORGANISM: Artificial Sequence
<220> FEATURE:
<223> OTHER INFORMATION: synthetic sequence, Bs-CspB_T40V

<400> SEQUENCE: 448

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Val Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 449
<211> LENGTH: 67
<212> TYPE: PRT
<213> ORGANISM: Artificial Sequence
<220> FEATURE:
<223> OTHER INFORMATION: synthetic sequence, Bs-CspB_T40C

<400> SEQUENCE: 449

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Cys Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 450

```
<211> LENGTH: 67
<212> TYPE: PRT
<213> ORGANISM: Artificial Sequence
<220> FEATURE:
<223> OTHER INFORMATION: synthetic sequence, Bs-CspB_S31L

<400> SEQUENCE: 450

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Leu Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 451
<211> LENGTH: 67
<212> TYPE: PRT
<213> ORGANISM: Artificial Sequence
<220> FEATURE:
<223> OTHER INFORMATION: synthetic sequence, Bs-CspB_S31I

<400> SEQUENCE: 451

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ile Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 452
<211> LENGTH: 67
<212> TYPE: PRT
<213> ORGANISM: Artificial Sequence
<220> FEATURE:
<223> OTHER INFORMATION: synthetic sequence, Bs-CspB_T40G

<400> SEQUENCE: 452

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Gly Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 453
<211> LENGTH: 67
<212> TYPE: PRT
<213> ORGANISM: Artificial Sequence
<220> FEATURE:
```

<223> OTHER INFORMATION: synthetic sequence, Bs-CspB_S31E

<400> SEQUENCE: 453

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Glu Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 454
<211> LENGTH: 67
<212> TYPE: PRT
<213> ORGANISM: Artificial Sequence
<220> FEATURE:
<223> OTHER INFORMATION: synthetic sequence, Bs-CspB_T40Q

<400> SEQUENCE: 454

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Gln Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 455
<211> LENGTH: 67
<212> TYPE: PRT
<213> ORGANISM: Artificial Sequence
<220> FEATURE:
<223> OTHER INFORMATION: synthetic sequence, Bs-CspB_S31D

<400> SEQUENCE: 455

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Asp Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 456
<211> LENGTH: 67
<212> TYPE: PRT
<213> ORGANISM: Artificial Sequence
<220> FEATURE:
<223> OTHER INFORMATION: synthetic sequence, Bs-CspB_T40S

<400> SEQUENCE: 456

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Glu Glu Gly Gln Ala Val Ser
            35                  40                  45

Phe Glu Ile Val Glu Gly Asn Arg Gly Pro Gln Ala Ala Asn Val Thr
            50                  55                  60

Lys Glu Ala
65

<210> SEQ ID NO 457
<211> LENGTH: 67
<212> TYPE: PRT
<213> ORGANISM: Artificial Sequence
<220> FEATURE:
<223> OTHER INFORMATION: synthetic sequence, Bs-CspB_T40N

<400> SEQUENCE: 457

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Asn Leu Glu Glu Gly Gln Ala Val Ser
            35                  40                  45

Phe Glu Ile Val Glu Gly Asn Arg Gly Pro Gln Ala Ala Asn Val Thr
            50                  55                  60

Lys Glu Ala
65

<210> SEQ ID NO 458
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 458

Met Val Glu Gly Lys Val Lys Trp Phe Asn Ser Glu Lys Gly Arg Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
            50                  55                  60

Lys Glu Ala
65

<210> SEQ ID NO 459
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 459

Met Val Glu Gly Lys Val Lys Trp Phe Asn Ser Glu Lys Gly Thr Gly
1               5                   10                  15

Phe Ile Glu Val Glu Gly Gln Asp Asp Val Phe Val His Phe Ser Ala

```
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 460
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 460

Met Val Glu Gly Lys Val Lys Trp Phe Asn Ser Glu Lys Gly Phe Gly
1               5                   10                  15

Ala Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 461
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 461

Met Val Glu Gly Lys Val Lys Trp Phe Asn Ser Glu Lys Gly Ile Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 462
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 462

Met Val Glu Gly Lys Val Lys Trp Phe Asn Ser Glu Lys Gly Phe Gly
1               5                   10                  15

Gln Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45
```

```
Phe Glu Ile Val Glu Gly Asn Arg Gly Pro Gln Ala Ala Asn Val Thr
    50                  55                  60

Lys Glu Ala
65

<210> SEQ ID NO 463
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 463

Met Val Glu Gly Lys Val Lys Trp Phe Asn Ser Glu Lys Gly Phe Gly
1               5                   10                  15

Val Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 464
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 464

Met Val Glu Gly Lys Val Lys Trp Phe Asn Ser Glu Lys Gly Asn Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 465
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 465

Met Val Glu Gly Lys Val Lys Trp Phe Asn Ser Glu Lys Gly Trp Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60
```

Lys Glu Ala
65

<210> SEQ ID NO 466
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 466

Met Val Glu Gly Lys Val Lys Trp Phe Asn Ser Glu Lys Gly Phe Gly
1               5                   10                  15

Arg Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 467
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 467

Met Val Glu Gly Lys Val Lys Trp Phe Asn Ser Glu Lys Gly Phe Gly
1               5                   10                  15

Ser Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 468
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 468

Met Val Glu Gly Lys Val Lys Trp Phe Asn Ser Glu Lys Gly Leu Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

-continued

```
<210> SEQ ID NO 469
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 469

Met Val Glu Gly Lys Val Lys Trp Phe Asn Ser Glu Lys Gly Ser Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 470
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 470

Met Val Glu Gly Lys Val Lys Trp Phe Asn Ser Glu Lys Gly Phe Gly
1               5                   10                  15

Gly Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 471
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 471

Met Val Glu Gly Lys Val Lys Trp Phe Asn Ser Glu Lys Gly Phe Gly
1               5                   10                  15

Phe Ile Glu Val Glu Gly Gln Asp Asp Val Ala Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 472
<211> LENGTH: 67
<212> TYPE: PRT
<213> ORGANISM: Artificial Sequence
```

-continued

<220> FEATURE:
<223> OTHER INFORMATION: synthetic sequence, Bs-CspB variant

<400> SEQUENCE: 472

Met Val Glu Gly Lys Val Lys Trp Phe Asn Ser Glu Lys Gly Gln Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 473
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 473

Met Val Glu Gly Lys Val Lys Trp Phe Asn Ser Glu Lys Gly Tyr Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 474
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 474

Met Val Glu Gly Lys Val Lys Trp Phe Asn Ser Glu Lys Gly Phe Gly
1               5                   10                  15

Thr Ile Glu Val Glu Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 475
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 475

```
Met Val Glu Gly Lys Val Lys Trp Phe Asn Ser Glu Lys Gly Lys Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
            50                  55                  60

Lys Glu Ala
65
```

<210> SEQ ID NO 476
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 476

```
Met Val Glu Gly Lys Val Lys Trp Phe Asn Ser Glu Lys Gly Phe Gly
1               5                   10                  15

His Ile Glu Val Glu Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
            50                  55                  60

Lys Glu Ala
65
```

<210> SEQ ID NO 477
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 477

```
Met Val Glu Gly Lys Val Lys Trp Phe Asn Ser Glu Lys Gly Phe Gly
1               5                   10                  15

Phe Ile Glu Val Glu Gly Gln Asp Asp Val Arg Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
            50                  55                  60

Lys Glu Ala
65
```

<210> SEQ ID NO 478
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 478

```
Met Val Glu Gly Lys Val Lys Trp Phe Asn Ser Glu Lys Gly Phe Gly
1               5                   10                  15
```

Phe Ile Glu Val Gly Gln Asp Asp Val Pro Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 479
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 479

Met Val Glu Gly Lys Val Lys Trp Phe Asn Ser Glu Lys Gly Gly Gly
1               5                   10                  15

Phe Ile Glu Val Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 480
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 480

Met Val Glu Gly Lys Val Lys Trp Phe Asn Ser Glu Lys Gly Val Gly
1               5                   10                  15

Phe Ile Glu Val Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 481
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 481

Met Val Glu Gly Lys Val Lys Trp Phe Asn Ser Glu Lys Gly Phe Gly
1               5                   10                  15

Tyr Ile Glu Val Gly Gln Asp Asp Val Phe Val His Phe Ser Ala
            20                  25                  30

Ile Gln Gly Glu Gly Phe Lys Thr Leu Glu Glu Gly Gln Ala Val Ser

```
                35                  40                  45
Phe Glu Ile Val Glu Gly Asn Arg Gly Pro Gln Ala Ala Asn Val Thr
    50                  55                  60

Lys Glu Ala
65

<210> SEQ ID NO 482
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 482

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Trp Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 483
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 483

Met Val Glu Gly Lys Val Lys Trp Phe Asn Ser Glu Lys Gly Phe Gly
1               5                   10                  15

Cys Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 484
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 484

Met Val Glu Gly Lys Val Lys Trp Phe Asn Ser Glu Lys Gly Phe Gly
1               5                   10                  15

Ile Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60
```

Lys Glu Ala
65

<210> SEQ ID NO 485
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 485

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Asp Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 486
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 486

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Pro Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 487
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 487

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Tyr Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 488
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 488

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His His Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 489
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 489

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Asn Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 490
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 490

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Met Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 491
<211> LENGTH: 67
<212> TYPE: PRT

<213> ORGANISM: Artificial Sequence
<220> FEATURE:
<223> OTHER INFORMATION: synthetic sequence, Bs-CspB variant

<400> SEQUENCE: 491

```
Met Val Glu Gly Lys Val Lys Trp Phe Asn Ser Glu Lys Gly Phe Gly
1               5                   10                  15
Phe Ile Glu Val Glu Gly Gln Asp Asp Val Met Val His Phe Ser Ala
                20                  25                  30
Ile Gln Gly Glu Gly Phe Lys Thr Leu Glu Glu Gly Gln Ala Val Ser
            35                  40                  45
Phe Glu Ile Val Glu Gly Asn Arg Gly Pro Gln Ala Ala Asn Val Thr
        50                  55                  60
Lys Glu Ala
65
```

<210> SEQ ID NO 492
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 492

```
Met Val Glu Gly Lys Val Lys Trp Phe Asn Ser Glu Lys Gly Phe Gly
1               5                   10                  15
Phe Ile Glu Val Glu Gly Gln Asp Asp Val Phe Val Ser Phe Ser Ala
                20                  25                  30
Ile Gln Gly Glu Gly Phe Lys Thr Leu Glu Glu Gly Gln Ala Val Ser
            35                  40                  45
Phe Glu Ile Val Glu Gly Asn Arg Gly Pro Gln Ala Ala Asn Val Thr
        50                  55                  60
Lys Glu Ala
65
```

<210> SEQ ID NO 493
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 493

```
Met Val Glu Gly Lys Val Lys Trp Phe Asn Ser Glu Lys Gly Phe Gly
1               5                   10                  15
Phe Ile Glu Val Glu Gly Gln Asp Asp Val Phe Val Val Phe Ser Ala
                20                  25                  30
Ile Gln Gly Glu Gly Phe Lys Thr Leu Glu Glu Gly Gln Ala Val Ser
            35                  40                  45
Phe Glu Ile Val Glu Gly Asn Arg Gly Pro Gln Ala Ala Asn Val Thr
        50                  55                  60
Lys Glu Ala
65
```

<210> SEQ ID NO 494
<211> LENGTH: 67
<212> TYPE: PRT
<213> ORGANISM: Artificial Sequence
<220> FEATURE:
<223> OTHER INFORMATION: synthetic sequence, Bs-CspB variant -continued

<400> SEQUENCE: 494

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Ile Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 495
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 495

Met Val Glu Gly Lys Val Lys Trp Phe Asn Ser Glu Lys Gly Phe Gly
1               5                   10                  15

Phe Ile Glu Val Glu Gly Gln Asp Asp Val Trp Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 496
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 496

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Phe Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 497
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 497

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Asp Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 498
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 498

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Ala Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 499
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 499

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Thr Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 500
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 500

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Glu Ser Ala
            20                  25                  30

```
Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 501
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 501

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Leu Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 502
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 502

Met Val Glu Gly Lys Val Lys Trp Phe Asn Ser Glu Lys Gly Phe Gly
1               5                   10                  15

Phe Ile Glu Val Glu Gly Gln Asp Asp Val Tyr Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 503
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 503

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Leu Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
```

```
                50                  55                  60

Lys Glu Ala
 65

<210> SEQ ID NO 504
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 504

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Ala Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
     50                  55                  60

Lys Glu Ala
 65

<210> SEQ ID NO 505
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 505

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Cys Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
     50                  55                  60

Lys Glu Ala
 65

<210> SEQ ID NO 506
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 506

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Ser Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
     50                  55                  60

Lys Glu Ala
 65
```

<210> SEQ ID NO 507
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 507

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Arg Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 508
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 508

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Glu Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 509
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 509

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Trp Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 510
<211> LENGTH: 67

<212> TYPE: PRT
<213> ORGANISM: Artificial Sequence
<220> FEATURE:
<223> OTHER INFORMATION: synthetic sequence, Bs-CspB variant

<400> SEQUENCE: 510

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Gly Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 511
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 511

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Lys Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 512
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 512

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Lys Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 513
<211> LENGTH: 67
<212> TYPE: PRT
<213> ORGANISM: Artificial Sequence
<220> FEATURE:
<223> OTHER INFORMATION: synthetic sequence, Bs-CspB variant -continued

<400> SEQUENCE: 513

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Arg Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 514
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 514

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Gln Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 515
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 515

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Thr Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 516
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 516

Met Val Glu Gly Lys Val Lys Trp Phe Asn Ser Glu Lys Gly Arg Gly

```
                1               5                  10                  15
Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
50                  55                  60

Lys Glu Ala
65

<210> SEQ ID NO 517
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 517

Met Val Glu Gly Lys Val Lys Trp Phe Asn Ser Glu Lys Gly Asn Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
50                  55                  60

Lys Glu Ala
65

<210> SEQ ID NO 518
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 518

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Asp Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
50                  55                  60

Lys Glu Ala
65

<210> SEQ ID NO 519
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 519

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Cys Phe Ser Ala
                20                  25                  30
```

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
 50                  55                  60

Lys Glu Ala
 65

<210> SEQ ID NO 520
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 520

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val Gln Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
 50                  55                  60

Lys Glu Ala
 65

<210> SEQ ID NO 521
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 521

Met Val Glu Gly Lys Val Lys Trp Phe Asn Ser Glu Lys Gly Ile Gly
 1               5                  10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
 50                  55                  60

Lys Glu Ala
 65

<210> SEQ ID NO 522
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 522

Met Val Glu Gly Lys Val Lys Trp Phe Asn Ser Glu Lys Gly Leu Gly
 1               5                  10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 523
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 523

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Leu Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 524
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 524

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Lys Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 525
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 525

Met Val Glu Gly Lys Val Lys Trp Phe Asn Ser Glu Lys Gly Thr Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala

```
<210> SEQ ID NO 526
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 526

Met Val Glu Gly Lys Val Lys Trp Phe Asn Ser Glu Lys Gly Trp Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 527
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 527

Met Val Glu Gly Lys Val Lys Trp Phe Asn Ser Glu Lys Gly Tyr Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 528
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 528

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Thr Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 529
```

```
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 529

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Trp Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 530
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 530

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Tyr Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 531
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 531

Met Val Glu Gly Lys Val Lys Trp Phe Asn Ser Glu Lys Gly Phe Gly
1               5                   10                  15

Arg Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 532
<211> LENGTH: 67
<212> TYPE: PRT
<213> ORGANISM: Artificial Sequence
<220> FEATURE:
```

<223> OTHER INFORMATION: synthetic sequence, Bs-CspB variant

<400> SEQUENCE: 532

Met Val Glu Gly Lys Val Lys Trp Phe Asn Ser Glu Lys Gly Phe Gly
1               5                   10                  15

Asn Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 533
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 533

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Arg Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 534
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 534

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Asn Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 535
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 535

```
Met Val Glu Gly Lys Val Lys Trp Phe Asn Ser Glu Lys Gly Phe Gly
1               5                   10                  15
Phe Ile Glu Val Glu Gly Gln Asp Asp Val Phe Val His Asp Ser Ala
            20                  25                  30
Ile Gln Gly Glu Gly Phe Lys Thr Leu Glu Glu Gly Gln Ala Val Ser
        35                  40                  45
Phe Glu Ile Val Glu Gly Asn Arg Gly Pro Gln Ala Ala Asn Val Thr
    50                  55                  60
Lys Glu Ala
65

<210> SEQ ID NO 536
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 536

Met Val Glu Gly Lys Val Lys Trp Phe Asn Ser Glu Lys Gly Phe Gly
1               5                   10                  15
Phe Ile Glu Val Glu Gly Gln Asp Asp Val Phe Val His His Ser Ala
            20                  25                  30
Ile Gln Gly Glu Gly Phe Lys Thr Leu Glu Glu Gly Gln Ala Val Ser
        35                  40                  45
Phe Glu Ile Val Glu Gly Asn Arg Gly Pro Gln Ala Ala Asn Val Thr
    50                  55                  60
Lys Glu Ala
65

<210> SEQ ID NO 537
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 537

Met Val Glu Gly Lys Val Lys Trp Phe Asn Ser Glu Lys Gly Phe Gly
1               5                   10                  15
Phe Ile Glu Val Glu Gly Gln Asp Asp Val Phe Val His Ile Ser Ala
            20                  25                  30
Ile Gln Gly Glu Gly Phe Lys Thr Leu Glu Glu Gly Gln Ala Val Ser
        35                  40                  45
Phe Glu Ile Val Glu Gly Asn Arg Gly Pro Gln Ala Ala Asn Val Thr
    50                  55                  60
Lys Glu Ala
65

<210> SEQ ID NO 538
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 538

Met Val Glu Gly Lys Val Lys Trp Phe Asn Ser Glu Lys Gly Phe Gly
1               5                   10                  15
Tyr Ile Glu Val Glu Gly Gln Asp Asp Val Phe Val His Phe Ser Ala
```

```
              20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 539
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 539

Met Val Glu Gly Lys Val Lys Trp Phe Asn Ser Glu Lys Gly Phe Gly
1               5                   10                  15

Val Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 540
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 540

Met Val Glu Gly Lys Val Lys Trp Phe Asn Ser Glu Lys Gly Phe Gly
1               5                   10                  15

Phe Ile Glu Val Glu Gly Gln Asp Asp Val Ala Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 541
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 541

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Ser Ser Ala
            20                  25                  30

Ile Gln Gly Glu Gly Phe Lys Thr Leu Glu Glu Gly Gln Ala Val Ser
        35                  40                  45
```

```
Phe Glu Ile Val Glu Gly Asn Arg Gly Pro Gln Ala Ala Asn Val Thr
        50                  55                  60

Lys Glu Ala
 65

<210> SEQ ID NO 542
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 542

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Thr Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
        50                  55                  60

Lys Glu Ala
 65

<210> SEQ ID NO 543
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 543

Met Val Glu Gly Lys Val Lys Trp Phe Asn Ser Glu Lys Gly Phe Gly
 1               5                  10                  15

Phe Ile Glu Val Glu Gly Gln Asp Asp Val Glu Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
        50                  55                  60

Lys Glu Ala
 65

<210> SEQ ID NO 544
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 544

Met Val Glu Gly Lys Val Lys Trp Phe Asn Ser Glu Lys Gly Phe Gly
 1               5                  10                  15

Phe Ile Glu Val Glu Gly Gln Asp Asp Val Met Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
        50                  55                  60
```

Lys Glu Ala
65

<210> SEQ ID NO 545
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 545

Met Val Glu Gly Lys Val Lys Trp Phe Asn Ser Glu Lys Gly Phe Gly
1               5                   10                  15

Phe Ile Glu Val Glu Gly Gln Asp Asp Val Pro Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 546
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 546

Met Val Glu Gly Lys Val Lys Trp Phe Asn Ser Glu Lys Gly Phe Gly
1               5                   10                  15

Phe Ile Glu Val Glu Gly Gln Asp Asp Val Ser Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 547
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 547

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Ala Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

-continued

```
<210> SEQ ID NO 548
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 548

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Arg Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 549
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 549

Met Val Glu Gly Lys Val Lys Trp Phe Asn Ser Glu Lys Gly Gln Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 550
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 550

Met Val Glu Gly Lys Val Lys Trp Phe Asn Ser Glu Lys Gly Gly Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 551
<211> LENGTH: 67
<212> TYPE: PRT
<213> ORGANISM: Artificial Sequence
```

<220> FEATURE:
<223> OTHER INFORMATION: synthetic sequence, Bs-CspB variant

<400> SEQUENCE: 551

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Glu Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 552
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 552

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Gly Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 553
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 553

Met Val Glu Gly Lys Val Lys Trp Phe Asn Ser Glu Lys Gly Lys Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 554
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 554

```
Met Val Glu Gly Lys Val Lys Trp Phe Asn Ser Glu Lys Gly Met Gly
1               5                   10                  15

Phe Ile Glu Val Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 555
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 555

Met Val Glu Gly Lys Val Lys Trp Phe Asn Ser Glu Lys Gly Phe Gly
1               5                   10                  15

Phe Ile Glu Val Gly Gln Asp Asp Val Phe Val Ser Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 556
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 556

Met Val Glu Gly Lys Val Lys Trp Phe Asn Ser Glu Lys Gly Val Gly
1               5                   10                  15

Phe Ile Glu Val Gly Gln Asp Asp Val Phe Val His Phe Ser Ala
                20                  25                  30

Ile Gln Gly Glu Gly Phe Lys Thr Leu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 557
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 557

Met Val Glu Gly Lys Val Lys Trp Phe Asn Ser Glu Lys Gly Phe Gly
1               5                   10                  15
```

```
Ala Ile Glu Val Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 558
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 558

Met Val Glu Gly Lys Val Lys Trp Phe Asn Ser Glu Lys Gly Phe Gly
1               5                   10                  15

Phe Ile Glu Val Gly Gln Asp Asp Val Phe Val Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 559
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 559

Met Val Glu Gly Lys Val Lys Trp Phe Asn Ser Glu Lys Gly Phe Gly
1               5                   10                  15

Phe Ile Glu Val Gly Gln Asp Asp Val Phe Val His Ala Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 560
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 560

Met Val Glu Gly Lys Val Lys Trp Phe Asn Ser Glu Lys Gly Phe Gly
1               5                   10                  15

Gly Ile Glu Val Gly Gln Asp Asp Val Phe Val His Phe Ser Ala
            20                  25                  30

Ile Gln Gly Glu Gly Phe Lys Thr Leu Glu Gly Gln Ala Val Ser
```

```
                    35                  40                  45

Phe Glu Ile Val Glu Gly Asn Arg Gly Pro Gln Ala Ala Asn Val Thr
    50                  55                  60

Lys Glu Ala
65

<210> SEQ ID NO 561
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 561

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Glu Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 562
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 562

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Gly Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 563
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 563

Met Val Glu Gly Lys Val Lys Trp Phe Asn Ser Glu Lys Gly Phe Gly
1               5                   10                  15

Thr Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60
```

Lys Glu Ala
65

<210> SEQ ID NO 564
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 564

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Lys Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 565
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 565

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Met Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 566
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 566

Met Val Glu Gly Lys Val Lys Trp Phe Asn Ser Glu Lys Gly Phe Gly
1               5                   10                  15

Phe Ile Glu Val Glu Gly Gln Asp Asp Val Arg Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

-continued

<210> SEQ ID NO 567
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 567

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Val Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 568
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 568

Met Val Glu Gly Lys Val Lys Trp Phe Asn Ser Glu Lys Gly Phe Gly
1               5                   10                  15

Phe Ile Glu Val Glu Gly Gln Asp Asp Val Leu Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 569
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 569

Met Val Glu Gly Lys Val Lys Trp Phe Asn Ser Glu Lys Gly Phe Gly
1               5                   10                  15

Phe Ile Glu Val Glu Gly Gln Asp Asp Val Trp Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 570
<211> LENGTH: 67
<212> TYPE: PRT

<213> ORGANISM: Artificial Sequence
<220> FEATURE:
<223> OTHER INFORMATION: synthetic sequence, Bs-CspB variant

<400> SEQUENCE: 570

Met Val Glu Gly Lys Val Lys Trp Phe Asn Ser Glu Lys Gly Phe Gly
1               5                   10                  15

Ile Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 571
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 571

Met Val Glu Gly Lys Val Lys Trp Phe Asn Ser Glu Lys Gly Phe Gly
1               5                   10                  15

Phe Ile Glu Val Glu Gly Gln Asp Asp Val Cys Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 572
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 572

Met Val Glu Gly Lys Val Lys Trp Phe Asn Ser Glu Lys Gly Phe Gly
1               5                   10                  15

Phe Ile Glu Val Glu Gly Gln Asp Asp Val Tyr Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 573
<211> LENGTH: 67
<212> TYPE: PRT
<213> ORGANISM: Artificial Sequence
<220> FEATURE:
<223> OTHER INFORMATION: synthetic sequence, Bs-CspB variant -continued

```
<400> SEQUENCE: 573

Met Val Glu Gly Lys Val Lys Trp Phe Asn Ser Glu Lys Gly Phe Gly
1               5                   10                  15

Phe Ile Glu Val Glu Gly Gln Asp Asp Val Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 574
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 574

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val Phe Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 575
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 575

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Cys Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 576
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 576

Met Val Glu Gly Lys Val Lys Trp Phe Asn Ser Glu Lys Gly Phe Gly
1               5                   10                  15
```

Phe Ile Glu Val Glu Gly Gln Asp Asp Val Phe Val His Gln Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 577
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 577

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Trp Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 578
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 578

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Tyr Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 579
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 579

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
        35                  40                  45

Phe Asn Ile Gln Ser Gly Asn Arg Gly Pro Gln Ala Ala Asn Val Thr
    50                  55                  60

Lys Glu Ala
65

<210> SEQ ID NO 580
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 580

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 581
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 581

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Ser Lys Asp His Lys Leu Leu Thr Leu Leu
    50                  55                  60

Lys Lys Arg
65

<210> SEQ ID NO 582
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 582

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Lys Lys Gly Pro Gln Ala Ala Asn Val Thr

```
                50                  55                  60

Lys Glu Ala
65

<210> SEQ ID NO 583
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 583

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Gly Lys Gly Pro Gln Ala Ala Asn Val Thr
    50                  55                  60

Lys Glu Ala
65

<210> SEQ ID NO 584
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 584

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Gly Arg Gly Pro Gln Ala Ala Asn Val Thr
    50                  55                  60

Lys Glu Ala
65

<210> SEQ ID NO 585
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 585

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Arg Arg Gly Pro Gln Ala Ala Asn Val Thr
    50                  55                  60

Lys Glu Ala
65
```

<210> SEQ ID NO 586
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 586

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Pro Arg Gly Pro Gln Ala Ala Asn Val Thr
    50                  55                  60

Lys Glu Ala
65
```

<210> SEQ ID NO 587
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 587

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Pro Lys Gly Pro Gln Ala Ala Asn Val Thr
    50                  55                  60

Lys Glu Ala
65
```

<210> SEQ ID NO 588
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 588

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Pro Arg Gly Pro Gln Ala Ala Asn Val Thr
    50                  55                  60

Lys Glu Ala
65
```

<210> SEQ ID NO 589
<211> LENGTH: 67

```
<212> TYPE: PRT
<213> ORGANISM: Artificial Sequence
<220> FEATURE:
<223> OTHER INFORMATION: synthetic sequence, Bs-CspB variant

<400> SEQUENCE: 589

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Arg Gly Pro Gln Ala Ala Asn Val Thr
    50                  55                  60

Lys Glu Ala
65

<210> SEQ ID NO 590
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 590

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Ser Lys Gly Pro Gln Ala Ala Asn Val Thr
    50                  55                  60

Lys Glu Ala
65

<210> SEQ ID NO 591
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 591

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Pro Lys Gly Pro Gln Ala Ala Asn Val Thr
    50                  55                  60

Lys Glu Ala
65

<210> SEQ ID NO 592
<211> LENGTH: 67
<212> TYPE: PRT
<213> ORGANISM: Artificial Sequence
<220> FEATURE:
<223> OTHER INFORMATION: synthetic sequence, Bs-CspB variant
```

<400> SEQUENCE: 592

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Thr Lys Gly Pro Gln Ala Ala Asn Val Thr
    50                  55                  60

Lys Glu Ala
65

<210> SEQ ID NO 593
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 593

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Lys Gly Pro Gln Ala Ala Asn Val Thr
    50                  55                  60

Lys Glu Ala
65

<210> SEQ ID NO 594
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 594

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Thr Arg Gly Pro Gln Ala Ala Asn Val Thr
    50                  55                  60

Lys Glu Ala
65

<210> SEQ ID NO 595
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 595

Met Val Glu Gly Lys Val Lys Trp Phe Asn Ser Glu Lys Gly Phe Gly

```
                 1               5                  10                 15
Phe Ile Glu Val Glu Gly Gln Asp Asp Val Phe Val His Phe Ser Ala
                20                  25                 30

Ile Gln Gly Glu Gly Phe Lys Thr Leu Glu Glu Gly Gln Ala Val Ser
            35                  40                 45

Phe Glu Ile Val Glu Gly Arg Gly Pro Gln Ala Ala Asn Val Thr
    50                  55                 60

Lys Glu Ala
65
```

<210> SEQ ID NO 596
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 596

```
Met Val Glu Gly Lys Val Lys Trp Phe Asn Ser Glu Lys Gly Phe Gly
1               5                  10                 15

Phe Ile Glu Val Glu Gly Gln Asp Asp Val Phe Val His Phe Ser Ala
                20                  25                 30

Ile Gln Gly Glu Gly Phe Lys Thr Leu Glu Glu Gly Gln Ala Val Ser
            35                  40                 45

Phe Glu Ile Val Glu Gly Lys Arg Gly Pro Gln Ala Ala Asn Val Thr
    50                  55                 60

Lys Glu Ala
65
```

<210> SEQ ID NO 597
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 597

```
Met Val Glu Gly Lys Val Lys Trp Phe Asn Ser Glu Lys Gly Phe Gly
1               5                  10                 15

Phe Ile Glu Val Glu Gly Gln Asp Asp Val Phe Val His Phe Ser Ala
                20                  25                 30

Ile Gln Gly Glu Gly Phe Lys Thr Leu Glu Glu Gly Gln Ala Val Ser
            35                  40                 45

Phe Glu Ile Val Glu Gly Asn Arg Gly Pro Gln Ala Val Asn Val Glu
    50                  55                 60

Ile Glu Ala
65
```

<210> SEQ ID NO 598
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 598

```
Met Val Glu Gly Lys Val Lys Trp Phe Asn Ser Glu Lys Gly Phe Gly
1               5                  10                 15

Phe Ile Glu Val Glu Gly Gln Asp Asp Val Phe Val His Phe Ser Ala
                20                  25                 30
```

```
Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Thr Asn Val Ile
     50                  55                  60

Val Lys Ala
 65

<210> SEQ ID NO 599
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 599

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
             20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ser Gln Val Ile
     50                  55                  60

Glu Leu Ala
 65

<210> SEQ ID NO 600
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 600

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
             20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Val Asn Val Glu
     50                  55                  60

Ile Lys Ala
 65

<210> SEQ ID NO 601
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 601

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
             20                  25                  30

Ile Gln Gly Glu Gly Phe Lys Thr Leu Glu Glu Gly Gln Ala Val Ser
            35                  40                  45
```

```
Phe Glu Ile Val Glu Gly Asn Arg Gly Pro Gln Ala Ser Lys Val Ala
        50                  55                  60

Lys Thr Ala
 65

<210> SEQ ID NO 602
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 602

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Ala
        50                  55                  60

Ala Glu Ala
 65

<210> SEQ ID NO 603
<211> LENGTH: 66
<212> TYPE: PRT
<213> ORGANISM: Artificial Sequence
<220> FEATURE:
<223> OTHER INFORMATION: synthetic sequence, Bs-CspB variant

<400> SEQUENCE: 603

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Asn Val Thr Lys
        50                  55                  60

Glu Ala
 65

<210> SEQ ID NO 604
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 604

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Lys Val Ile
        50                  55                  60

Lys Leu Ala
```

<210> SEQ ID NO 605
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 605

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Asn Val Ile
    50                  55                  60

Lys Val Ala
65

<210> SEQ ID NO 606
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 606

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Thr Lys Val Lys
    50                  55                  60

Lys Glu Ala
65

<210> SEQ ID NO 607
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 607

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ser Lys Val Lys
    50                  55                  60

Ile Lys Ala
65

<210> SEQ ID NO 608

<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 608

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile His Val Glu
    50                  55                  60

Thr Gln Ala
65

<210> SEQ ID NO 609
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 609

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Lys Val Glu
    50                  55                  60

Ala Ile Ala
65

<210> SEQ ID NO 610
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 610

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Asn Val Ile
    50                  55                  60

Ile Glu Ala
65

<210> SEQ ID NO 611
<211> LENGTH: 67
<212> TYPE: PRT
<213> ORGANISM: Artificial Sequence
<220> FEATURE:

<223> OTHER INFORMATION: synthetic sequence, Bs-CspB variant

<400> SEQUENCE: 611

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Gly Gln Val Ile
    50                  55                  60

Lys Leu Ala
65

<210> SEQ ID NO 612
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 612

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile His Val Lys
    50                  55                  60

Ala Pro Ala
65

<210> SEQ ID NO 613
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 613

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Val
    50                  55                  60

Thr Lys Ala
65

<210> SEQ ID NO 614
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 614

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Gly Lys Leu Gln
    50                  55                  60

Lys Lys Arg
65

<210> SEQ ID NO 615
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 615

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Asn Val Glu
    50                  55                  60

Lys Lys Ala
65

<210> SEQ ID NO 616
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 616

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Gln Val Ala
    50                  55                  60

Glu Val Ala
65

<210> SEQ ID NO 617
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 617

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
```

```
                    20                  25                  30

Ile Gln Gly Glu Gly Phe Lys Thr Leu Glu Glu Gly Gln Ala Val Ser
                35                  40                  45

Phe Glu Ile Val Glu Gly Asn Arg Gly Pro Gln Ala Ala Lys Val Thr
            50                  55                  60

Ile Thr Ala
65

<210> SEQ ID NO 618
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 618

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
                35                  40                  45

Phe Glu Ile Val Glu Gly Asn Arg Gly Pro Gln Ala Thr Lys Val Ile
            50                  55                  60

Val Ile Ala
65

<210> SEQ ID NO 619
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 619

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
                35                  40                  45

Phe Glu Ile Val Glu Gly Asn Arg Gly Pro Gln Ala Thr Gln Val Glu
            50                  55                  60

Ile Pro Ala
65

<210> SEQ ID NO 620
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 620

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
                35                  40                  45
```

```
Phe Glu Ile Val Glu Gly Asn Arg Gly Pro Gln Ala Ile Lys Leu Lys
    50                  55                  60

Lys Gln Arg
 65

<210> SEQ ID NO 621
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 621

Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Gly Gln Val Ile
    50                  55                  60

Glu Thr Ala
 65

<210> SEQ ID NO 622
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 622

Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ser Gln Val Ala
    50                  55                  60

Ala Pro Ala
 65

<210> SEQ ID NO 623
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 623

Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Lys Leu Gln
    50                  55                  60
```

Lys Lys Arg
65

<210> SEQ ID NO 624
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 624

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Gln Val Ile
    50                  55                  60

Lys Gln Ala
65

<210> SEQ ID NO 625
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 625

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Lys Val Glu
    50                  55                  60

Lys Gln Ala
65

<210> SEQ ID NO 626
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 626

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Thr Gln Val Glu
    50                  55                  60

Val Ile Ala
65

```
<210> SEQ ID NO 627
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 627

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ser His Val Glu
    50                  55                  60

Glu Lys Ala
65

<210> SEQ ID NO 628
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 628

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Lys Val Lys
    50                  55                  60

Lys Lys Ala
65

<210> SEQ ID NO 629
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 629

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Gly Gln Val Ile
    50                  55                  60

Glu Ala Ala
65

<210> SEQ ID NO 630
<211> LENGTH: 65
<212> TYPE: PRT
<213> ORGANISM: Artificial Sequence
```

<220> FEATURE:
<223> OTHER INFORMATION: synthetic sequence, Bs-CspB variant

<400> SEQUENCE: 630

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Val Gln Val Glu
    50                  55                  60

Arg
65

<210> SEQ ID NO 631
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 631

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ser Asn Val Lys
    50                  55                  60

Glu Ala Ala
65

<210> SEQ ID NO 632
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 632

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Thr Asn Val Ala
    50                  55                  60

Thr Glu Ala
65

<210> SEQ ID NO 633
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 633

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Ala Lys Val Ile
    50                  55                  60

Lys Thr Ala
65

<210> SEQ ID NO 634
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 634

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Gly Asn Val Ile
    50                  55                  60

Thr Ile Ala
65

<210> SEQ ID NO 635
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 635

Met Val Glu Gly Lys Val Lys Trp Phe Asn Ser Glu Lys Gly Phe Gly
1               5                   10                  15

Phe Ile Glu Val Gly Gln Asp Asp Val Phe Val His Phe Ser Ala
            20                  25                  30

Ile Gln Gly Glu Gly Phe Lys Thr Leu Glu Gly Gln Ala Val Ser
        35                  40                  45

Phe Glu Ile Val Glu Gly Asn Arg Gly Pro Gln Ala Thr Gln Val Ala
    50                  55                  60

Ile Gln Ala
65

<210> SEQ ID NO 636
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 636

Met Val Glu Gly Lys Val Lys Trp Phe Asn Ser Glu Lys Gly Phe Gly
1               5                   10                  15

-continued

Phe Ile Glu Val Glu Gly Gln Asp Asp Val Phe Val His Phe Ser Ala
            20                  25                  30

Ile Gln Gly Glu Gly Phe Lys Thr Leu Thr Glu Cys Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 637
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 637

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Thr Glu Asn Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 638
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 638

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Thr Glu Asn Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 639
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 639

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Glu Glu Asp Gln Ala Val Ser

-continued

```
              35                  40                  45
Phe Glu Ile Val Glu Gly Asn Arg Gly Pro Gln Ala Ala Asn Val Thr
    50                  55                  60

Lys Glu Ala
65

<210> SEQ ID NO 640
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 640

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Ser Leu Thr Glu Asn Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 641
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 641

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Ser Leu Ala Glu Asn Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 642
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 642

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Gly Glu Asp Gln Ala Val Ser
            35                  40                  45

Phe Glu Ile Val Glu Gly Asn Arg Gly Pro Gln Ala Ala Asn Val Thr
    50                  55                  60
```

<210> SEQ ID NO 643
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 643

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Thr Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 644
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 644

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Ser Leu Asn Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65
```

<210> SEQ ID NO 645
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 645

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Gly Arg Gly Pro Gln Ala Ala Asn Val Thr
    50                  55                  60

Lys Glu Ala
65
```

-continued

<210> SEQ ID NO 646
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 646

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Ser Leu Glu Ser Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 647
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 647

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Ser Leu Ser Glu Ser Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 648
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 648

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Ser Leu Thr Glu Asp Gln Ala Val Ser
            35                  40                  45

Phe Glu Ile Val Glu Gly Asn Arg Gly Pro Gln Ala Ala Asn Val Thr
    50                  55                  60

Lys Glu Ala
65

<210> SEQ ID NO 649
<211> LENGTH: 67
<212> TYPE: PRT

```
<213> ORGANISM: Artificial Sequence
<220> FEATURE:
<223> OTHER INFORMATION: synthetic sequence, Bs-CspB variant

<400> SEQUENCE: 649

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Ser Leu Ala Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 650
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 650

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Lys Arg Gly Pro Gln Ala Ala Asn Val Thr
        50                  55                  60

Lys Glu Ala
65

<210> SEQ ID NO 651
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 651

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Thr Leu Gln Ser Gly Asn Arg Gly Pro Gln Ala Ala Asn Val Thr
        50                  55                  60

Lys Glu Ala
65

<210> SEQ ID NO 652
<211> LENGTH: 67
<212> TYPE: PRT
<213> ORGANISM: Artificial Sequence
<220> FEATURE:
<223> OTHER INFORMATION: synthetic sequence, Bs-CspB variant
```

-continued

```
<400> SEQUENCE: 652

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Leu Val Pro Gly Asn Arg Gly Pro Gln Ala Ala Asn Val Thr
        50                  55                  60

Lys Glu Ala
65

<210> SEQ ID NO 653
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 653

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Asn Leu Leu Gln Gly Asn Arg Gly Pro Gln Ala Ala Asn Val Thr
        50                  55                  60

Lys Glu Ala
65

<210> SEQ ID NO 654
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 654

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Ala Ile Gln Ser Gly Asn Arg Gly Pro Gln Ala Ala Asn Val Thr
        50                  55                  60

Lys Glu Ala
65

<210> SEQ ID NO 655
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 655

Met Val Glu Gly Lys Val Lys Trp Phe Asn Ser Glu Lys Gly Phe Gly
1               5                   10                  15
```

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Thr Val Gln Ser Gly Asn Arg Gly Pro Gln Ala Ala Asn Val Thr
    50                  55                  60

Lys Glu Ala
65

<210> SEQ ID NO 656
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 656

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Asp Leu Val Ala Gly Asn Arg Gly Pro Gln Ala Ala Asn Val Thr
    50                  55                  60

Lys Glu Ala
65

<210> SEQ ID NO 657
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 657

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Thr Leu Leu Ser Gly Asn Arg Gly Pro Gln Ala Ala Asn Val Thr
    50                  55                  60

Lys Glu Ala
65

<210> SEQ ID NO 658
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 658

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Asp Leu Glu Pro Gly Asn Arg Gly Pro Gln Ala Ala Asn Val Thr
    50                  55                  60

Lys Glu Ala
65

<210> SEQ ID NO 659
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 659

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Asp Leu Gln Gln Gly Asn Arg Gly Pro Gln Ala Ala Asn Val Thr
    50                  55                  60

Lys Glu Ala
65

<210> SEQ ID NO 660
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 660

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Asn Leu Leu Pro Gly Asn Arg Gly Pro Gln Ala Ala Asn Val Thr
    50                  55                  60

Lys Glu Ala
65

<210> SEQ ID NO 661
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 661

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Asn Val Leu Ala Gly Asn Arg Gly Pro Gln Ala Ala Asn Val Thr

```
                50                  55                  60

Lys Glu Ala
 65

<210> SEQ ID NO 662
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 662

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Asp Ile Leu Pro Gly Asn Arg Gly Pro Gln Ala Ala Asn Val Thr
        50                  55                  60

Lys Glu Ala
 65

<210> SEQ ID NO 663
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 663

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Asp Leu Val Gln Gly Asn Arg Gly Pro Gln Ala Ala Asn Val Thr
        50                  55                  60

Lys Glu Ala
 65

<210> SEQ ID NO 664
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 664

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Lys Leu Val Ala Gly Asn Arg Gly Pro Gln Ala Ala Asn Val Thr
        50                  55                  60

Lys Glu Ala
 65
```

<210> SEQ ID NO 665
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 665

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Ala Leu Gln Ala Gly Asn Arg Gly Pro Gln Ala Ala Asn Val Thr
    50                  55                  60

Lys Glu Ala
65

<210> SEQ ID NO 666
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 666

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Ala Leu Leu Pro Gly Asn Arg Gly Pro Gln Ala Ala Asn Val Thr
    50                  55                  60

Lys Glu Ala
65

<210> SEQ ID NO 667
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 667

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Lys Leu Val Gln Gly Asn Arg Gly Pro Gln Ala Ala Asn Val Thr
    50                  55                  60

Lys Glu Ala
65

<210> SEQ ID NO 668
<211> LENGTH: 67

```
<212> TYPE: PRT
<213> ORGANISM: Artificial Sequence
<220> FEATURE:
<223> OTHER INFORMATION: synthetic sequence, Bs-CspB variant

<400> SEQUENCE: 668

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Thr Leu Val Gln Gly Asn Arg Gly Pro Gln Ala Ala Asn Val Thr
    50                  55                  60

Lys Glu Ala
65

<210> SEQ ID NO 669
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 669

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Ala Leu Gln Glu Gly Asn Arg Gly Pro Gln Ala Ala Asn Val Thr
    50                  55                  60

Lys Glu Ala
65

<210> SEQ ID NO 670
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 670

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Leu Val Pro Gly Asn Arg Gly Pro Gln Ala Ala Asn Val Thr
    50                  55                  60

Lys Glu Ala
65

<210> SEQ ID NO 671
<211> LENGTH: 67
<212> TYPE: PRT
<213> ORGANISM: Artificial Sequence
<220> FEATURE:
<223> OTHER INFORMATION: synthetic sequence, Bs-CspB variant
```

<400> SEQUENCE: 671

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Ala Leu Gln Ala Gly Asn Arg Gly Pro Gln Ala Ala Asn Val Thr
    50                  55                  60

Lys Glu Ala
65

<210> SEQ ID NO 672
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 672

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Thr Leu Gln Pro Gly Asn Arg Gly Pro Gln Ala Ala Asn Val Thr
    50                  55                  60

Lys Glu Ala
65

<210> SEQ ID NO 673
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 673

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Asp Ile Leu Pro Gly Asn Arg Gly Pro Gln Ala Ala Asn Val Thr
    50                  55                  60

Lys Glu Ala
65

<210> SEQ ID NO 674
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 674

Met Val Glu Gly Lys Val Lys Trp Phe Asn Ser Glu Lys Gly Phe Gly

```
                1               5                  10                  15
Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Leu Gln Gln Gly Asn Arg Gly Pro Gln Ala Ala Asn Val Thr
    50                  55                  60

Lys Glu Ala
65

<210> SEQ ID NO 675
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 675

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Asp Leu Gln Gln Gly Asn Arg Gly Pro Gln Ala Ala Asn Val Thr
    50                  55                  60

Lys Glu Ala
65

<210> SEQ ID NO 676
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 676

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Asp Leu Val Ala Gly Asn Arg Gly Pro Gln Ala Ala Asn Val Thr
    50                  55                  60

Lys Glu Ala
65

<210> SEQ ID NO 677
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 677

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30
```

Ile Gln Gly Glu Gly Phe Lys Thr Leu Glu Glu Gly Gln Ala Val Ser
        35                  40                  45

Phe Thr Leu Gln Ser Gly Asn Arg Gly Pro Gln Ala Ala Asn Val Thr
    50                  55                  60

Lys Glu Ala
65

<210> SEQ ID NO 678
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 678

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Thr Val Gln Pro Gly Asn Arg Gly Pro Gln Ala Ala Asn Val Thr
    50                  55                  60

Lys Glu Ala
65

<210> SEQ ID NO 679
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 679

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Asn Leu Leu Gln Gly Asn Arg Gly Pro Gln Ala Ala Asn Val Thr
    50                  55                  60

Lys Glu Ala
65

<210> SEQ ID NO 680
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 680

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Asn Leu Leu Pro Gly Asn Arg Gly Pro Gln Ala Ala Asn Val Thr
          50                  55                  60

Lys Glu Ala
 65

<210> SEQ ID NO 681
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 681

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Asn Val Leu Ala Gly Asn Arg Gly Pro Gln Ala Ala Asn Val Thr
    50                  55                  60

Lys Glu Ala
 65

<210> SEQ ID NO 682
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 682

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Ala Val Leu Gln Gly Asn Arg Gly Pro Gln Ala Ala Asn Val Thr
    50                  55                  60

Lys Glu Ala
 65

<210> SEQ ID NO 683
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 683

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Lys Leu Val Ala Gly Asn Arg Gly Pro Gln Ala Ala Asn Val Thr
    50                  55                  60

Lys Glu Ala

<210> SEQ ID NO 684
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 684

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Asp Leu Glu Pro Gly Asn Arg Gly Pro Gln Ala Ala Asn Val Thr
        50                  55                  60

Lys Glu Ala
65

<210> SEQ ID NO 685
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 685

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Asn Val Gln Ala Gly Asn Arg Gly Pro Gln Ala Ala Asn Val Thr
        50                  55                  60

Lys Glu Ala
65

<210> SEQ ID NO 686
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 686

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Leu Leu Ser Gly Asn Arg Gly Pro Gln Ala Ala Asn Val Thr
        50                  55                  60

Lys Glu Ala
65

<210> SEQ ID NO 687

```
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 687

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Asp Ile Leu Ser Gly Asn Arg Gly Pro Gln Ala Ala Asn Val Thr
        50                  55                  60

Lys Glu Ala
65

<210> SEQ ID NO 688
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 688

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Thr Val Gln Ala Gly Asn Arg Gly Pro Gln Ala Ala Asn Val Thr
        50                  55                  60

Lys Glu Ala
65

<210> SEQ ID NO 689
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 689

Met Val Glu Gly Lys Val Lys Trp Phe Asn Ser Glu Lys Gly Phe Gly
 1               5                  10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Asn Leu Gln Ser Gly Asn Arg Gly Pro Gln Ala Ala Asn Val Thr
        50                  55                  60

Lys Glu Ala
65

<210> SEQ ID NO 690
<211> LENGTH: 67
<212> TYPE: PRT
<213> ORGANISM: Artificial Sequence
<220> FEATURE:
```

<223> OTHER INFORMATION: synthetic sequence, Bs-CspB variant

<400> SEQUENCE: 690

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Lys Val Ala
    50                  55                  60

Thr Gln Ala
65

<210> SEQ ID NO 691
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 691

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Thr Lys Val Glu
    50                  55                  60

Glu Val Ala
65

<210> SEQ ID NO 692
<211> LENGTH: 68
<212> TYPE: PRT
<213> ORGANISM: Artificial Sequence
<220> FEATURE:
<223> OTHER INFORMATION: synthetic sequence, Bs-CspB variant

<400> SEQUENCE: 692

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Gln Val Cys
    50                  55                  60

Asn Thr Ser Val
65

<210> SEQ ID NO 693
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 693

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Lys Val Thr
    50                  55                  60

Glu Leu Ala
65

<210> SEQ ID NO 694
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 694

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Gly Lys Val Glu
    50                  55                  60

Glu Lys Ala
65

<210> SEQ ID NO 695
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 695

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Gln Val Lys
    50                  55                  60

Thr Glu Ala
65

<210> SEQ ID NO 696
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 696

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala

```
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Val Asn Val Ile
        50                  55                  60

Lys Val Ala
65

<210> SEQ ID NO 697
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 697

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Thr Gln Val Ala
    50                  55                  60

Ile Gln Ala
65

<210> SEQ ID NO 698
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 698

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Lys Val Ala
    50                  55                  60

Ala Thr Ala
65

<210> SEQ ID NO 699
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 699

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45
```

```
Phe Glu Ile Val Glu Gly Asn Arg Gly Pro Gln Ala Thr Gln Val Glu
    50                  55                  60

Ile Pro Ala
65

<210> SEQ ID NO 700
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 700

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ile Lys Leu Lys
    50                  55                  60

Lys Gln Arg
65

<210> SEQ ID NO 701
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 701

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Asn Val Glu
    50                  55                  60

Thr Lys Ala
65

<210> SEQ ID NO 702
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 702

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Lys Leu Gln
    50                  55                  60
```

Lys Lys Arg
65

<210> SEQ ID NO 703
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 703

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala His Val Glu
    50                  55                  60

Ile Lys Ala
65

<210> SEQ ID NO 704
<211> LENGTH: 67
<212> TYPE: PRT
<213> ORGANISM: Artificial Sequence
<220> FEATURE:
<223> OTHER INFORMATION: synthetic sequence, Bs-CspB variant

<400> SEQUENCE: 704

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Val Lys Val Glu
    50                  55                  60

Ala Ile Ala
65

<210> SEQ ID NO 705
<211> LENGTH: 2196
<212> TYPE: DNA
<213> ORGANISM: Oryza sativa
<220> FEATURE:
<223> OTHER INFORMATION: Rice GOS2 gene promoter

<400> SEQUENCE: 705
aatccgaaaa gttctgcac cgttttcacg tcctaactaa caatataggg aacgtgtgct       60
aaatataaaa tgagacctta tatgtagc gctgataact agaactatgt aagaaaaact      120
catccaccta ctttagtggc aatcgggcta aataaaaaag agtcgctaca ctagtttcgt     180
tttccttagt aattaagtgg gaaaatgaaa tcattattgc ttagaatata cgttcacatc     240
tctgtcatga agttaaatta ttcgaggtag ccataattgt catcaaactc ttcttgaata     300
aaaaaatctt tctagctgaa ctcaatgggt aaagagagat atttttttt aaaaaaaaat     360 agaatgaaga tattctgaac gtatcggcaa agatttaaac atataattat ataatttat     420 agtttgtgca ttcgttatat cgcacgtcat taaggacatg tcttactcca tctcaatttt     480

```
tatttagtaa ttaaagacaa ttgacttatt tttattattt atctttttc gattagatgc      540 aaggtactta cgcacacact ttgtgctcat gtgcatgtgt gagtgcacct cctcaataca      600
cgttcaacta gcgacacatc tccaatatca ctcgcctatt aatacatttt aggtagcaat      660
atctgaattc aagcactcca ccatcaccag accactttta ataatatcta aaatacaaaa      720
aataatttta cagaatagca tgaaaagtat gaaacgaact atttaggttt ttcacataca      780
aaaaaaaaaa gaattttgct cgtgcgcgag cgccaatctc ccatattggg cacacaggca      840
acaacagagt ggctgcccac agaacaaccc acaaaaacg atgatctaac ggaggacagc        900
aagtccgcaa caaccttta acagcaggct ttgcggccag gagagaggag gagaggcaaa       960
gaaaaccaag catcctcctc ctcccgtcta taaattcctc cccctttc ccctctctat       1020 ataggaggca tccaagccaa gaagagggag agcaccaagg acacgcgact agcagaagcc     1080
gagcgaccgc ctcctcgatc catatcttcc ggtcgagttc ttggtcgatc tcttccctcc     1140
tccacctcct cctcacaggg tatgtgcctc ccttcggttg ttcttgaatt tattgttcta     1200
ggttgtgtag tacgggcctt gatgttagga aagggatct gtatctgtga tgattcctgt      1260
tcttggattt gggatagagg ggttcttgat gttgcatgtt atcggttcgg tttgattagt     1320
agtatggttt tcaatcgtct ggagagctct atggaaatga aatggtttag ggatcggaat     1380
cttgcgattt tgtgagtacc ttttgtttga ggtaaaatca gagcaccggt gattttgctt     1440
ggtgtaataa agtacatttg tttggtcctc gattctggta gtgatgcttc tcgatttgac     1500
gaagctatcc tttgtttatt ccctattgaa caaaataat ccaactttga agacggtccc      1560
gttgatgaga ttgaatgatt gattcttaag cctgtccaaa atttcgcagc tggcttgttt    1620
agatacagta gtccccatca cgaaattcat gaaaacagtt ataatcctca ggaacagggg     1680
attccctgtt cttccgattt gctttagtcc cagaattttt tttcccaaat atcttaaaaa     1740
gtcactttct ggttcagttc aatgaattga ttgctacaaa taatgctttt atagcgttat     1800
cctagctgta gttcagttta taggtaatac ccctatagtt tagtcaggag aagaacttat     1860 ccgattctg atctccattt ttaattatat gaaatgaact gtagcataag cagtattcat      1920
ttggattatt ttttttatta gctttcaccc cttcattatt ctgagctgaa agtctggcat     1980
gaactgtcct caattttgtt ttcaaattca catcgattat ctatcgatta tcctcttgta    2040
tctacctgta gaagtttctt tttggttatt ccttgactgc ttgattacag aaagaaattt     2100
atgaagctgt aatcgggata gttatactgc ttgttcttat gattcatttc ctttgtgcag     2160
ttcttggtgt agcttgccac tttcaccagc aaagtt                               2196
```

<210> SEQ ID NO 706
<211> LENGTH: 1748
<212> TYPE: DNA
<213> ORGANISM: Artificial Sequence
<220> FEATURE:
<223> OTHER INFORMATION: synthetic sequence, 35S enhanced rice actin
      promoter

<400> SEQUENCE: 706

```
ctcgaggtca ttcatatgct tgagaagaga gtcgggatag tccaaaataa acaaaggta       60 agattacctg gtcaaaagtg aaaacatcag ttaaaggtg gtataagta aaatatcggt       120 aataaaaggt ggcccaaagt gaaatttact cttttctact attataaaaa ttgaggatgt     180
ttttgtcggt actttgatac gtcattttg tatgaattgg tttttaagtt tattcgcttt      240
```

-continued

```
tggaaatgca tatctgtatt tgagtcgggt tttaagttcg tttgcttttg taaatacaga    300
gggatttgta taagaaatat ctttagaaaa acccatatgc taatttgaca taattttttga   360 gaaaaatata tattcaggcg aattctcaca atgaacaata ataagattaa aatagctttc    420
ccccgttgca gcgcatgggt attttttcta gtaaaaataa aagataaact tagactcaaa    480
acatttacaa aaacaacccc taaagttcct aaagcccaaa gtgctatcca cgatccatag    540
caagcccagc ccaacccaac ccaacccaac ccaccccagt ccagccaact ggacaatagt    600
ctccacaccc ccccactatc accgtgagtt gtccgcacgc accgcacgtc tcgcagccaa    660 aaaaaaaag aaagaaaaaa aagaaaaaga aaaacagca ggtgggtccg ggtcgtgggg      720
gccggaaacg cgaggaggat cgcgagccag cgacgaggag cttaggcctc atcgttgaag    780
atgcctctgc cgacagtggt cccaaagatg accccccacc cacgaggagc atcgtggaaa    840
aagaagacgt tccaaccacg tcttcaaagc aagtggattg atgtgatatc tccactgacg    900
taagggatga cgcacaatcc cactatcctt cgaggcctca tcgttgaaga tgcctctgcc    960
gacagtggtc ccaaagatgg accccccaccc acgaggagca tcgtggaaaa agaagacgtt   1020
ccaaccacgt cttcaaagca agtggattga tgtgatatct ccactgacgt aagggatgac    1080
gcacaatccc actatccttc gaagctccct ccctccgctt ccaaagaaac gcccccatc     1140 gccactatat acatacccccc ccctctcctc ccatccccccc aacccttcta gaaccatctt  1200
ccacacactc aagccacact attggagaac acacagggac aacacaccat aagatccaag    1260
ggaggcctcc gccgccgccg gtaaccaccc cgcccctctc ctctttcttt ctccgttttt    1320
ttttccgtct cggtctcgat ctttggcctt ggtagtttgg gtgggcgaga ggcggcttcg    1380
tgcgcgccca gatcggtgcg cgggaggggc gggatctcgc ggctggggct ctcgccggcg    1440
tggatccggc ccggatctcg cggggaatgg ggctctcgga tgtagatctg cgatccgccg    1500
ttgttggggg agatgatggg gggtttaaaa tttccgccgt gctaaacaag atcaggaaga    1560
ggggaaaagg gcactatggt ttatattttt atatatttct gctgcttcgt caggcttaga    1620
tgtgctagat cttctttct tcttttttgtg gtagaattt gaatccctca gcattgttca     1680
tcggtagttt ttcttttcat gatttgtgac aaatgcagcc tcgtgcggag cttttttgta    1740
ggtagaag                                                             1748
```

<210> SEQ ID NO 707
<211> LENGTH: 4
<212> TYPE: PRT
<213> ORGANISM: Artificial
<220> FEATURE:
<223> OTHER INFORMATION: Synthetic

<400> SEQUENCE: 707

Ala Leu Glu Ala

<210> SEQ ID NO 708
<211> LENGTH: 4
<212> TYPE: PRT
<213> ORGANISM: Artificial
<220> FEATURE:
<223> OTHER INFORMATION: Synthetic

<400> SEQUENCE: 708

Asp Val Leu Pro

STRESS TOLERANT TRANSGENIC CROP PLANTS

CROSS-REFERENCE TO RELATED APPLICATIONS

The present application is a National Stage application of International Patent Application No. PCT/US2009/053807, filed Aug. 14, 2009 and incorporated herein by reference in its entirety, which claims benefit of priority to U.S. Provisional Application Ser. No. 61/089,058 filed Aug. 15, 2008, which is herein incorporated by reference in its entirety.

INCORPORATION OF SEQUENCE LISTING

The sequence listing that is contained in the file named "SeqListing 55486_US_V2.txt", which is 501,194 bytes (measured in operating system MS-Windows), created on Aug. 20, 2013, is filed herewith by electronic submission and incorporated herein by reference in its entirety.

FIELD OF THE INVENTION

Disclosed herein are transgenic plant cells in seeds and plants with improved stress tolerance and methods of making and using such cells, seeds and plants.

BACKGROUND OF THE INVENTION

Transgenic plants comprising recombinant DNA for expression of a cold shock protein have been demonstrated to have improved abiotic stress tolerance (International Patent Application WO05033318).

SUMMARY OF THE INVENTION

This invention provides novel proteins derived from bacterial cold shock proteins, which upon expression in transgenic plants provide the plants with enhanced stress tolerance. This invention also provides recombinant DNA constructs for expression of such polypeptides. In various aspects of the invention, a recombinant DNA construct comprises a promoter that functions in plants operably linked to nucleotides encoding a protein having a sequence of any one of SEQ ID NO:15 through SEQ ID NO:33 or SEQ ID NO:53 through SEQ ID NO:704, wherein said recombinant DNA construct is stably integrated into a chromosome in a transgenic plant cell. In various aspects of the invention, the polypeptides provide plants with improved yield as compared to control crop plants when the plants are grown under abiotic stress conditions, including high salt, heat, drought or water deficit and cold temperatures.

Also provided in the invention are transgenic plant cells having the recombinant DNA of this invention stably integrated into the plant genome and abiotic stress tolerant plants comprising such plant cells. Abiotic stress tolerant plants express the variant bacterial cold shock proteins of this invention, and include crop plants that are improved in at least one trait selected from heat tolerance, salt tolerance, drought tolerance, and survival after cold shock. The modified bacterial cold shock proteins also provide crop plants having comparable or improved yield as compared to control crop plants when grown in non-stress conditions, including conditions of moderate temperatures and sufficient water. Crop plants of particular interest in the present invention include corn, soybean, cotton, canola, alfalfa, wheat, rice, switchgrass, sugarcane, and sugar beet. This invention also provides transgenic plant cells, propagules, including seeds, and crops having the novel recombinant DNA of this invention.

In another aspect of the invention a plant chromosome having stably integrated DNA for expression of a variant bacterial cold shock protein is provided. Transgenic pollen grains comprising a haploid derivative of a plant cell containing a plant chromosomal DNA segment of this invention are also provided. Another aspect of this invention is anti-counterfeit milled seed having, as an indication of origin, a plant cell with said chromosomal DNA segment of this invention.

The present invention is also directed to methods of plant and seed production. One method provides for the production of transgenic plants having enhanced abiotic stress tolerance by introducing (by transformation or introgressing) recombinant DNA for expression of a variant bacterial cold shock protein into plant cells to provide transgenic plant cells, regenerating a transgenic plant from one or more of said transgenic plant cells, and screening a population of transgenic plants to select a transgenic plant expressing a variant bacterial cold shock protein and having enhanced abiotic stress tolerance.

Another method of this invention provides for the manufacture of non-natural, transgenic seed or propagules that can be used to produce a crop of transgenic plants with enhanced abiotic stress tolerance resulting from expression of a variant bacterial cold shock protein from a plant chromosomal DNA segment of this invention. Such a method comprises screening a population of plants having such plant chromosomal DNA segment for said enhanced abiotic stress tolerance, selecting from said population one or more plants that exhibit enhanced yield as compared to the yield for control plants under abiotic stress conditions, verifying that said plant chromosomal DNA segment is stably integrated in said selected plants, and collecting seed or a regenerative propagule from a selected plant.

Another method provides for the production of inbred corn seed comprising acquiring hybrid corn seed from a herbicide tolerant corn plant which also has a stably-integrated, chromosomal DNA segment of this invention comprising recombinant DNA for expression of a variant bacterial cold shock protein, introgressing the chromosomal DNA segment from said acquired hybrid corn seed into a second corn line by allowing pollen grains comprising a haploid derivative with said chromosomal DNA segment to pollinate said second corn line to produce crossed seeds, producing a population of plants from crossed seeds (where a fraction of the seeds produced from said pollination is homozygous for the chromosomal DNA segment, a fraction is hemizygous, and a fraction does not have the chromosomal DNA segment), selecting corn plants which are homozygous and hemizygous for said chromosomal DNA segment by treating with an herbicide, collecting seed from herbicide-treated-surviving corn plants and planting said seed to produce further progeny corn plants, and backcrossing plants grown from said progeny seeds with said second corn line to produce an inbred corn line. The method can be further employed by crossing the inbred corn line with a third corn line to produce hybrid seed.

Yet another aspect of this invention provides a method of growing a corn, cotton, soybean, sugarcane, switchgrass, rice, wheat, alfalfa, or canola crop without irrigation water comprising planting seed having plant cells with a plant chromosomal DNA segment of this invention, where the seeds are produced from plants that are selected for enhanced water deficit stress tolerance.

Recombinant DNAs comprising a promoter that functions in plants operably linked to a polynucleotide encoding a protein, wherein the protein is a chimeric bacterial cold shock protein wherein at least one Reg 1, Reg 2, Reg 3, Reg 4, or Reg 5 amino acid region of a first bacterial cold shock protein is substituted with at least one corresponding Reg 1, Reg 2, Reg 3, Reg 4, or Reg 5 amino acid region of at least one second bacterial cold shock protein are provided. In certain embodiments, the first bacterial cold shock protein is selected from the group consisting of CspB, CspC, CspD, CspG, Csp1, and Csp2. In still other embodiments, the first bacterial cold shock protein is a CspB protein that comprises a CspB L2V protein. A CspB L2V protein can comprise the protein of SEQ ID NO:1. In any of the aforementioned recombinant DNAs encoding chimeric bacterial cold shock proteins, the second bacterial cold shock protein can be selected from the group consisting of a *Thermotoga maritima* cold shock protein, a *Thermoanaerobacter tengcongensis* cold shock protein, an *Escherichia coli* cold shock protein, and an *Agrobacterium tumefaciens* cold shock protein. In any of the aforementioned recombinant DNAs encoding chimeric bacterial cold shock proteins, the second bacterial cold shock protein can also be selected from the group consisting of a *Thermotoga maritima* Csp1 cold shock protein, a *Thermoanaerobacter tengcongensis* Csp1 cold shock protein, an *Escherichia coli* CspC cold shock protein, an *Escherichia coli* CspD cold shock protein, an *Escherichia coli* CspG cold shock protein, and an *Agrobacterium tumefaciens* Csp2 cold shock protein. In certain embodiments, the recombinant DNA encodes a chimeric bacterial cold shock protein that comprises a protein with an amino acid sequence selected from the group consisting of SEQ ID NO: 16 through SEQ ID NO:23, SEQ ID NO: 313 through SEQ ID NO:426, and SEQ ID NO:427.

Also provided are recombinant DNAs comprising a promoter that functions in plants operably linked to a polynucleotide encoding a protein, wherein the protein is a variant of a *Bacillus subtilis* cspB protein having one or more amino acid substitutions in an amino acid position corresponding to amino acids F15, F17, F27, H29, or F30 of *Bacillus subtilis* cspB of SEQ ID NO:1. In certain embodiments, the recombinant DNA encodes a protein that comprises a protein with an amino acid sequence selected from the group consisting of SEQ ID NO:53 through SEQ ID NO:57, SEQ ID NO:458 through SEQ ID NO:577, and SEQ ID NO:578.

Also provided are recombinant DNAs comprising a promoter that functions in plants operably linked to a polynucleotide encoding a protein, wherein the protein is a variant of a *Bacillus subtilis* cspB protein having one or more amino acid substitutions in an amino acid position corresponding to amino acids S31 and T40 of *Bacillus subtilis* cspB of SEQ ID NO:1. In certain embodiments, the recombinant DNAs encodes a protein that comprises a protein with an amino acid sequence selected from the group consisting of SEQ ID NO:32, SEQ ID NO:33, SEQ ID NO:428 through SEQ ID NO:456, and SEQ ID NO:457.

Also provided are recombinant DNAs comprising a promoter that functions in plants operably linked to a polynucleotide encoding a protein, wherein the protein is a variant of a *Bacillus subtilis* cspB protein having at least two amino acid residues N and N+2 replaced with alanine residues, wherein N corresponds to any one of amino acids 2-65 of SEQ ID NO:1. In certain embodiments, the protein encoded by the recombinant DNA comprises a protein with an amino acid sequence selected from the group consisting of SEQ ID NO:270 through SEQ ID NO:311, and SEQ ID NO:312.

Also provided are recombinant DNAs comprising a promoter that functions in plants operably linked to a polynucleotide encoding a protein, wherein said protein is a variant of a *Bacillus subtilis* cspB protein comprising a mutation in a DOT1, DOT2, DOT3, DOT4, DOT5a, DOT5b, or DOT6 region of a *Bacillus subtilis* CspB protein, wherein said DOT1, DOT2, DOT3, DOT4, DOT5a, DOT5b, or DOT6 region are as provided in FIG. 2. In certain embodiments, the protein encoded by the recombinant DNA comprises a protein with an amino acid sequence selected from the group consisting of SEQ ID NO:15, SEQ ID NO:24 through SEQ ID NO:31, SEQ ID NO:58 through SEQ ID NO:269, SEQ ID NO:579 through SEQ ID NO:703, and SEQ ID NO:704.

Also provided herein are any of the aforementioned recombinant DNAs, wherein the promoter is selected from the group consisting of inducible promoters, constitutive promoters, temporal-regulated promoters, developmentally-regulated promoters, tissue-preferred promoters, cold enhanced promoters, cold-specific promoters, stress enhanced promoters, stress specific promoters, drought inducible promoters, water deficit inducible promoters, and tissue-specific promoters.

Also provided herein are cells that comprises any of the aforementioned recombinant DNA molecules. In certain embodiments, the cell is selected from the group consisting of a bacterial cell, a yeast cell, an isolated mammalian cell, and a plant cell. In certain embodiments, the cell is a plant cell, wherein the plant cell is in a transgenic plant, wherein any of the aforementioned recombinant DNAs is stably integrated into a chromosome of said transgenic plant cell and wherein the recombinant DNA confers abiotic stress-tolerance. In certain embodiments where the plant cell is in a transgenic plant, the plant is selected from the group consisting of soybean, corn, canola, rice, cotton, barley, oats, alfalfa, sugarcane, turf grass, cotton, and wheat. Also provided are: i) non-natural transgenic plant comprising a plurality of plant cells comprising the aforementioned recombinant DNA molecules; and ii) a plant propagule of the transgenic plants comprising a plurality of plant cells comprising the aforementioned recombinant DNA molecules. In certain embodiments, the plant propagule is a seed.

Also provided are methods for obtaining an abiotic-stress resistant plant comprising planting of a seed of the transgenic plants comprising a plurality of plant cells comprising the aforementioned recombinant DNA molecules.

Also provided are methods of producing non-natural transgenic plant seed comprising the steps of: a) screening a population of plants for enhanced abiotic stress tolerance and the presence of any of the aforementioned recombinant DNAs, wherein individual plants in the population exhibit said abiotic stress tolerance at a level less than, essentially the same as, or greater than the level that said abiotic stress tolerance is exhibited in control plants that do not contain said recombinant DNA; b) selecting from said population one or more plants that exhibit said abiotic stress tolerance trait at a level greater than the level that said trait is exhibited in control plants; and c) collecting seed from selected plants from step b. In certain embodiments of the methods, the enhanced abiotic stress tolerance is to an abiotic stress is selected from the group consisting of heat tolerance, salt tolerance, drought tolerance, and survival after cold shock.

Also provided are proteins encoded by the polynucleotide that is operably linked to the promoter of any of the aforementioned the recombinant DNAs. In certain embodiments, this protein is in a plant cell. In still other embodiments, this protein is in a processed plant product.

Also provided herein are processed plant products comprising a detectable amount of the polynucleotide that is operably linked to the promoter of any of the aforementioned recombinant DNAs. In certain embodiments, the processed plant product comprises a feed, a meal, a flour, an extract, or a homogenate, wherein said feed, meal, flour, extract, or homogenate is obtained from at least one plant part. In certain embodiments, the processed plant product can be obtained from a plant part that is a stem, a leaf, a root, a flower, a tuber, or a seed. In certain embodiments, the processed product can comprise an extract that comprises a composition enriched for one or more protein(s), one or more monosaccharide(s), one or more disaccharide(s), one or more polysaccharides, or one or more fatty acid(s).

Also provided herein are processed plant products comprising a detectable amount of the protein encoded by the polynucleotide that is operably linked to the promoter of any of the aforementioned recombinant DNAs. In certain embodiments, the processed plant product comprises a feed, a meal, a flour, an extract, or a homogenate, wherein said feed, meal, flour, extract, or homogenate is obtained from at least one plant part. In certain embodiments, the processed plant product can be obtained from a plant part that is a stem, a leaf, a root, a flower, a tuber, or a seed. In certain embodiments, the processed product can comprise an extract that comprises a composition enriched for one or more protein(s), one or more monosaccharide(s), one or more disaccharide(s), one or more polysaccharides, or one or more fatty acid(s).

Also provided herein is a plant genomic DNA comprising a recombinant DNA molecule of any one of claims 1-14, or 15, wherein said recombinant DNA is stably integrated into a chromosome of said plant genomic DNA and wherein said recombinant DNA confers abiotic stress-tolerance to a plant comprising said chromosome.

BRIEF DESCRIPTION OF THE DRAWINGS

FIG. 1 provides an alignment of the bacterial cold shock-proteins forming the basis for the proteins of the present invention. Regions used in generating domain swap variants are indicated as Reg1 through Reg5. Tt_Csp1 (SEQ3) is SEQ ID NO:3, Bs_CspB (SEQ1) is SEQ ID NO:1, Tm_Csp1 (SEQ2) is SEQ ID NO:2, Ec_CspC (SEQ4) is SEQ ID NO:4, Ec_CspG (SEQ 7) is SEQ ID NO:7, Ec_CspD (SEQ 5) is SEQ ID NO:5, and Ab_Csp2 (SEQ 6) is SEQ ID NO:6.

FIG. 2 displays regions and specific targeted amino acid substitutions for variant generation using degenerate oligonucleotides. The topmost sequence is SEQ ID NO:1.

DETAILED DESCRIPTION OF THE INVENTION

Figure 3:
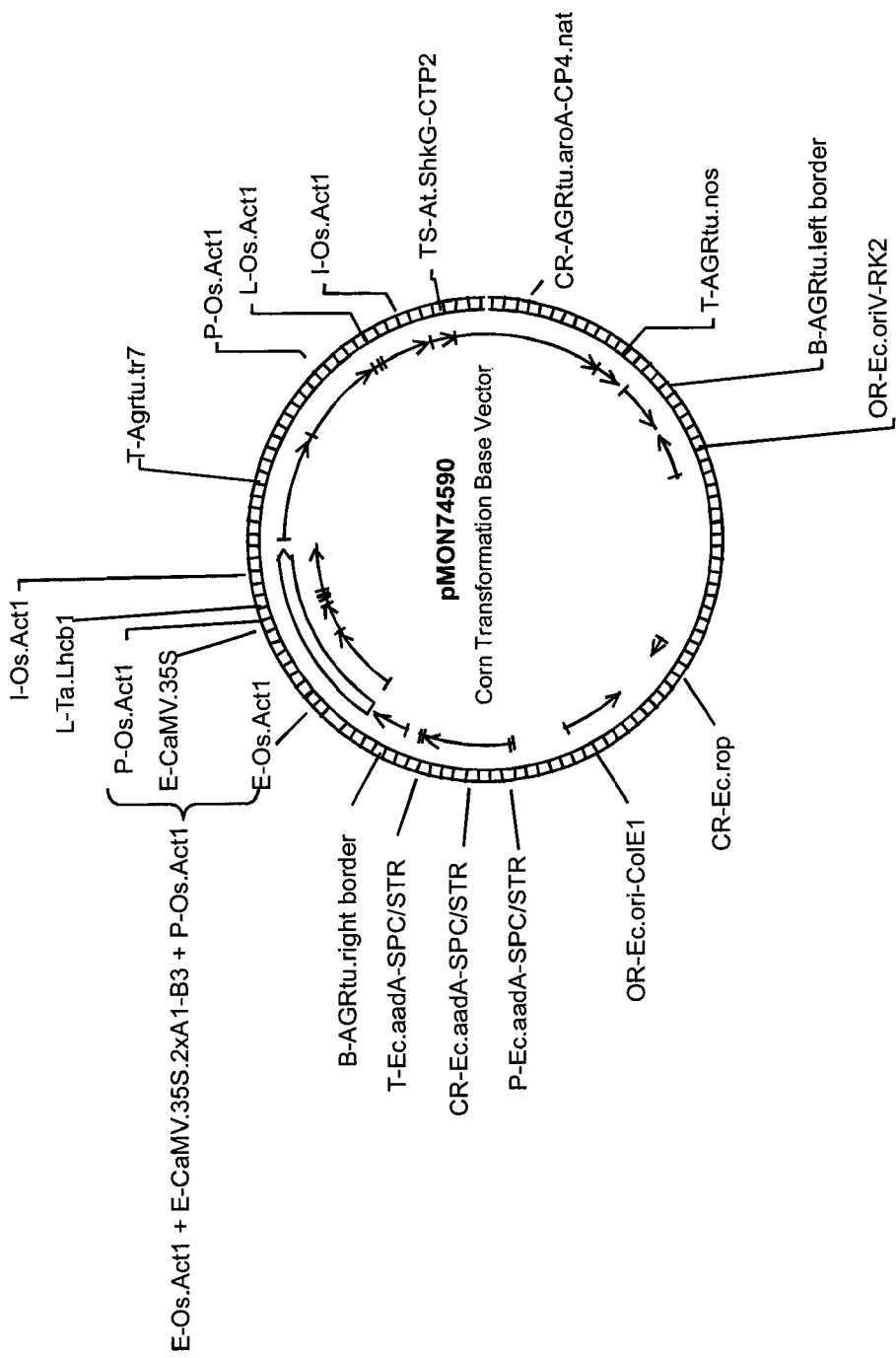
FIG. 3 discloses a base vector for corn transformation.

The invention provides recombinant DNA derived from DNA encoding bacterial cold shock proteins where the recombinant DNA encodes a protein having one or more amino acid substitutions in the sequence of *Bacillus subtilis* CspB L2V (SEQ ID NO:1) or region swaps from among cold shock proteins from *Escherichia coli* (CspC (SEQ ID NO:4), CspD (SEQ ID NO:5), and CspG (SEQ ID NO:7)), *Thermoanaerobacter tengcongensis* (SEQ ID NO:3), *Thermotoga maritime* (SEQ ID NO:2), *Agrobacterium tumefaciens* (SEQ ID NO:6) and *Bacillus subtilis* (SEQ ID NO:1). DNA encoding these cold shock proteins are provided as SEQ ID NO:8 through SEQ ID NO:14.

As used herein, the phrases "bacterial cold shock protein(s)", "bacterial Csp(s))" or "bacterial CSP(s))" refers to any of: i) proteins that have at least 40% identity to any one of *Bacillus subtilis* CspB L2V (SEQ ID NO:1), *Thermotoga maritime* (SEQ ID NO:2), *Thermoanaerobacter tengcongensis* (SEQ ID NO:3), *Escherichia coli* CspC (SEQ ID NO:4), *Escherichia coli* CspD (SEQ ID NO:5), *Agrobacterium tumefaciens* (SEQ ID NO:6), or *Escherichia coli* CspG (SEQ ID NO:7); and/or, ii) proteins comprising the conserved cold shock domain (Prosite motif PS00352; Bucher and Bairoch, (In) ISMB-94; Proceedings 2nd International Conference on Intelligent Systems for Molecular Biology, Altman R., Brutlag D., Karp P., Lathrop R., Searls D., Eds., pp 53-61, AAAIPress, Menlo Park, 1994; Hofmann et al., Nucleic Acids Res. 27:215, 1999). A bacterial cold shock protein, as described herein, is thus at least 40% identical, more preferably at least 50% identical, more preferably at least 60% identical, more preferably at least 70% identical, more preferably at least 80% identical, more preferably at least 90% identical, more preferably at least 95% identical, and most preferably at least 98% identical to any one of *Bacillus subtilis* CspB L2V (SEQ ID NO:1), *Thermotoga maritime* (SEQ ID NO:2), *Thermoanaerobacter tengcongensis* (SEQ ID NO:3), *Escherichia coli* CspC (SEQ ID NO:4), *Escherichia coli* CspD (SEQ ID NO:5), *Agrobacterium tumefaciens* (SEQ ID NO:6), or *Escherichia coli* CspG (SEQ ID NO:7). Lists of various bacterial cold shock proteins useful in the practice of this invention are provided in US Patent Application publication US 2005/0097640, which is incorporated herein by reference in its entirety.

As used herein "enhanced abiotic stress tolerance" characterizes a transgenic plant with enhanced tolerance to a high salt environment, heat exposure, drought exposure or water deficit environment or cold exposure as compared to a control plant.

As used herein "water deficit" means a period when water available to a plant is not replenished at the rate at which it is consumed by the plant. A long period of water deficit is colloquially called drought. Lack of rain or irrigation may not produce immediate water stress if there is an available reservoir of ground water for the growth rate of plants. Plants grown in soil with ample groundwater can survive days without rain or irrigation without adverse affects on yield. Plants grown in dry soil are likely to suffer adverse affects with minimal periods of water deficit. Severe water deficit stress can cause wilt and plant death; moderate drought can cause reduced yield, stunted growth or retarded development. Plants can recover from some periods of water deficit stress without significantly affecting yield. However, water deficit stress at the time of pollination can have an irreversible effect in lowering yield. Thus, a useful period in the life cycle of corn for observing water deficit stress tolerance is the late vegetative stage of growth before tasseling. Water deficit stress tolerance is determined by comparison to control plants. For instance, plants of this invention can survive water deficit stress with a higher yield than control plants. In the laboratory and in field trials drought can be simulated by giving plants of this invention and control plants less water than is given to sufficiently-watered control plants and measuring differences in traits.

A "control plant" may be a non-transgenic plant of the parental line used to generate a transgenic plant herein. A control plant may in some cases be a transgenic plant line that includes an empty vector or marker gene, but does not contain the recombinant polynucleotide of the present invention that is expressed in the transgenic plant being evaluated. A control plant in other cases is a transgenic plant expressing the gene with a constitutive promoter. In general, a control plant is a plant of the same line or variety as the transgenic plant being tested, lacking the specific trait-conferring, recombinant DNA that characterizes the transgenic plant. Such a progenitor plant that lacks that specific trait-conferring recombinant DNA can be a natural, wild-type plant, an elite, non-transgenic plant, or a transgenic plant without the specific trait-conferring, recombinant DNA that characterizes the transgenic plant. The progenitor plant lacking the specific, trait-conferring recombinant DNA can be a sibling of a transgenic plant having the specific, trait-conferring recombinant DNA. Such a progenitor sibling plant may include other recombinant DNA In an important aspect of the invention the transgenic plants have enhanced yield, including increased yield under abiotic stress conditions and increased yield under non-stress conditions. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Moreover a bushel of corn is defined by law in the State of Iowa as 56 pounds by weight, a useful conversion factor for corn yield is: 100 bushels per acre is equivalent to 6.272 metric tons per hectare. Other measurements for yield are in common practice.

A transgenic "plant cell" means a plant cell that is transformed with stably-integrated, non-natural, recombinant polynucleotides, e.g. by *Agrobacterium*-mediated transformation or by bombardment using microparticles coated with recombinant polynucleotides. A plant cell of this invention can be an originally-transformed plant cell that exists as a microorganism or as a progeny plant cell that is regenerated into differentiated tissue, e.g. into a transgenic plant with stably-integrated, non-natural recombinant polynucleotides in its chromosomal DNA, or seed or pollen derived from a progeny transgenic plant.

A "transgenic" plant or seed means one whose genome has been altered by the stable integration of recombinant polynucleotides in its chromosomal DNA, e.g. by transformation, by regeneration from a transformed plant from seed or propagule or by breeding with a transformed plant. Thus, transgenic plants include progeny plants of an original plant derived from a transformation process including progeny of breeding transgenic plants with wild type plants or other transgenic plants. The enhancement of a desired trait can be measured by comparing the trait property in a transgenic plant which has recombinant DNA conferring the trait to the trait level in a progenitor plant. Although many varieties of plants can be advantageously transformed with recombinant DNA for expressing a variant bacterial cold shock protein to provide stress tolerance and/or enhanced yield, especially useful abiotic stress tolerant transgenic plants include corn (maize), soybean, cotton, canola (rape), wheat, rice, alfalfa, sorghum, grasses such as switchgrass, vegetables and fruits.

"Expressing a protein" means the function of a cell to transcribe recombinant DNA to mRNA and translate the mRNA to a protein. For expression the recombinant DNA usually includes regulatory elements including 5' regulatory elements such as promoters, enhancers, and introns; other elements can include polyadenylation sites, transit peptide DNA, markers and other elements commonly used by those skilled in the art. Promoters can be modulated by proteins such as transcription factors and by intron or enhancer elements linked to the promoter. Promoters in recombinant polynucleotides can also be modulated by nearby promoters.

"Recombinant DNA" means non-natural DNA, that has been prepared by modifying natural DNA or by combining segments of DNA, e.g., by chemical synthesis or by the manipulation of isolated segments of nucleic acids by genetic engineering techniques. Recombinant DNA for expressing a protein in a plant is typically provided as an expression cassette which has a promoter that is active in plant cells operably linked to DNA encoding a protein, e.g. a variant bacterial cold shock protein, linked to a 3' DNA element for providing a polyadenylation site and signal. Useful recombinant DNA also includes expression cassettes for expressing one or more proteins conferring herbicide tolerance and/or insect resistance. Useful promoters for expressing the variant cold shock proteins of the present invention in transgenic plant cells include constitutive promoters such as those from rice actin, rice GOS2 (SEQ ID NO:705), and CaMV 35S. Promoters for use in the present invention may include a number of regulatory elements, such as enhancers, leaders and introns. Also of interest are chimeric promoters which include regulatory elements from different sources, such as the CaMV 35S enhanced rice actin promoter provided herein as SEQ ID NO:706. These and numerous other promoters that function in plant cells are known to those skilled in the art and available for use in alternative embodiments of this invention to provide for expression of variant bacterial cold shock proteins in transgenic plant cells.

Recombinant DNA constructs also generally include a 3' element that typically contains a polyadenylation signal and site. Well-known 3' elements include those from *Agrobacterium tumefaciens* genes such as nos 3', tml 3', tmr 3, tms 3', ocs 3', tr7 3', e.g., disclosed in U.S. Pat. No. 6,090,627. 3' elements from plant genes such as wheat (*Triticum aestivum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene are disclosed in U.S. published patent application 2002/0192813 A1.

Constructs and vectors may also include a transit peptide for targeting of a gene target to a plant organelle, particularly to a chloroplast, leucoplast or other plastid organelle. The use of chloroplast transit peptides is disclosed in U.S. Pat. Nos. 5,188,642 and 5,728,925.

Plant Cell Transformation Methods

Numerous methods for transforming plant cells with recombinant DNA are known in the art and may be used in the present invention. Two commonly used methods for plant transformation are *Agrobacterium*-mediated transformation and microprojectile bombardment. Microprojectile bombardment methods are illustrated in U.S. Pat. Nos. 5,015,580 (soybean); 5,550,318 (corn); 5,538,880 (corn); 5,914,451 (soybean); 6,160,208 (corn); 6,399,861 (corn) and 6,153,812 (wheat) and *Agrobacterium*-mediated transformation is described in U.S. Pat. Nos. 5,159,135 (cotton); 5,824,877 (soybean); 5,591,616 (corn); and 6,384,301 (soybean), all of which are incorporated herein by reference. For *Agrobacterium tumefaciens* based plant transformation system, additional elements present on transformation constructs will include T-DNA left and right border sequences to facilitate incorporation of the recombinant polynucleotide into the plant genome.

In general it is useful to introduce recombinant DNA randomly, i.e. at a non-specific location, in the genome of a target plant line. In special cases it may be useful to target recombinant DNA insertion in order to achieve site-specific integration, for example to replace an existing gene in the genome, to use an existing promoter in the plant genome, or to insert a recombinant polynucleotide at a predetermined site known to be active for gene expression. Several site specific recombination systems exist which are known to function implants include cre-lox as disclosed in U.S. Pat. No. 4,959,317 and FLP-FRT as disclosed in U.S. Pat. No. 5,527,695.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, for example various media and recipient target cells, transformation of immature embryo cells and subsequent regeneration of fertile transgenic plants are disclosed in U.S. Pat. Nos. 6,194,636 and 6,232,526, which are incorporated herein by reference.

The seeds of transgenic plants can be harvested from fertile transgenic plants and be used to grow progeny generations of transformed plants of this invention including hybrid plants line for selection of plants having an enhanced trait. In addition to direct transformation of a plant with a recombinant DNA, transgenic plants can be prepared by crossing a first plant having a recombinant DNA with a second plant lacking the DNA. For example, recombinant DNA can be introduced into first plant line that is amenable to transformation to produce a transgenic plant which can be crossed with a second plant line to introgress the recombinant DNA into the second plant line. A transgenic plant with recombinant DNA providing an enhanced trait, e.g. enhanced stress tolerance and/or yield, can be crossed with a transgenic plant line having other recombinant DNA that confers another trait or traits, for example herbicide resistance or pest resistance, to produce progeny plants having recombinant DNA that confers multiple traits. Typically, in breeding to combine traits the transgenic plant donating the additional trait is a male line and the transgenic plant carrying the base trait or traits is the female line. The progeny of this cross will segregate such that some of the plants will carry the DNA for traits present in both parents and some will carry DNA for the trait or traits from only one parent; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for traits from both parents can be crossed back into the female parent line multiple times, for example usually 6 to 8 generations, to produce a progeny plant with substantially the same genotype as one original transgenic parental line but for the recombinant DNA of the other transgenic parental line.

In the practice of transformation DNA is typically introduced into only a small percentage of target plant cells in any one transformation experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV) and gentamycin (aac3 and aacC4) or resistance to herbicides such as glufosinate (bar or pat) and glyphosate (aroA or EPSPS). Examples of such selectable are illustrated in U.S. Pat. Nos. 5,550,318; 5,633,435; 5,780,708 and 6,118,047. Selectable markers which provide an ability to visually identify transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Transgenic plant cells that survive exposure to the selective agent or transgenic plant cells that have been scored positive in a screening assay are typically cultured in regeneration media and allowed to mature into plants. For example developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2} s^{-1}$ of light, prior to transfer to a greenhouse or growth chamber for maturation. Plants are regenerated from about 6 weeks to 10 months after a transformant is identified, depending on the initial tissue. Plants may be pollinated using conventional plant breeding methods known to those of skill in the art and seed produced, for example self-pollination is commonly used with transgenic corn. The non-natural regenerated transgenic plants or progeny plants can be tested for the presence and expression of the recombinant DNA and selected for the presence of enhanced stress tolerance.

Transgenic Plants and Seeds

Non-natural transgenic plants derived from the plant cells of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) including the recombinant DNA, for example multiple plants from 2 to 20 or more transgenic events. Transgenic plants grown from transgenic seed provided herein demonstrate enhanced stress tolerance that contributes to increased yield.

Not all transgenic events will be in transgenic plant cells that provide plants and seeds with an enhanced or desired trait depending on factors, such as location and integrity of the recombinant DNA, copy number, unintended insertion of other DNA, etc. As a result transgenic plant cells of this invention are identified by screening transformed progeny plants for enhanced stress tolerance and yield. For efficiency a screening program is designed to evaluate multiple transgenic plants preferably with a single copy of the recombinant DNA from two or more transgenic events.

Transgenic plants having enhanced water use efficiency are identified by screening plants in an assay where water is withheld for period to induce stress followed by watering to revive the plants. For example, a useful selection process for water defect tolerant transgenic corn plants imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

Transgenic plants having enhanced cold tolerance are identified by screening plants in a cold germination assay and/or a cold tolerance field trial. In a cold germination assay trays of transgenic and control seeds are placed in a growth chamber at 9.7° C. for 24 days (no light). Seeds having higher germination rates as compared to the control are identified as having enhanced cold tolerance. In a cold tolerance field trial plants with enhanced cold tolerance are identified from field planting at an earlier date than conventional Spring planting for the field location. For example, seeds are planted into the ground around two weeks before local farmers begin to plant corn so that a significant cold stress is exerted onto the crop, named as cold treatment. Seeds also are planted under local optimal planting conditions such that the crop has little or no exposure to cold condition, named as normal treatment. At each location, seeds are planted under both cold and normal conditions preferably with multiple repetitions per treatment.

Transgenic plants having enhanced yield are identified by screening using progeny of the transgenic plants over multiple locations with plants grown under optimal production management practices and maximum weed and pest control. A useful target for improved yield is a 5% to 10% increase in yield as compared to yield produced by plants grown from seed for a control plant. Selection methods may be applied in multiple and diverse geographic locations, for example up to 16 or more locations, over one or more planting seasons, for example at least two planting seasons, to statistically distinguish yield improvement from natural environmental effects.

The following examples are included to demonstrate embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings and examples is to be interpreted as illustrative and not in a limiting sense.

Example 1

This example illustrates the preparation of recombinant DNA encoding proteins derived from bacterial cold shock proteins. Recombinant DNA is prepared which encodes proteins having single amino acid changes at amino acid positions F15, F17, F27, H29 and F30 of Bs-CspB_L2V (SEQ ID NO:1) using degenerate 2'-OMe primers. DNA generated in this manner encodes proteins with the amino acid sequence of SEQ ID NO:53 through SEQ ID NO:57 and SEQ ID NO:458 through SEQ ID NO:578.

Recombinant DNA is prepared which encodes proteins with Single amino acid changes at positions S31 and T40 of Bs-CspB_L2V (SEQ ID NO:1). DNA generated in this manner encodes proteins with amino acid sequence of SEQ ID NO:32, SEQ ID NO:33 and SEQ ID NO:428 through SEQ ID NO:457.

Recombinant DNA was prepared which encodes protein variants of Bs-CspB with two amino acid residues, N and N+2 (where N is any one of amino acids 2-65 of SEQ ID NO:1), replaced with alanine residues. Where the amino acid at position N or N+2 is alanine, a serine was substituted for alanine. DNA generated in this manner encodes proteins with the amino acid sequence of SEQ ID NO:275 through SEQ ID NO:312. Other recombinant DNAs encoding protein variants of Bs-CspB with multiple alanine substitutions were made and encode proteins with the amino acid sequence of SEQ ID NO:270 through SEQ ID NO:274.

Recombinant DNAs were also prepared by exchanging reciprocal DNA regions encoding the amino acid regions identified as "Reg 1"-"Reg 5" (See FIG. 1) of the bacterial cold shock proteins of SEQ ID NOS: 1-7. DNA generated by region exchange encoded proteins having the amino acid sequence of SEQ ID NO:16 through SEQ ID NO:23 and SEQ ID NO:313 through SEQ ID NO:427. The proteins encoded by the DNAs generated in this manner are designated as chimeric in the sequence listing. The name in the comments field for each protein indicates the donor region and the backbone sequence for the regions in the variant proteins. For example, Chimeric Tm_Csp1_R2_Bs_CspB_bb refers to a chimeric variant bacterial cold shock protein sequence (SEQ ID NO:17) having the R2 region of *Thermotoga maritime* Csp1 exchanged into the backbone sequence of *Bacillus subtilis* CspB.

Recombinant DNA encoding variant proteins of Bs-CspB having modifications in identified areas of sequence diversity and amino acid sequences that lie within the loop regions of Bs-CspB are generated using a degenerate oligonucleotide tail approach. The regions and specific targeted amino acid substitutions for variant generation are shown in FIG. 2. DNAs produced as the result of this approach encode proteins having amino acid sequences of SEQ ID NO:15, SEQ ID NO:24 through SEQ ID NO:31, SEQ ID NO:58 through SEQ ID NO:269 and SEQ ID NO:579 through SEQ ID NO:704.

Proteins encoded by the recombinant DNAs were expressed, purified and analyzed to determine their ability to complement the cold sensitivity of a quadruple *E. coli* mutant, BX04 (DE3) and to determine their ability to destabilize single stranded DNA secondary structure and bind to single stranded DNA. Constructs for expression of the proteins in transgenic plants are prepared using each of the recombinant DNAs operably linked to a promoter operable in plant cells.

Example 2

This example, illustrates preparation of recombinant DNA constructs for transformation of corn, rice, *Arabidopsis*, soybean, and cotton.

Plant Expression Constructs for Corn Transformation.

A base vector useful for *Agrobacterium*-mediated transformation of corn, pMON74590, is shown in FIG. 3. The vector provides an expression cassette for expression of DNA encoding proteins prepared in Example 1 under the control of an enhanced 35S/rice actin promoter (SEQ ID NO:706). The transformation vector also contains an EPSPS gene as a selectable marker for resistance to glyphosate herbicide. The glyphosate resistance expression cassette comprises a rice actin 1 promoter, leader and intron operably linked to a DNA encoding a chloroplast transit peptide from an *Arabidopsis thaliana* EPSPS gene and DNA encoding an EPSPS from an *A. tumefaciens* gene (CP4) and a 3' element from an *A. tumefaciens* nopaline synthase gene. DNA having the sequence of SEQ ID NO: 34 through SEQ ID NO:52, encoding proteins prepared in Example 1, is cloned into pMON74590 and the resulting constructs are used for production of transgenic corn plants expressing variant bacterial cold shock proteins of SEQ ID NO:15 through SEQ ID NO:33.

PLANT EXPRESSION CONSTRUCTS fOR RICE TRANSFORMATION

Figure 4:
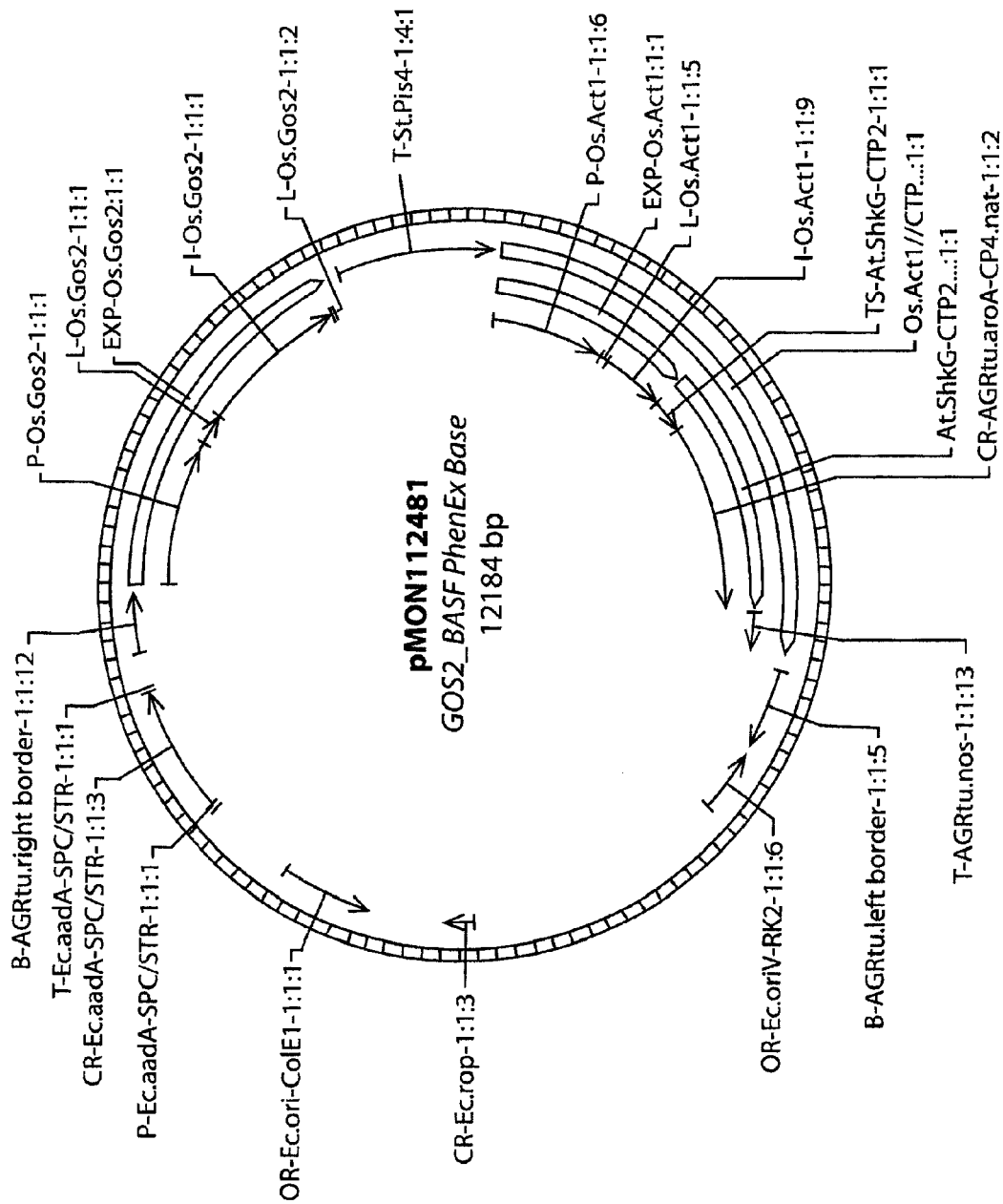
FIG. 4 discloses a base vector for rice transformation.

A base vector useful for *Agrobacterium*-mediated transformation of rice, pMON112481, is shown in FIG. 4. The vector provides for enhanced protein expression under the control of a rice GOS2 gene promoter (SEQ ID NO:705). The transformation vector also contains an EPSPS gene as a selectable marker for resistance to glyphosate herbicide. The glyphosate resistance expression cassette comprises a rice actin 1 promoter, leader and intron operably linked to a DNA encoding a chloroplast transit peptide from an *Arabidopsis thaliana* EPSPS gene and DNA encoding an EPSPS from an *A. tumefaciens* gene (CP4) and a 3' element from an *A. tumefaciens* nopaline synthase gene. DNA having the sequence of SEQ ID NO: 34 through SEQ ID NO:52, encoding proteins prepared in Example 1, is cloned into pMON112481 and the resulting constructs are used for production of transgenic corn plants expressing variant bacterial cold shock proteins of SEQ ID NO:15 through SEQ ID NO:33.

Plant Expression Constructs for Transformation of *Arabidopsis*

Figure 5:
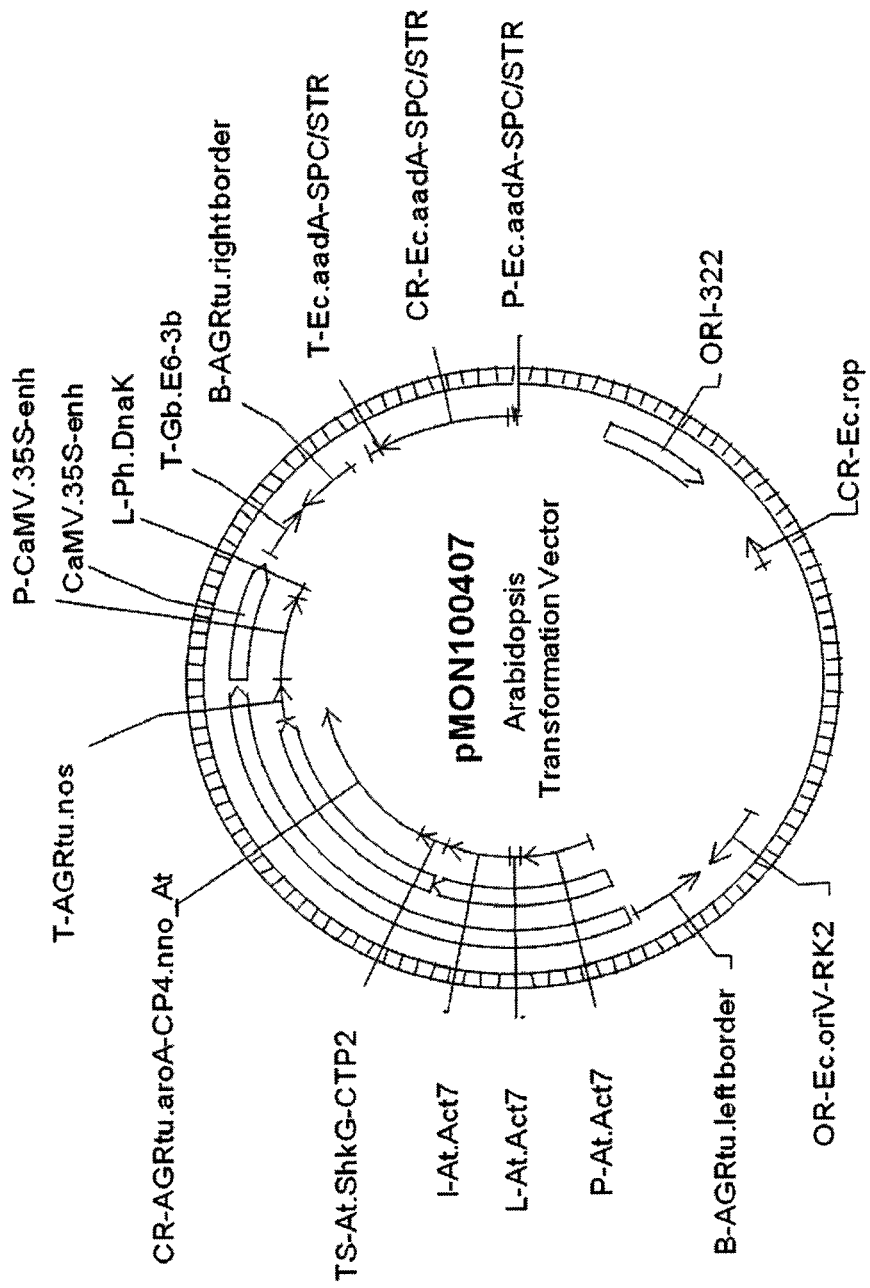
FIG. 5 discloses a base vector for *Arabidopsis* transformation.

A base vector useful for *Agrobacterium*-mediated transformation of *Arabidopsis*, pMON100407, is shown in FIG. 5. The vector provides for enhanced protein expression under the control of an enhanced Cauliflower Mosaic Virus 35S promoter (U.S. Pat. No. 5,359,142). The transformation vector also contain an EPSPS gene as a selectable marker for resistance to glyphosate herbicide. The glyphosate resistance expression cassette comprises a rice actin 1 promoter, leader and intron operably linked to a DNA encoding a chloroplast transit peptide from an *Arabidopsis thaliana* EPSPS gene and DNA encoding an EPSPS from an *A. tumefaciens* gene (CP4) and a 3' element from an *A. tumefaciens* nopaline synthase gene. DNA having the sequence of SEQ ID NO: 34 through SEQ ID NO:52, encoding proteins prepared in Example 1, is cloned into pMON100407 and the resulting constructs are used for production of transgenic *Arabidopsis* plants expressing variant bacterial cold shock proteins of SEQ ID NO:15 through SEQ ID NO:33. Additional constructs are generated using recombinant DNA encoding variant bacterial cold shock proteins of SEQ ID NO:258, SEQ ID NO:268, SEQ ID NO:331, SEQ ID NO:333, SEQ ID NO:334, SEQ ID NO:343, SEQ ID NO:353, SEQ ID NO:355, SEQ ID NO:367, SEQ ID NO:377, SEQ ID NO:380, SEQ ID NO:381, SEQ ID NO:385, SEQ ID NO:391, SEQ ID NO:397, SEQ ID NO:403, SEQ ID NO:449 and SEQ ID NO:622. The transformation of *Arabidopsis* plants is carried out using a vacuum infiltration method (Bechtold, e.g., Meth- ods Mol. Biol. 82:259-66, 1998). Seeds harvested from the transgenic plants, T1 seeds, are grown in a glufosinate-containing selective medium to select for transformed plants that produce T2 transgenic seed.

Plant Expression Constructs for Soybean Transformation

Figure 6:
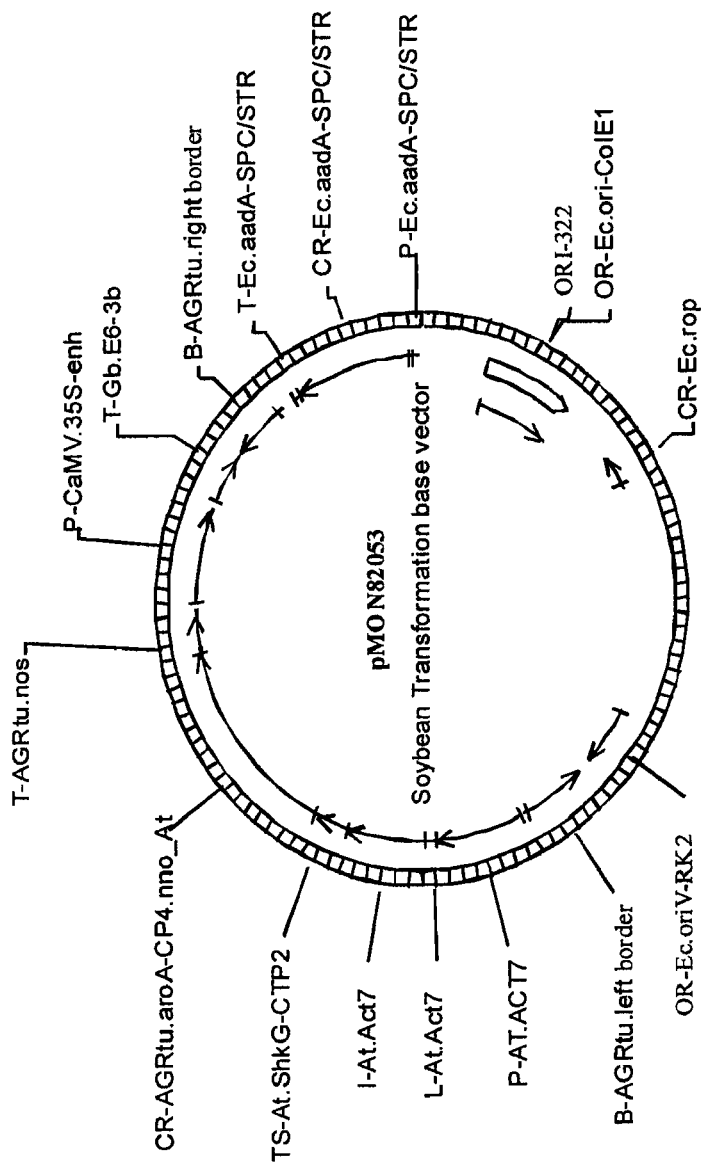
FIG. 6 discloses a base vector for soybean transformation.

A base vector useful for *Agrobacterium*-mediated transformation of soybean, pMON82053, is shown in FIG. 6. The vector provides for enhanced protein expression under the control of an enhanced Cauliflower Mosaic Virus 35S promoter (U.S. Pat. No. 5,359,142). The transformation vector also contain an EPSPS gene as a selectable marker for resistance to glyphosate herbicide. The glyphosate resistance expression cassette comprises a rice actin 1 promoter, leader and intron operably linked to a DNA encoding a chloroplast transit peptide from an *Arabidopsis thaliana* EPSPS gene and DNA encoding an EPSPS from an *A. tumefaciens* gene (CP4) and a 3' element from an *A. tumefaciens* nopaline synthase gene. Recombinant DNA for expression of variant bacterial cold shock proteins is cloned into pMON82053 and the resulting constructs are used for transformation of transgenic soybean plants expressing variant bacterial cold shock proteins.

Plant Expression Constructs for Cotton Transformation

Figure 7:
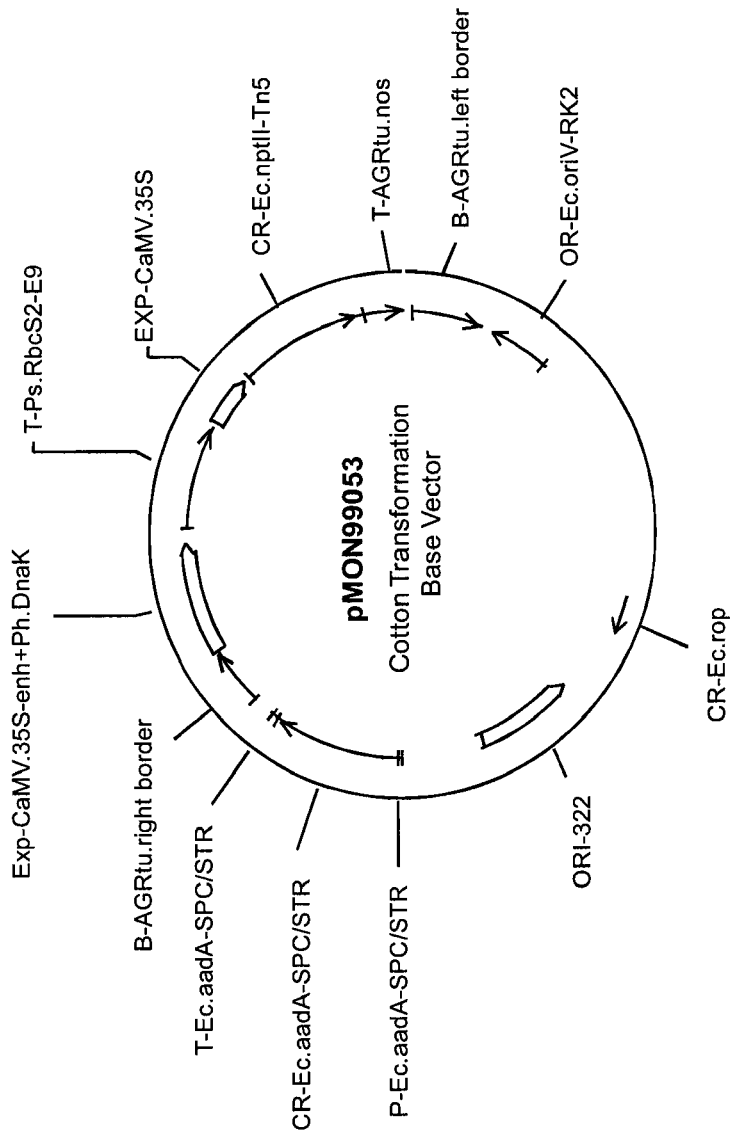
FIG. 7 discloses a base vector for cotton transformation.

A base vector useful for *Agrobacterium*-mediated transformation of cotton, pMON99053, is shown in FIG. 7. The vector provides for enhanced protein expression under the control of an enhanced CaMV 35S promoter. The transformation vectors also contain an nptII gene as a selectable marker for resistance to antibiotics such as kanamycin. Recombinant DNA for expression of variant bacterial cold shock proteins is cloned into pMON99053 and the resulting constructs are used for transformation of transgenic cotton plants expressing variant bacterial cold shock proteins.

Example 3

This example illustrates the production of multiple transgenic events of transgenic corn plants expressing each of the recombinant DNAs prepared in Example 1 using the vectors prepared in Example 2.

Transgenic corn plants are made from cells transformed by *Agrobacterium* mediated transformation using DNA constructs prepared in Example 2. Transgenic plants having recombinant DNA stably inserted in the chromosome and expressing proteins having the amino acid sequences of SEQ ID NO:15 through SEQ ID NO:33, are evaluated for stress tolerance, including yield under water deficit stress. Events of these transgenic plants are identified that have increased tolerance to abiotic stress as compared to control plants. Transgenic seed is collected from the identified plants.

Example 4

Transgenic rice plants are prepared by *Agrobacterium* mediated transformation using DNA constructs described in Example 2. Transgenic plants having recombinant DNA stably inserted in the chromosome and expressing a protein prepared in Example 1 are identified and evaluated for stress tolerance, including yield under water deficit stress. Events of these transgenic plants are identified that have increased tolerance to abiotic stress as compared to control plants. Transgenic seed is collected from the identified plants.

Example 5

Transgenic cotton plants are prepared by *Agrobacterium* mediated transformation using DNA constructs described in Example 2. Transgenic plants having recombinant DNA stably inserted in the chromosome and expressing a protein prepared in Example 1 are identified and evaluated for stress tolerance, including yield under water deficit stress. Events of these transgenic plants are identified that have increased tolerance to abiotic stress as compared to control plants. Transgenic seed is collected from the identified plants.

Example 6

Transgenic soybean plants are prepared by *Agrobacterium* mediated transformation using DNA constructs described in Example 2. Transgenic plants having recombinant DNA stably inserted in the chromosome and expressing a protein prepared in Example 1 are identified and evaluated for stress tolerance, including yield under water deficit stress. Events of these transgenic plants are identified that have increased tolerance to abiotic stress as compared to control plants. Transgenic seed is collected from the identified plants.

Example 7

Transgenic alfalfa, canola, switchgrass and sugarcane plants comprising DNA constructs stably inserted in the chromosome and expressing a protein prepared in Example 1 are prepared and evaluated for stress tolerance, including yield under water deficit stress. Events of these transgenic plants are identified that have increased tolerance to abiotic stress as compared to control plants. Transgenic seed is collected from the identified plants.

Example 8

This example illustrates the various stress tolerance properties of heterozygous hybrid corn plants expressing a protein with a cold shock domain. Corn plants were screened for enhanced cold stress tolerance by measuring germination and/or early seedling growth at cold temperature, water deficit stress tolerance in a greenhouse "drought" screen, and water deficit tolerance in a random field screen in which plants from randomly planted seed were subjected to water deficit allowing an investigator to observe and select plants with positive water deficit tolerance. Reference is made to Table 1 showing the number of transgenic events tested for recombinant DNA expressing the various proteins and whether events were identified as showing water deficit or cold stress tolerance.

TABLE 1

| Expressed protein | SEQ ID NO: | Water stress tolerance in greenhouse screen | Water stress tolerance in random field screen | Increased yield under water stress (field screen) | Cold stress tolerance |
| --- | --- | --- | --- | --- | --- |
| *B. subtilis* cspB L2V | 1 | Yes | | Yes | No |
| *E. coli* cspC | 4 | | Yes | | Yes |
| *E. coli* cspD | 5 | Yes | No | | No |
| *Agrobacterium tumefaciens* Csp2 | 6 | No | | | No |
| *Agrobacterium tumefaciens* Csp4 | | Yes | Yes | | Yes |
| *E. coli* cspA | | Yes | | No | No |
| *E. coli* cspG | 7 | No | No | | Yes |
| *Arabidopsis* csp-like 1 | | Yes | No | | No |
| cotton csp-like 1 | | Yes | No | No | Yes |
| cotton csp-like 2 | | Yes | No | Yes | Yes |
| Bs_cspB-L2V-F30R | 53 | | Yes | No | |
| Bs_cspB-L2V-F15Y | 54 | | Yes | No | |
| Bs_cspB-L2V-F15R | 55 | | No | No | |
| Bs_cspB-L2V-F30W | 56 | | No | No | |
| Bs_cspB-L2V-F15Y:F30W | 57 | | No | No | |

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations may be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A recombinant DNA comprising a promoter that functions in plants operably linked to a polynucleotide encoding a protein, wherein said protein is a variant of a *Bacillus subtilis* cspB protein comprising an amino acid sequence having at least 90% identity to SEQ ID NO:1 and having at least three mutations in the DOT6 region of residues 61 to 66 of SEQ ID NO:1, wherein at least one of said mutations is a substitution of residue 61 or 62.

2. The recombinant DNA of claim 1, wherein said protein comprises a protein with an amino acid sequence selected from the group consisting of SEQ ID NO: 24 through 28, SEQ ID NO: 31, SEQ ID NO: 73, SEQ ID NO: 75 through SEQ ID NO: 77, SEQ ID NO: 79 through SEQ ID NO: 89, SEQ ID NO: 91 through SEQ ID NO: 98, SEQ ID NO: 222 through SEQ ID NO: 225, SEQ ID NO: 227 through SEQ ID NO: 229, SEQ ID NO: 231 through SEQ ID NO: 240, SEQ ID NO: 242 through SEQ ID NO: 246, SEQ ID NO: 597 through SEQ ID NO: 601, SEQ ID NO: 604 through SEQ ID NO: 612, SEQ ID NO: 614 through SEQ ID NO: 635, and SEQ ID NO: 690 through SEQ ID NO: 704.

3. The recombinant DNA according to claim 1, wherein the promoter is selected from the group consisting of inducible promoters, constitutive promoters, temporal-regulated promoters, developmentally-regulated promoters, tissue-preferred promoters, cold enhanced promoters, cold-specific promoters, stress enhanced promoters, stress specific promoters, drought inducible promoters, water deficit inducible promoters, and tissue-specific promoters.

4. A non-natural transgenic plant comprising a plurality of plant cells that comprise the recombinant DNA molecule according to claim 1.

5. A transgenic plant propagule of the transgenic plant of claim 4, wherein said transgenic plant propagule comprises the recombinant DNA molecule.

6. The plant propagule of claim 5, wherein said transgenic propagule is a seed.

7. A processed plant product comprising a detectable amount of the polynucleotide that is operably linked to the promoter of the recombinant DNA of claim 1.

8. The processed plant product of claim 7, wherein said product comprises a feed, a meal, a flour, an extract, or a homogenate, and wherein said feed, meal, flour, extract, or homogenate is obtained from at least one plant part.

9. The processed plant product of claim 8, wherein said plant part is a stem, a leaf, a root, a flower, a tuber, or a seed.

10. The processed product of claim 7, wherein said extract comprises a composition enriched for one or more protein(s), one or more monosaccharide(s), one or more disaccharide(s), one or more polysaccharides, or one or more fatty acid(s).

11. The recombinant DNA of claim 1, wherein said protein is a variant of a *Bacillus subtilis* cspB protein comprising an amino acid sequence having at least 95% identity to SEQ ID NO:1 and having the amino acid sequence of residues 1-60 of SEQ ID NO:1.

12. The recombinant DNA of claim 1, wherein said protein comprises the amino acid sequence of SEQ ID NO:24.

13. The transgenic plant of claim 4, wherein said protein is a variant of a *Bacillus subtilis* cspB protein comprising an amino acid sequence having at least 95% identity to SEQ ID NO:1 and having the amino acid sequence of residues 1-60 of SEQ ID NO:1.

14. The transgenic plant of claim 4, wherein said protein comprises the amino acid sequence of SEQ ID NO:24.

15. The plant propagule of claim 5, wherein said protein is a variant of a *Bacillus subtilis* cspB protein comprising an amino acid sequence having at least 95% identity to SEQ ID NO:1 and having the amino acid sequence of residues 1-60 of SEQ ID NO:1.

16. The plant propagule of claim 5, wherein said protein comprises the amino acid sequence of SEQ ID NO:24.

* * * * *